(12) United States Patent
Yun et al.

(10) Patent No.: US 12,236,681 B2
(45) Date of Patent: Feb. 25, 2025

(54) METHOD FOR PROVIDING TACTICAL INFORMATION RELATED TO TEAM SPORTS

(71) Applicant: FITOGETHER INC., Seoul (KR)

(72) Inventors: Jinsung Yun, Seoul (KR); Hyunsung Kim, Seoul (KR)

(73) Assignee: FITOGETHER INC., Seoul (KR)

( * ) Notice: Subject to any disclaimer, the term of this patent is extended or adjusted under 35 U.S.C. 154(b) by 347 days.

(21) Appl. No.: 17/670,306

(22) Filed: Feb. 11, 2022

(65) Prior Publication Data
US 2023/0137915 A1 May 4, 2023

(30) Foreign Application Priority Data

Oct. 29, 2021 (KR) .................. 10-2021-0147403
Jan. 27, 2022 (KR) .................. 10-2022-0012332

(51) Int. Cl.
*G06V 40/10* (2022.01)
*A63B 24/00* (2006.01)
(Continued)

(52) U.S. Cl.
CPC .......... *G06V 20/42* (2022.01); *A63B 24/0021* (2013.01); *A63B 24/0062* (2013.01);
(Continued)

(58) Field of Classification Search
CPC ............ G06V 20/42; G06V 40/10; G06T 2207/30221
See application file for complete search history.

(56) References Cited

U.S. PATENT DOCUMENTS

2003/0083117 A1* 5/2003 Rupert .................. A63F 13/812
463/4
2014/0364976 A1* 12/2014 Wohl ....................... A41D 1/04
700/91

(Continued)

FOREIGN PATENT DOCUMENTS

| EP | 3882832 A1 | 9/2021 |
| JP | 2020-430 A | 1/2020 |

(Continued)

OTHER PUBLICATIONS

Bialkowski, Alina, et al. "Large-scale analysis of soccer matches using spatiotemporal tracking data." 2014 IEEE international conference on data mining. IEEE, 2014. (Year: 2014).*

(Continued)

*Primary Examiner* — Michael Robert Cammarata
(74) *Attorney, Agent, or Firm* — BROADVIEW IP LAW, PC

(57) ABSTRACT

A method of providing tactical information for team sports is disclosed. The method includes acquiring a plurality of player tracking data sets for a plurality of players, acquiring role assignment information using the plurality of player tracking data sets, determining a dominant role assignment based on the plurality of role assignments, determining at least one irregular role assignment from the plurality of role assignments in consideration of the dominant role assignment, acquiring a plurality of space information sets associated with the target period for each of the plurality of role indices based on the remaining role assignment information other than the at least one irregular role assignment and some of the player tracking data sets corresponding to the remaining role assignment information and updating the role assignment information using the plurality of space information sets.

10 Claims, 49 Drawing Sheets

(51) Int. Cl.
*G06T 7/10* (2017.01)
*G06V 20/00* (2022.01)
*G06V 20/40* (2022.01)
*G06V 20/52* (2022.01)
*G16H 20/30* (2018.01)

(52) U.S. Cl.
CPC ............... *G06T 7/10* (2017.01); *G06V 20/35* (2022.01); *G06V 20/46* (2022.01); *G06V 20/52* (2022.01); *G06V 40/10* (2022.01); *G16H 20/30* (2018.01); *A63B 2024/0056* (2013.01); *A63B 2024/0071* (2013.01); *G06T 2207/10016* (2013.01); *G06T 2207/20084* (2013.01); *G06T 2207/30221* (2013.01)

(56) References Cited

U.S. PATENT DOCUMENTS

| | | | | |
|---|---|---|---|---|
| 2015/0142716 A1* | 5/2015 | Lucey | .................... | G06V 20/00 706/46 |
| 2016/0092769 A1* | 3/2016 | Lucey | ..................... | G06N 7/01 706/47 |
| 2016/0260015 A1* | 9/2016 | Lucey | ................. | G06F 3/04842 |
| 2021/0291018 A1* | 9/2021 | Yoon | ................. | A63B 24/0062 |
| 2022/0254036 A1* | 8/2022 | Seidl | ....................... | G06V 20/46 |

FOREIGN PATENT DOCUMENTS

| | | |
|---|---|---|
| KR | 10-0986647 B1 | 10/2010 |
| KR | 10-1938364 B1 | 4/2019 |
| KR | 10-2021-0117991 A | 9/2021 |
| WO | 2021/016901 A1 | 2/2021 |
| WO | WO-2021158771 A1 * | 8/2021 ............. G06N 20/00 |

OTHER PUBLICATIONS

Lucey, Patrick, et al. "Representing and discovering adversarial team behaviors using player roles." Proceedings of the IEEE Conference on Computer Vision and Pattern Recognition. 2013. (Year: 2013).*

Y. Wu et al., "ForVizor: Visualizing Spatio-Temporal Team Formations in Soccer," in IEEE Transactions on Visualization and Computer Graphics, vol. 25, No. 1, pp. 65-75, Jan. 2019, doi: 10.1109/TVCG.2018.2865041. (Year: 2019).*

A. Bialkowski, P. Lucey, P. Carr, I. Matthews, S. Sridharan and C. Fookes, "Discovering Team Structures in Soccer from Spatiotemporal Data," in IEEE Transactions on Knowledge and Data Engineering, vol. 28, No. 10, pp. 2596-2605, Oct. 1, 2016, doi: 10.1109/TKDE.2016.2581158. (Year: 2016).*

Wei, Xinyu, et al. "Large-scale analysis of formations in soccer." 2013 international conference on digital image computing: techniques and applications (DICTA). IEEE, 2013. (Year: 2013).*

Extended European Search Report for EP22163479 by European Patent Office dated Sep. 12, 2022.

Hyunsung Kim et al: "6MapNet: Representing soccer players from tracking data by a triplet network", arxiv.org, Cornell University Library, 201 Olin Library Cornell University Ithaca, NY 14853, Sep. 10, 2021.

Office Action for KR 10-2021-0147403 by Korean Intellectual Property Office dated Mar. 5, 2024.

Office Action for KR 10-2022-0012332 by Korean Intellectual Property Office dated Dec. 26, 2023.

International Search Report for PCT/KR2022/002152 by Korean Intellectual Property Office dated May 2, 2023.

Ryoo, Miohk et al. "Soccer game visual analysis based on player motion data." DBpia. Extended Abstracts of HCI Korea 2016.

Kim, Yunhu. "Analysis of Football Tactics and Formation Patterns Based on Big Data Analysis." Graduate School of Chung-Ang University. Department of Computer Science and Engineering. Feb. 2020.

Hoseung Song et al., Asymptotic distribution-free change-point detection for data with repeated observations, Sep. 29, 2021.

Takuma Narizukay et al., Characterization of the formation structure in team sports, Feb. 2018.

Takuma Narizuka et al., Clustering algorithm for formations in football games, Mar. 2019.

Alina Bialkowski et al., Large-Scale Analysis of Soccer Matches using Spatiotemporal Tracking Data, Dec. 2014.

* cited by examiner

FIG. 21

| Time stamp | Player 1 | Player 2 | Player 3 | ... | Player 10 |
|---|---|---|---|---|---|
| 0.1 | Role A | Role B | Role C | ... | Role J |
| 0.2 | Role A | Role B | Role C | ... | Role J |
| ... | Role A | Role B | Role C | ... | Role J |
| 7,199.9 | Role A | Role B | Role C | ... | Role J |
| 7,200.0 | Role A | Role B | Role C | ... | Role J |

FIG. 25

| Time stamp | Player 1 | Player 2 | ... |
|---|---|---|---|
| 0.1 | Role A | Role B | ... |
| 0.2 | Role A | Role B | ... |
| ... | ... | ... | ... |
| 123.4 | Role B | Role A | ... |
| ... | ... | ... | ... |
| 7,200.0 | Role A | Role B | ... |

| Time stamp | Player 1 | Player 2 | Player 3 | Player 4 | Player 5 | Player 6 | Player 7 | Player 8 | Player 9 | Player 10 |
|---|---|---|---|---|---|---|---|---|---|---|
| 0.1 | Role A | Role B | Role C | Role D | Role E | Role F | Role G | Role H | Role I | Role J |
| 0.2 | Role A | Role B | Role C | Role D | Role E | Role F | Role G | Role H | Role I | Role J |
| ... | Role A | Role B | Role C | Role D | Role E | Role F | Role G | Role H | Role I | Role J |
| 123.3 | Role A | Role B | Role C | Role D | Role E | Role F | Role G | Role H | Role I | Role J |
| 123.4 | Role B | Role A | Role C | Role D | Role E | Role F | Role G | Role H | Role I | Role J |
| ... | Role B | Role A | Role C | Role D | Role E | Role F | Role G | Role H | Role I | Role J |
| 873.5 | Role B | Role A | Role C | Role D | Role E | Role F | Role G | Role H | Role I | Role J |
| 873.6 | Role A | Role B | Role C | Role D | Role E | Role F | Role G | Role H | Role I | Role J |
| ... | Role A | Role B | Role C | Role D | Role E | Role F | Role G | Role H | Role I | Role J |
| 7,200.0 | Role A | Role B | Role C | Role D | Role E | Role F | Role G | Role H | Role I | Role J |

FIG. 29

| Time stamp | Player 1 | Player 2 | Player 3 | Player 4 | Player 5 | Player 6 | Player 7 | Player 8 | Player 9 | Player 10 |
|---|---|---|---|---|---|---|---|---|---|---|
| 0.1 | Role A | Role B | Role C | Role D | Role E | Role F | Role G | Role H | Role I | Role J |
| 0.2 | Role A | Role B | Role C | Role D | Role E | Role F | Role G | Role H | Role I | Role J |
| ... | Role A | Role B | Role C | Role D | Role E | Role F | Role G | Role H | Role I | Role J |
| 123.3 | Role A | Role B | Role C | Role D | Role E | Role F | Role G | Role H | Role I | Role J |
| 123.4 | Role B | Role A | Role C | Role D | Role E | Role F | Role G | Role H | Role I | Role J |
| ... | Role B | Role A | Role C | Role D | Role E | Role F | Role G | Role H | Role I | Role J |
| 873.5 | Role B | Role A | Role C | Role D | Role E | Role F | Role G | Role H | Role I | Role J |
| 873.6 | Role A | Role B | Role C | Role D | Role E | Role F | Role G | Role H | Role I | Role J |
| ... | Role A | Role B | Role C | Role D | Role E | Role F | Role G | Role H | Role I | Role J |
| 3,345.4 | Role A | Role B | Role C | Role D | Role E | Role F | Role G | Role H | Role I | Role J |
| 3,345.5 | Role D | Role E | Role A | Role C | Role B | Role F | Role H | Role C | Role A | Role G |
| 3,455.6 | Role E | Role D | Role J | Role F | Role J | Role D | Role B | Role G | Role H | Role I |
| 3,455.7 | Role A | Role C | Role A | Role H | Role E | Role E | Role B | Role D | Role E | Role G |
| ... | ... | ... | ... | ... | ... | ... | ... | ... | ... | ... |
| 3,712.3 | Role B | Role F | Role G | Role H | Role J | Role E | Role D | Role A | Role C | Role I |
| 3,712.4 | Role A | Role B | Role C | Role D | Role E | Role F | Role G | Role H | Role I | ... |
| ... | ... | ... | ... | ... | ... | ... | ... | ... | ... | ... |
| 7,200.0 | Role A | Role B | Role C | Role D | Role E | Role F | Role G | Role H | Role I | Role J |

FIG. 30

| Frame Number | 1-A | 2-B | 3-C | 4-D | 5-E | 6-F | 7-G | 8-H | 9-I | 10-J | Switch rate |
|---|---|---|---|---|---|---|---|---|---|---|---|
| 1 | 0 | 0 | 0 | 0 | 0 | 0 | 0 | 0 | 0 | 0 | 0 |
| 2 | 0 | 0 | 0 | 0 | 0 | 0 | 0 | 0 | 0 | 0 | 0 |
| ... | | | | | | | | | | | |
| 1,233 | 0 | 0 | 0 | 0 | 0 | 0 | 0 | 0 | 0 | 0 | 0 |
| 1,234 | 1 | 1 | 0 | 0 | 0 | 0 | 0 | 0 | 0 | 0 | 20% |
| ... | | | | | | | | | | | |
| 8,735 | 1 | 1 | 0 | 0 | 0 | 0 | 0 | 0 | 0 | 0 | 20% |
| 8,736 | 0 | 1 | 0 | 0 | 0 | 0 | 0 | 0 | 0 | 0 | 20% |
| ... | | | | | | | | | | | |
| 33,454 | 0 | 0 | 0 | 0 | 0 | 0 | 0 | 0 | 0 | 0 | 0 |
| 33,455 | 1 | 1 | 1 | 1 | 1 | 0 | 1 | 1 | 1 | 0 | 80% |
| 34,556 | 1 | 1 | 1 | 1 | 1 | 0 | 1 | 1 | 1 | 0 | 80% |
| 34,557 | 0 | 1 | 1 | 1 | 0 | 1 | 1 | 1 | 0 | 1 | 70% |
| ... | ... | ... | ... | ... | ... | ... | ... | ... | ... | ... | ... |
| 37,323 | 1 | 1 | 1 | 1 | 1 | 1 | 1 | 1 | 1 | 1 | 100% |
| 37,324 | 0 | 0 | 0 | 0 | 0 | 0 | 0 | 0 | 0 | 0 | 0 |
| ... | ... | ... | ... | ... | ... | ... | ... | ... | ... | ... | ... |
| 72,800 | 0 | 0 | 0 | 0 | 0 | 0 | 0 | 0 | 0 | 0 | 0 |

FIG. 39

| for specific frame | Role A | Role B | Role C | Role D | Role E | Role F | ... |
|---|---|---|---|---|---|---|---|
| Role A | -(0) | 1 | 1 | 0 | 0 | 0 | ... |
| Role B | 1 | -(0) | 1 | 1 | 0 | 0 | ... |
| Role C | 1 | 1 | -(0) | 1 | 1 | 0 | ... |
| Role D | 0 | 1 | 1 | -(0) | 1 | 1 | ... |
| Role E | 0 | 0 | 1 | 1 | -(0) | 1 | ... |
| Role F | 0 | 0 | 0 | 1 | 1 | -(0) | ... |
| ... | ... | ... | ... | ... | ... | ... | -(0) |

If connected = 1, else = 0 (including self to self)

FIG. 42

| Frame Number | Role A | Role B | Role C | Role D | Role E | Role F | Label (Class value) | Information (formation) |
|---|---|---|---|---|---|---|---|---|
| 1 | (x_a1, y_a1) | (x_b1, y_b1) | (x_c1, y_c1) | (x_d1, y_d1) | (x_d1, y_d1) | (x_d1, y_d1) | 1 | 3-5-2 |
| 2 | (x_a2, y_a2) | (x_b2, y_b2) | (x_c2, y_c2) | (x_d2, y_d2) | (x_d2, y_d2) | (x_d2, y_d2) | 2 | 4-4-2 |
| ... | ... | ... | ... | ... | ... | ... | ... | ... |
| 72,000 | (x_a72000, y_a72000) | (x_b72000, y_b72000) | (x_c72000, y_c72000) | (x_d72000, y_d72000) | (x_d72000, y_d72000) | (x_d72000, y_d72000) | 1 | 3-5-2 |

ANN input feature: 4210
ANN result label: 4220 (Label), 4230 (Information)

FIG. 46

| Time stamp | Player 1 | Player 2 | Player 3 | Player 4 | Player 5 | Player 6 | Player 7 | Player 8 | Player 9 | Player 10 | Distance |
|---|---|---|---|---|---|---|---|---|---|---|---|
| 2,103.0 | Role A | Role B | Role C | Role D | Role E | Role F | Role G | Role H | Role I | Role J | 0 |
| 2,103.1 | Role A | Role B | Role C | Role D | Role E | Role F | Role G | Role H | Role I | Role J | 0 |
| ... | ... | ... | ... | ... | ... | ... | ... | ... | ... | ... | ... |
| 3,044.1 | Role A | Role B | Role C | Role D | Role E | Role F | Role G | Role H | Role I | Role J | 0 |
| 3,044.2 | Role B | Role A | Role C | Role D | Role E | Role F | Role G | Role H | Role I | Role J | 2 |
| 3,044.3 | Role A | Role B | Role C | Role D | Role E | Role F | Role G | Role J | Role H | Role I | 5 |
| 873.5 | | | | | | | | | | | 3 |
| ... | ... | ... | ... | ... | ... | ... | ... | ... | ... | ... | ... |
| 4,900.0 | Role A | Role B | Role C | Role D | Role E | Role F | Role G | Role H | Role I | Role J | |

4610

METHOD FOR PROVIDING TACTICAL INFORMATION RELATED TO TEAM SPORTS

CROSS-REFERENCE TO RELATED APPLICATION

This application claims priority to and the benefit of Korean Patent Application No. 10-2022-0012332, filed on Jan. 27, 2022, and Korean Patent Application No. 10-2021-0147403, filed on Oct. 29, 2021, in the Korean Intelletual Property Office, the disclosure of which are incorporated herein by reference in their entirety.

BACKGROUND

1. Field of the Invention

The present disclosure generally relates to the field of sports analysis, and more specifically, to a technique for providing tactical information by analyzing a tactical change in team formation and role in team sports.

2. Discussion of Related Art

In modern team sports, training is largely divided into physical training and tactical training. While physical training aims to improve a player's basic physical abilities, such as muscular strength, endurance, and agility, tactical training aims to improve performance on tactics to obtain global or local benefits during a game.

In tactical training, practical exercises for mastering local tactics performed by a small group, responses in specific situations such as set-pieces, and overall strategies for team formation are important, but tactical analysis and review for improving team-level understanding is also an important factor.

Team formations and player positions are the most basic elements in tactical analysis, and are essential for higher-dimensional tactical analysis. However, from the perspective of sports analysis, team sports, and especially fluid sports such as soccer and basketball where players interact in real time, have high-dimensional characteristics that change very fluidly, and therefore modern sports teams still rely entirely on the intuition of people such as video analysts to analyze formations or positions.

SUMMARY OF THE INVENTION

An object of the present disclosure is to provide a method of providing tactical information for team sports to perform tactical analysis on a team sport from player tracking data.

An object of the present disclosure is to provide a method of providing tactical information for team sports to provide information on a team formation and/or a player position.

An object of the present disclosure is to provide a method of performing a high-dimensional tactical analysis using information on a team formation and/or a player position.

An object of the present disclosure is to provide a method of providing tactical information for team sports to acquire space information including a sequence of location data of a plurality of roles in a team sport from player tracking data.

An object of the present disclosure is to provide a method of providing tactical information for team sports to divide a target session for a game of a team sport into a plurality of formation periods with respect to a time point at which the formation of a team participating in the team sport changes.

An object of the present disclosure is to provide a method of providing tactical information for team sports to identify the formation of a team participating in a team sport or roles constituting the formation of the corresponding team.

An object of the present disclosure is to provide a method of providing tactical information for team sports to automatically match a location information acquisition device randomly assigned to a player participating in a team sport with a player identifier.

An object of the present disclosure is to provide a method of providing tactical information for team sports to divide a target period into a plurality of role periods with respect to time points at which the intended roles of at least some players of a team participating in a team sport change.

An object of the present disclosure is to provide a method of providing tactical information for team sports to detect irregular situations using assignment information for a plurality of roles generated from player tracking data.

An object of the present disclosure is to provide a method of providing tactical information for team sports to determine information about a playstyle of a team or player participating in a team sport using assignment information for a plurality of roles generated from player tracking data.

An object of the present disclosure is to provide a method of automatically extracting a highlight video from a game video of a team sport by using information about an irregular situation or a switch play.

However, the objects to be achieved by the present disclosure are not limited thereto and may be variously expanded without departing from the spirit and scope of the present disclosure.

According to an aspect of the present disclosure, there may be provided a method of providing tactical analysis for team sports, the method including operations of acquiring a plurality of player tracking data sets for a plurality of players, wherein each of the player tracking data sets includes locations of a corresponding player at a plurality of time points in a target session; acquiring a plurality of location distributions for the plurality of players, wherein each of the location distributions is generated based on a corresponding player tracking data set; assigning a plurality of role identifiers to the plurality of location distributions; acquiring a plurality of player-role assignments for the plurality of time points, wherein each of the assignments reflects a relationship between the plurality of players and the plurality of role identifiers at a first corresponding time point and is generated by assigning the plurality of role identifiers to the plurality of players based on the locations of the plurality of players at the first corresponding time point among the plurality of location distributions and the plurality of player tracking data sets; acquiring a plurality of role arrangements for the plurality of time points, wherein each of the role arrangements reflects a location relationship between the plurality of role identifiers at a second corresponding time point and is generated based on the player-role assignment at the second corresponding time point and the locations of the plurality of players at the second time points; and dividing a sequence of the plurality of role arrangements into at least two role arrangement groups using a change point detection algorithm.

According to another aspect of the present disclosure, there may be provided a method of providing tactical analysis for team sports, the method including operations of acquiring a plurality of player tracking data sets for a plurality of players, wherein each of the player tracking data sets includes locations of a corresponding player at a plurality of time points in a target session; acquiring a plurality of location distributions for the plurality of players, wherein each of the location distributions is generated based on a corresponding player tracking data set; assigning a plurality of role identifiers to the plurality of location distributions; acquiring a plurality of player-role assignments for the plurality of time points, wherein each of the assignments reflects a relationship between the plurality of players and the plurality of role identifiers at a first corresponding time point and is generated by assigning the plurality of role identifiers to the plurality of players based on the locations of the plurality of players at the first corresponding time point among the plurality of location distributions and the plurality of player tracking data sets; and acquiring a dominant player-role assignment from the plurality of player-role assignments.

According to another aspect of the present disclosure, there may be provided a method of providing tactical information for team sports, the method including operations of acquiring a plurality of player tracking data sets for a plurality of players, wherein each of the player tracking data sets includes a sequence of location data of a corresponding player during a target period; acquiring role assignment information using the plurality of player tracking data sets, wherein the role assignment information includes a plurality of role assignments for a plurality of time points in the target period and each of the role assignments indicates a plurality of role indices assigned to the plurality of players at a corresponding time point; determining a dominant role assignment based on the plurality of role assignments; determining at least one irregular role assignment from the plurality of role assignments in consideration of the dominant role assignment; acquiring a plurality of space information sets associated with the target period for each of the plurality of role indices based on the remaining role assignment information other than the at least one irregular role assignment and some of the player tracking data sets corresponding to the remaining role assignment information; and updating the role assignment information using the plurality of space information sets.

According to another aspect of the present disclosure, there may be provided a method of providing tactical information for team sports, the method including operations of acquiring a plurality of player tracking data sets for a plurality of players, wherein each of the player tracking data sets includes a sequence of location data of a corresponding player during a target session; detecting a change point reflecting a time point at which the formation of a team participating in the target session changes by applying a change point detection algorithm to feature values for the plurality of time points generated based on the plurality of player tracking data sets; and dividing the target session into at least two time periods based on the change point, wherein the at least two time periods include a first time period in which the formation of the team participating in the target session is a first team formation and a second time period in which the formation of the team participating in the target session is a second team formation.

According to another aspect of the present disclosure, there may be provided a method of providing tactical information for team sports, the method including operations of acquiring a plurality of player tracking data sets for a plurality of players, wherein each of the player tracking data sets includes a sequence of location data of a corresponding player during a target session; and identifying the formation of a team participating in a team sport game during the target session based on a formation structure for the target session based on the plurality of player tracking data sets, wherein the formation structure reflects information for determining the formation of the team.

According to another aspect of the present disclosure, there may be provided a method of providing tactical information for team sports, the method including operations of acquiring a plurality of space information sets associated with a target period for a plurality of roles based on a plurality of player tracking data sets for a plurality of players, wherein each of the player tracking data sets includes a sequence of location data of a corresponding player during the target period, and wherein each of the space information sets includes a sequence of location data of a corresponding role during the target period; acquiring role space arrangement information, wherein the role space arrangement information includes a plurality of role space arrangements for a plurality of time points in the target period, and wherein each role space arrangement reflects a location relationship between the plurality of roles at a first corresponding time point; acquiring a formation structure for the target period based on the plurality of role space arrangements, wherein the formation structure reflects information for determining the formation of a team participating in a team sport game during the target period; and determining the formation of the team based on the formation structure.

According to another aspect of the present disclosure, there may be provided a method of providing tactical information for team sports, the method including operations of acquiring a plurality of player tracking data sets for a plurality of players, wherein each of the player tracking data sets includes a sequence of location data of a corresponding player during a target period; detecting a change point reflecting a time point at which the roles of at least some of the plurality of players change within the target period by applying a change point detection algorithm to feature values for a plurality of time points generated based on the plurality of player tracking data sets; and dividing the target period into at least two time periods based on the change point, wherein the at least two time periods include a first role time period before the change point and a second role time period after the change point.

According to another aspect of the present disclosure, there may be provided a method of providing tactical information for team sports, the method including operations of acquiring a plurality of player tracking data sets for a plurality of players, wherein each of the player tracking data sets includes a sequence of location data of a corresponding player during a target period; acquiring role assignment information using the plurality of player tracking data sets, wherein the role assignment information includes a plurality of role assignments for a plurality of time points in the target period and each of the role assignments indicates a plurality of role indices assigned to the plurality of players at a corresponding time point; and detecting an irregular situation in the target period based on the plurality of role assignments, wherein the difference between a dominant role assignment and a role assignment of a time point corresponding to the irregular situation is greater than or equal to a predetermined threshold value.

According to another aspect of the present disclosure, there may be provided a method of providing tactical information for team sports, the method including operations of acquiring a plurality of player tracking data sets for a plurality of players, wherein each of the player tracking data sets includes a sequence of location data of a corresponding player during a target period; acquiring role assignment information using the plurality of player tracking data sets, wherein the role assignment information includes a plurality of role assignments for a plurality of time points in the target period and each of the role assignments indicates a plurality of role indices assigned to the plurality of players at a corresponding time point; and generating information on a playstyle of at least one team or at least one player participating in a team sport game based on the plurality of role assignments.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which:

FIG. 21 is an example of an initial role assignment table based on player tracking data.

FIG. 25 shows an example of a changed role at the time of a role assignment change.

FIG. 26 is an example of the entire role assignment including a role assignment change section.

FIG. 29 is an example of a role assignment table for determining an irregular role assignment.

FIG. 30 is an example of switch ratio determination according to the role assignment table of FIG. 29.

FIG. 39 is an example of a role adjacency matrix indicating a location relationship between roles.

FIG. 42 illustrates an example label of training data for artificial neural network-based formation identification according to an embodiment of the present disclosure.

FIG. 46 is an exemplary diagram showing the acquisition of a sequence of the distances between role assignments at adjacent frames for role period division.

DETAILED DESCRIPTION OF EXEMPLARY EMBODIMENTS

Figure 1:
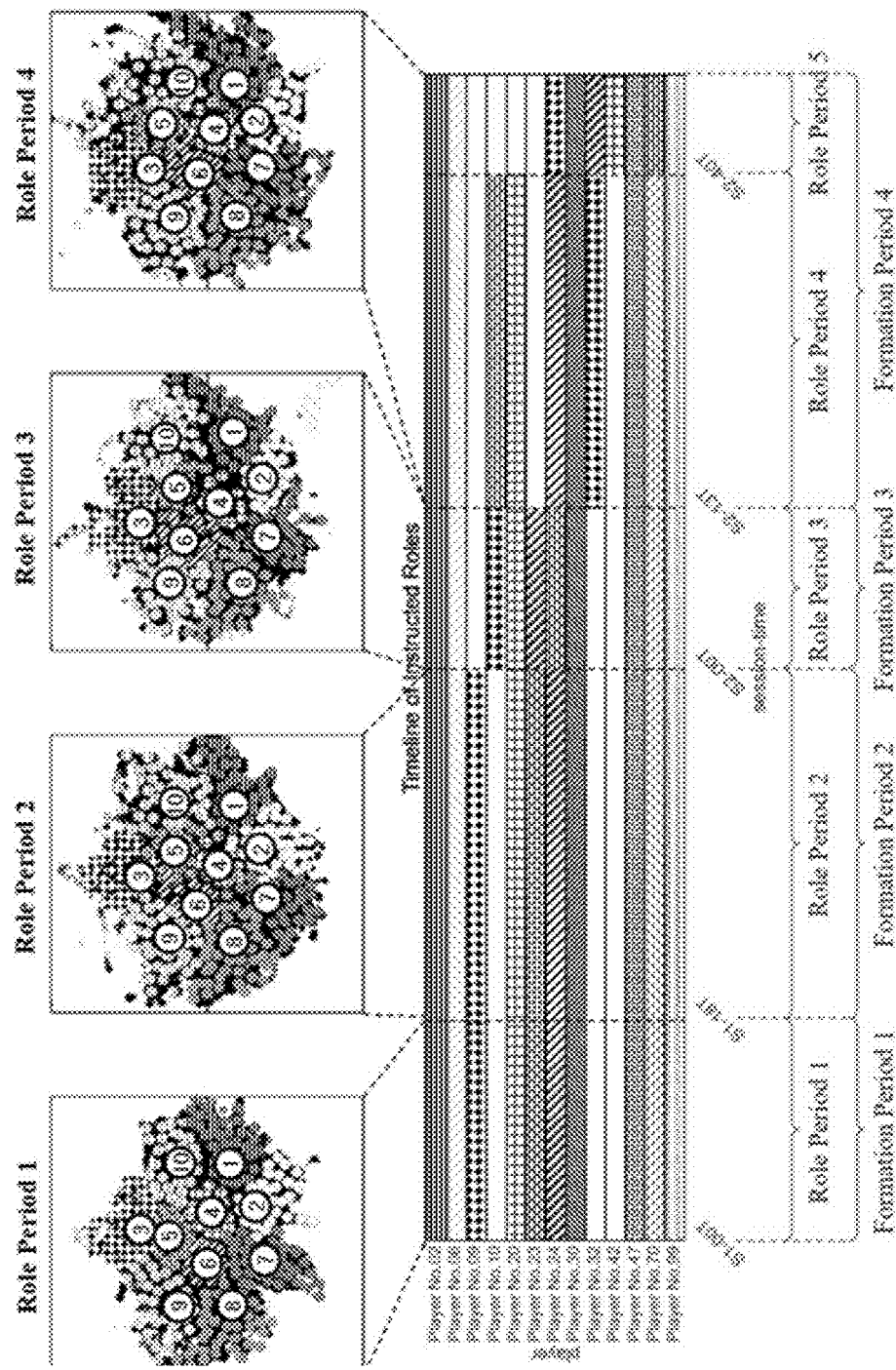
FIG. 1 is an example of a timeline of a change in formation and role according to a result of Sports Change-Point Detection (SportsCPD) according to an embodiment of the present disclosure.

Embodiments described in the present disclosure are intended to clearly explain the spirit of the invention to those skilled in the art. Therefore, the present disclosure is not limited by the embodiments, and the scope of the present invention should be interpreted as encompassing modifications and variations without departing from the spirit of the invention.

The terms used herein are selected from among general terms currently in wide use in the technical field to which the present invention pertains when possible and may have meanings varying depending on intentions of those skilled in the art, customs in the field of art, the emergence of new technologies, or the like. However, when a specific term is defined and used in a specific sense, the meaning of the term will be described separately. Accordingly, the terms used herein should be interpreted based on the actual meanings and the whole context throughout the specification rather than based on the names.

The accompanying drawings in the present disclosure are intended to easily explain the present invention, and shapes shown in the drawings may be exaggerated or reduced as necessary in order to aid in understanding the present invention, and the present invention is not limited by the drawings.

When it is determined that detailed descriptions of well-known elements or functions related to the present invention may obscure the subject matter of the present invention, detailed descriptions thereof will be omitted herein as necessary.

According to an aspect of the present disclosure, there may be provided a method of providing tactical analysis for team sports, the method including operations of acquiring a plurality of player tracking data sets for a plurality of players, wherein each of the player tracking data sets includes locations of a corresponding player at a plurality of time points in a target session; acquiring a plurality of location distributions for the plurality of players, wherein each of the location distributions is generated based on a corresponding player tracking data set; assigning a plurality of role identifiers to the plurality of location distributions; acquiring a plurality of player-role assignments for the plurality of time points, wherein each of the assignments reflects a relationship between the plurality of players and the plurality of role identifiers at a first corresponding time point and is generated by assigning the plurality of role identifiers to the plurality of players based on the locations of the plurality of players at the first corresponding time point among the plurality of location distributions and the plurality of player tracking data sets; acquiring a plurality of role arrangements for the plurality of time points, wherein each of the role arrangements reflects a location relationship between the plurality of role identifiers at a second corresponding time point and is generated based on the player-role assignment at the second corresponding time point and the locations of the plurality of players at the second time points; and dividing a sequence of the plurality of role arrangements into at least two role arrangement groups using a change point detection algorithm.

Here, the method may further include operations of acquiring a dominant player-role assignment from the plurality of player-role assignments; and determining at least one irregular player-role assignment among the plurality of player-role assignments based on the dominant player-role assignment, and the sequence of the plurality of role arrangements may include the plurality of role arrangements except the at least one irregular player-role assignment.

Here, the method may further include an operation of dividing the target session into at least two time periods corresponding to the at least two role arrangement groups, wherein the at least two time periods include a first time period in which the dominant formation of the team participating in the target session is a first team formation and a second time period in which the dominant formation of the team is a second team formation.

Here, the method may further include an operation of determining the first team formation from at least one first role arrangement for the first time period and the second team formation from at least one second role arrangement for the second time period.

According to another aspect of the present disclosure, there may be provided a method of providing tactical analysis for team sports, the method including operations of acquiring a plurality of player tracking data sets for a plurality of players, wherein each of the player tracking data sets includes locations of a corresponding player at a plurality of time points in a target session; acquiring a plurality of location distributions for the plurality of players, wherein each of the location distributions is generated based on a corresponding player tracking data set; assigning a plurality of role identifiers to the plurality of location distributions; acquiring a plurality of player-role assignments for the plurality of time points, wherein each of the assignments reflects a relationship between the plurality of players and the plurality of role identifiers at a first corresponding time point and is generated by assigning the plurality of role identifiers to the plurality of players based on the locations of the plurality of players at the first corresponding time point among the plurality of location distributions and the plurality of player tracking data sets; and acquiring a dominant player-role assignment from the plurality of player-role assignments.

Here, the dominant player-role assignment may be the most frequent player-role assignment among the plurality of player-role assignments.

Here, the method may further include an operation of determining a plurality of positions for the plurality of players based on the dominant player-role assignment.

Here, the method may further include an operation of selecting a secondary player-role assignment from among the plurality of player-role assignments.

Here, the secondary player-role assignment may be the second most frequent player-role assignment among the plurality of player-role assignments.

Here, the method may further include an operation of acquiring information on a position transition by comparing the dominant player-role assignment and the secondary player-role assignment.

Here, the method may further include an operation of acquiring switch ratio information on the plurality of player-role assignments based on the dominant player-role assignment.

Here, the method may further include an operation of detecting an irregular situation during the target session based on the switch ratio information.

A method of providing tactical information for team sports according to an aspect of the present disclosure may include operations of acquiring a plurality of player tracking data sets for a plurality of players, wherein each of the player tracking data sets includes a sequence of location data of a corresponding player during a target period; acquiring role assignment information using the plurality of player tracking data sets, wherein the role assignment information includes a plurality of role assignments for a plurality of time points within the target period and each of the role assignments indicates a plurality of role indices assigned to the plurality of players at a corresponding time point; determining a dominant role assignment based on the plurality of role assignments; determining at least one irregular role assignment from the plurality of role assignments in consideration of the dominant role assignment; acquiring a plurality of space information sets associated with the target period for each of the plurality of role indices based on the remaining role assignment information other than the at least one irregular role assignment and some of the player tracking data sets corresponding to the remaining role assignment information; and updating the role assignment information using the plurality of space information sets.

Here, the dominant role assignment may be the most frequent role assignment among the plurality of role assignments.

Here, the operation of determining at least one irregular role assignment may include operations of acquiring information on distances from the dominant role assignment to the plurality of role assignments, wherein the distances reflect a degree of difference between the dominant role assignment and the plurality of role assignments; and determining the irregular role assignment based on the information on the distances.

Here, the distances may reflect a switch ratio from the dominant role assignment with respect to the plurality of role assignments.

Here, the method may further include an operation of determining whether an additional update of the plurality of space information sets or the role assignment information is required.

Here, the operation of determining whether an additional update is required may include an operation of determining whether the additional update is required based on whether at least a portion of the role assignment information is changed by the operation of updating the role assignment information.

Here, the operation of determining whether an additional update is required may include an operation of determining whether the additional update is required based on whether a number of time points at which role assignments change is less than or equal to a predetermined threshold value by the operation of updating the role assignment information.

Here, the operation of determining whether an additional update is required may include an operation of determining whether the additional update is required based on whether a predetermined number of updates have been accomplished.

Here, the method may further include an operation of dividing a target session for one game of a team sport into at least two time periods, wherein the at least two time periods include a first time period and a second time period obtained through division based on a role change of at least some of the plurality of players or a formation change of a team participating in the game, wherein the target period is one of the first time period or the second time period.

According to an aspect of the present disclosure, there may be provided a device for providing tactical information for team sports, the device including a processor and a memory, wherein the processor may be configured to acquire a plurality of player tracking data sets for a plurality of players, wherein each of the player tracking data sets includes a sequence of location data of a corresponding player during a target period; acquire role assignment information using the plurality of player tracking data sets, wherein the role assignment information includes a plurality of role assignments for a plurality of time points in the target period and each of the role assignments indicates a plurality of role indices assigned to the plurality of players at a corresponding time point; determine a dominant role assignment based on the plurality of role assignments; determine at least one irregular role assignment from the plurality of role assignments in consideration of the dominant role assignment; acquire a plurality of space information sets associated with the target period for each of the plurality of role indices based on the remaining role assignment information other than the at least one irregular role assignment and some of the player tracking data sets corresponding to the remaining role assignment information; and update the role assignment information using the plurality of space information sets.

According to an aspect of the present disclosure, there may be provided a non-transitory computer-readable storage medium storing instructions executable by a processor, wherein the instructions are executed by the processor to cause the processor to acquire a plurality of player tracking data sets for a plurality of players, wherein each of the player tracking data sets includes a sequence of location data of a corresponding player during a target period; acquire role assignment information using the plurality of player tracking data sets, wherein the role assignment information includes a plurality of role assignments for a plurality of time points within the target period and each of the role assignments indicates a plurality of role indices assigned to the plurality of players at a corresponding time point; determine a dominant role assignment based on the plurality of role assignments; determine at least one irregular role assignment from the plurality of role assignments in consideration of the dominant role assignment; acquire a plurality of space information sets associated with the target period for each of the plurality of role indices based on the remaining role assignment information other than the at least one irregular role assignment and some of the player tracking data sets corresponding to the remaining role assignment information; and update the role assignment information using the plurality of space information sets.

According to an aspect of the present disclosure, there may be provided a method of providing tactical information for team sports, the method including operations of acquiring a plurality of player tracking data sets for a plurality of players, wherein each of the player tracking data sets includes a sequence of location data of a corresponding player during a target session; detecting a change point reflecting a time point at which the formation of a team participating in the target session changes by applying a change point detection algorithm to feature values for the plurality of time points generated based on the plurality of player tracking data sets; and dividing the target session into at least two time periods based on the change point, wherein the at least two time periods include a first time period in which the formation of the team participating in the target session is a first team formation and a second time period in which the formation of the team participating in the target session is a second team formation.

Here, the feature value for each of the plurality of time points may be generated based on at least one of the locations of the plurality of players at each time point, a player space arrangement reflecting a location relationship between the plurality of players at each time point, the locations of the plurality of roles at each time point, or a role space arrangement reflecting a location relationship between the plurality of roles at each time point.

Here, the operation of detecting a change point may include operations of acquiring role assignment information using the plurality of player tracking data sets, wherein the role assignment information includes a plurality of role assignments for a plurality of time points in the target session and each of the role assignments indicates a plurality of role indices assigned to the plurality of players at a first corresponding time point; acquiring a plurality of space information sets associated with the target session for each of the plurality of role indices based on the role assignment information and the player tracking data sets; and acquiring role space arrangement information including a plurality of role space arrangements for the plurality of time points, wherein each of the role space arrangements reflects a location relationship between the plurality of role indices at a second corresponding time point.

Here, the player space arrangement at each time point may include player adjacency information reflecting whether a first player among the plurality of players is adjacent to a second player among the plurality of players at each time point, and the role space arrangement of each time point may include role adjacency information reflecting whether a first role among the plurality of roles is adjacent to a second role among the plurality of roles at each time point.

Here, the player adjacency information includes a player adjacency matrix reflecting whether each of the plurality of players is adjacent to the others of the plurality of players, and the role adjacency information includes a role adjacency matrix reflecting whether each of the plurality of roles is adjacent to the others of the plurality of roles.

Here, the player adjacency matrix may be acquired by performing Delaunay triangulation on the plurality of players, and the role adjacency matrix may be acquired by performing Delaunay triangulation on the plurality of roles.

Here, the operation of detecting a change point may include operations of acquiring information on the distance between a feature value of a first time point and a feature value of a second time point among the feature values for the plurality of time points, wherein the distance reflects the degree of difference between the feature values; and applying the change point detection algorithm to the information on the distance.

Here, the information on the distance may include an inter-frame distance matrix reflecting the distances from each of the feature values of the plurality of time points to the others of the feature values of the plurality of time points.

Here, the information on the distance may include distances from a reference feature value at a reference time to each of the feature values of the plurality of time points.

Here, the information on the distance may include a sequence of time-series distances reflecting the distance between a feature value for the target time point and a feature value for a time point prior to the target time point, wherein the time-series distance is calculated at each of the plurality of time points.

Here, the change point detection algorithm may include a discrete g-segmentation algorithm.

Here, the method may further include an operation of determining whether the change point is valid based on the features of at least one division period.

Here, the operation of determining whether the change point is valid may include an operation of determining that the change point is valid in response to determining that the significance value of scan statics (Scan Statics p) corresponding to the change point is less than or equal to a first predetermined threshold value.

Here, the operation of determining that the change point is valid may include determining whether the change point is valid in response to determining that the time lengths of the first time period and the second time period are both greater than or equal to a second predetermined threshold value.

Here, the operation of determining whether the change point is valid may include determining that the change point is valid in response to determining that the difference between the average of feature values for a plurality of time points included in the first time period and the average of feature values for a plurality of time points included in the second time period is greater than or equal to a third predetermined threshold value.

According to an aspect of the present disclosure, there may be provided a device for providing tactical information for team sports, the device including a processor and a memory, wherein the processor may be configured to acquire a plurality of player tracking data sets for a plurality of players, wherein each of the player tracking data sets includes a sequence of location data of a corresponding player during a target session; detect a change point reflecting a time point at which the formation of a team participating in the target session is changed by applying a change point detection algorithm to feature values for the plurality of time points generated based on the plurality of player tracking data sets; and divide the target session into at least two time periods based on the change point, wherein the at least two time periods include a first time period in which the formation of the team participating in the target session is a first team formation and a second time period in which the formation of the team participating in the target session is a second team formation.

According to an aspect of the present disclosure, there may be provided a computer-readable storage medium storing instructions executable by a processor, wherein the instructions may be executed by the processor to cause the processor to acquire a plurality of player tracking data sets for a plurality of players, wherein each of the player tracking data sets includes a sequence of location data of a corresponding player during a target session; detect a change point reflecting a time point at which the formation of a team participating in the target session changes by applying a change point detection algorithm to feature values for the plurality of time points generated based on the plurality of player tracking data sets; and divide the target session into at least two time periods based on the change point, wherein the at least two time periods include a first time period in which the formation of the team participating in the target session is a first team formation and a second time period in which the formation of the team participating in the target session is a second team formation.

According to an aspect of the present disclosure, there may be provided a method of providing tactical information for team sports, the method including operations of acquiring a plurality of player tracking data sets for a plurality of players, wherein each of the player tracking data sets includes a sequence of location data of a corresponding player during a target session; and identifying the formation of a team participating in a team sport game during the target session based on a formation structure for the target session based on the plurality of player tracking data sets, wherein the formation structure reflects information for determining the formation of the team.

Here, the method may further include an operation of dividing the target session into at least two time periods, wherein the at least two time periods include a first time period and a second time period obtained through division based on a formation change of the team participating in the game, and the operation of identifying the formation may include operations of identifying a first formation of the team for the first time period based on a first formation structure for the first time period and identifying a second formation of the team for the second time period based on a second formation structure for the second time period.

Here, the operation of dividing the target session may include operations of detecting a change point reflecting a time point at which the formation of the team is changed in the target session by applying a change point detection algorithm to feature values for the plurality of time points generated based on the plurality of player tracking data sets; and dividing the target session into the at least two time periods based on the change point.

Here, the formation structure for the target session may be generated based on at least one of sequences of locations of each of the plurality of players during the target session, average locations of each of the plurality of players during the target session, a sequence of player space arrangements for the time points during the target session, each of the player space arrangements reflecting a location relationship between the plurality of players at each time point, and the average of player space arrangements for the time points during the target session.

Here, the formation structure for the target session may be generated based on at least one of sequences of locations of each of the plurality of roles during the target session, average locations of each of the plurality of roles during the target session, a sequence of role space arrangements for the time points during the target session, each of the role space arrangements reflecting a location relationship between the plurality of roles at each time point, and the average of role space arrangements for the time points during the target session.

Here, the operation of identifying the formation may include an operation of determining a formation identifier corresponding to the formation structure using an artificial neural network-based formation identification model, and the formation identification model may be generated by training an artificial neural network based on a plurality of training data sets, wherein each of the training data sets includes a formation structure sample and a labeled formation identifier corresponding to the formation structure sample.

Here, the formation structure sample may include a plurality of normalization data elements that are sorted by assigning a plurality of data elements included in the formation structure sample to a plurality of reference data elements included in the reference formation structure.

Here, the operation of identifying the formation may include an operation of acquiring a formation identifier corresponding to a first formation structure group among a plurality of formation structure groups by matching the formation structure to the first formation structure group, and the plurality of formation structure groups may be generated by clustering a plurality of formation structure samples and labeling each of the clusters with a formation structure identifier.

Here, each formation structure sample may include a plurality of normalization data elements that are sorted by assigning a plurality of data elements included in the formation structure sample to a plurality of reference data elements included in the reference formation structure.

Here, the method may further include operations of: acquiring formation data corresponding to the identified formation, wherein the formation data includes information on a plurality of positions for the formation and location characteristic values for the plurality of positions; acquiring player-position assignments for the plurality of players, wherein each assignment is generated by assigning the plurality of players to the plurality of positions based on the location characteristic values for the plurality of players and the location characteristic values for the plurality of positions.

Here, each location characteristic value may be generated based on at least one of a representative location of each player or each position or a location distribution for each player or each position.

Here, the method may include operations of acquiring participating-player information of the team participating in the target session, wherein the participating-player information includes a plurality of positions for the formation of the team and player identifiers corresponding to the plurality of positions; and matching the plurality of players to the plurality of player identifiers based on the player-position assignments.

Here, each player identifier may include at least one of a player name or a uniform number.

According to an aspect of the present disclosure, there may be provided a method of providing tactical information for team sports, the method including operations of acquiring a plurality of space information sets associated with a target period for a plurality of roles based on a plurality of player tracking data sets for a plurality of players, wherein each of the player tracking data sets includes a sequence of location data of a corresponding player during the target period, and wherein each of the space information sets includes a sequence of location data of a corresponding role during the target period; acquiring role space arrangement information, wherein the role space arrangement information includes a plurality of role space arrangements for a plurality of time points in the target period, and wherein each role space arrangement reflects a location relationship between the plurality of roles at a first corresponding time point; acquiring a formation structure for the target period based on the plurality of role space arrangements, wherein the formation structure reflects information for determining the formation of a team participating in a team sport game during the target period; and determining the formation of the team based on the formation structure.

Here, each of the role space arrangements may include role adjacency information reflecting whether a first role out of the plurality of roles is adjacent to a second role out of the plurality of roles at a first corresponding time point.

Here, the role adjacency information may include a role adjacency matrix reflecting whether each of the plurality of roles is adjacent to the others of the plurality of roles.

Here, the role adjacency matrix may be acquired by performing Delaunay triangulation on the plurality of roles.

Here, the formation structure may be a sequence of the plurality of role adjacency matrices for the plurality of time points.

Here, the formation structure may be an average role adjacency matrix reflecting the average of the plurality of role adjacency matrices for the plurality of time points.

According to an aspect of the present disclosure, there may be provided a method of providing tactical information for team sports, the method including operations of acquiring a plurality of player tracking data sets for a plurality of players, wherein each of the player tracking data sets includes a sequence of location data of a corresponding player during a target period; detecting a change point reflecting a time point at which the roles of at least some of the plurality of players change within the target period by applying a change point detection algorithm to feature values for a plurality of time points generated based on the plurality of player tracking data sets; and dividing the target period into at least two time periods based on the change point, wherein the at least two time periods include a first role time period before the change point and a second role time period after the change point.

Here, the feature value for each of the plurality of time points may include a role assignment for a corresponding time point, wherein the role assignment indicates a plurality of role indices assigned to the plurality of players at the corresponding time point.

Here, the operation of detecting a change point may further include an operation of acquiring role assignment information using the plurality of player tracking data sets, wherein the role assignment information includes a plurality of role assignments for the plurality of time points in the target period.

Here, the operation of detecting a change point may include operations of acquiring information on the distance between a feature value of a first time point and a feature value of a second time point among the feature values for the plurality of time points, wherein the distance reflects the degree of difference between the feature values; and applying the change point detection algorithm to the information on the distance.

Here, the distance between the first role assignment and the second role assignment may reflect the difference in the number of roles between the first role assignment and the second role assignment.

Here, the information on the distance may include an inter-frame distance matrix reflecting the distances from each of the feature values of the plurality of time points to the others of the feature values of the plurality of time points.

Here, the information on the distance may include a sequence of time-series distances reflecting the distance between a feature value for the target time point and a feature value for a time point prior to the target time point, wherein the time-series distance is calculated at each of the plurality of time points.

Here, the change point detection algorithm may include a discrete g-segmentation algorithm.

Here, the operation of detecting a change point may include an operation of detecting the change point based on the remaining role assignments other than at least one irregular role assignment among the plurality of role assignments for the plurality of time points.

Here, the irregular role assignment may be determined based on operations of determining a dominant role assignment based on the plurality of role assignments and determining at least one irregular role assignment from the plurality of role assignments in consideration of the dominant role assignment.

Here, the dominant role assignment may be the most frequent role assignment among the plurality of role assignments.

Here, the operation of determining at least one irregular role assignment may include operations of acquiring information on distances from the dominant role assignment to the plurality of role assignments, wherein the distances reflect a degree of difference between the dominant role assignment and the plurality of role assignments; and determining the irregular role assignment based on the information on the distances.

Here, the method may further include an operation of determining whether the change point is valid based on the features of at least one division period.

Here, the operation of determining whether the change point is valid may include an operation of determining that the change point is valid in response to determining that the significance value of scan statics (Scan Statics p) corresponding to the change point is less than or equal to a first predetermined threshold value.

Here, the operation of determining that the change point is valid may include determining whether the change point is valid in response to determining that the time lengths of the first role time period and the second role time period are both greater than or equal to a second predetermined threshold value.

Here, the method may further include an operation of dividing a target session for one game of a team sport into at least two formation time periods, wherein the at least two formation time periods include a first formation time period and a second formation time period obtained through division based on a formation change of a team participating in the game, wherein the target period may be one of the first formation time period or the second formation time period.

According to an aspect of the present disclosure, there may be provided a device for providing tactical information for team sports, the device including a processor and a memory, wherein the processor may be configured to acquire a plurality of player tracking data sets for a plurality of players, wherein each of the player tracking data sets includes a sequence of location data of a corresponding player during a target period; detect a change point reflecting a time point at which the roles of at least some of the plurality of players change within the target period by applying a change point detection algorithm to feature values for a plurality of time points generated based on the plurality of player tracking data sets; and divide the target period into at least two time periods based on the change point, wherein the at least two time periods include a first role time period before the change point and a second role time period after the change point.

According to an aspect of the present disclosure, there may be provided a computer-readable storage medium storing instructions executable by a processor, wherein the instructions are executed by the processor to cause the processor to acquire a plurality of player tracking data sets for a plurality of players, wherein each of the player tracking data sets includes a sequence of location data of a corresponding player during a target period; detect a change point reflecting a time point at which the roles of at least some of the plurality of players change within the target period by applying a change point detection algorithm to feature values for a plurality of time points generated based on the plurality of player tracking data sets; and divide the target period into at least two time periods based on the change point, wherein the at least two time periods include a first role time period before the change point and a second role time period after the change point.

According to an aspect of the present disclosure, there may be provided a method of providing tactical information for team sports, the method including operations of acquiring a plurality of player tracking data sets for a plurality of players, wherein each of the player tracking data sets includes a sequence of location data of a corresponding player during a target period; acquiring role assignment information using the plurality of player tracking data sets, wherein the role assignment information includes a plurality of role assignments for a plurality of time points in the target period and each of the role assignments indicates a plurality of role indices assigned to the plurality of players at a corresponding time point; and detecting an irregular situation in the target period based on the plurality of role assignments, wherein the difference between a dominant role assignment and a role assignment of a time point corresponding to the irregular situation is greater than or equal to a predetermined threshold value.

Here, the dominant role assignment may be the most frequent role assignment among the plurality of role assignments.

Here, the difference between the dominant role assignment and the role assignment of the time point corresponding to the irregular situation may reflect a switch ratio between the dominant role assignment and the role assignment of the time point corresponding to the irregular situation.

Here, the method may further include operations of acquiring full-time video data for the target period; and extracting highlight video data including video data for the time point corresponding to the irregular situation from the full-time video data.

Here, the method may further include an operation of dividing a target session for one game of a team sport into at least two role time periods, wherein the at least two role time periods include a first role time period and a second role time period obtained through division with respect to a time point at which the roles of at least some of the plurality of players change, wherein the target period may be one of the first role time period or the second role time period.

According to an aspect of the present disclosure, there may be provided a device for providing tactical information for team sports, the device including a processor and a memory, wherein the processor may be configured to acquire a plurality of player tracking data sets for a plurality of players, wherein each of the player tracking data sets includes a sequence of location data of a corresponding player during a target period; acquire role assignment information using the plurality of player tracking data sets, wherein the role assignment information includes a plurality of role assignments for a plurality of time points in the target period and each of the role assignments indicates a plurality of role indices assigned to the plurality of players at a corresponding time point; and detect an irregular situation in the target period based on the plurality of role assignments, wherein the difference between a dominant role assignment and a role assignment of a time point corresponding to the irregular situation is greater than or equal to a predetermined threshold value.

According to an aspect of the present disclosure, there may be provided a computer-readable storage medium storing instructions executable by a processor, wherein the instructions are executed by the processor to cause the processor to acquire a plurality of player tracking data sets for a plurality of players, wherein each of the player tracking data sets includes a sequence of location data of a corresponding player during a target period; acquire role assignment information using the plurality of player tracking data sets, wherein the role assignment information includes a plurality of role assignments for a plurality of time points in the target period and each of the role assignments indicates a plurality of role indices assigned to the plurality of players at a corresponding time point; and detect an irregular situation in the target period based on the plurality of role assignments, wherein the difference between a dominant role assignment and a role assignment of a time point corresponding to the irregular situation is greater than or equal to a predetermined threshold value.

According to an aspect of the present disclosure, there may be provided a method of providing tactical information for team sports, the method including operations of acquiring a plurality of player tracking data sets for a plurality of players, wherein each of the player tracking data sets includes a sequence of location data of a corresponding player during a target period; acquiring role assignment information using the plurality of player tracking data sets, wherein the role assignment information includes a plurality of role assignments for a plurality of time points in the target period and each of the role assignments indicates a plurality of role indices assigned to the plurality of players at a corresponding time point; and generating information on a playstyle of at least one team or at least one player participating in a team sport game based on the plurality of role assignments.

Here, the information on the playstyle may include at least one of information on the time length of a switch play reflecting a temporary role swap between at least some of the plurality of players, information on the number of switch plays, or information on roles in the switch play that has occurred.

Here, the operation of generating the information on the playstyle may further include operations of determining a dominant role assignment based on the plurality of role assignments; determining a secondary role assignment based on the plurality of role assignments; and acquiring information on the switch play by comparing the dominant role assignment and the secondary role assignment.

Here, the dominant role assignment may be the most frequent role assignment among the plurality of role assignments.

Here, the secondary role assignment may be the second most frequent role assignment among the plurality of role assignments.

Here, the switch play may include a first switch play reflecting a role swap between roles corresponding to a first role group and a second switch play reflecting a role swap between roles corresponding to a second role group. At least one of the plurality of time points may be reflected in both of the first switch play and the second switch play.

Here, the method may further include operations of acquiring full-time video data for the target period; and extracting highlight video data including video data for the time point corresponding to the switch play from the full-time video data.

Here, the method may further include an operation of dividing a target session for one game of a team sport into at least two role time periods, wherein the at least two role time periods include a first role time period and a second role time period obtained through division with respect to a time point at which the roles of at least some of the plurality of players change, wherein the target period may be one of the first role time period or the second role time period.

According to an aspect of the present disclosure, there may be provided a device for providing tactical information for team sports, the device including a processor and a memory, wherein the processor may be configured to acquire a plurality of player tracking data sets for a plurality of players, wherein each of the player tracking data sets includes a sequence of location data of a corresponding player during a target period; acquire role assignment information using the plurality of player tracking data sets, wherein the role assignment information includes a plurality of role assignments for a plurality of time points in the target period and each of the role assignments indicates a plurality of role indices assigned to the plurality of players at a corresponding time point; and generate information on a playstyle of at least one team or at least one player participating in a team sport game based on the plurality of role assignments.

According to an aspect of the present disclosure, there may be provided a computer-readable storage medium storing instructions executable by a processor, wherein the instructions are executed by the processor to cause the processor to acquire a plurality of player tracking data sets for a plurality of players, wherein each of the player tracking data sets includes a sequence of location data of a corresponding player during a target period; acquire role assignment information using the plurality of player tracking data sets, wherein the role assignment information includes a plurality of role assignments for a plurality of time points in the target period and each of the role assignments indicates a plurality of role indices assigned to the plurality of players at a corresponding time point; and generate information on a playstyle of at least one team or at least one player participating in a team sport game based on the plurality of role assignments.

1. Introduction

In fluid team sports such as soccer and basketball, analyzing team formation is one of the most intuitive methods for understanding tactics from the perspective of those engaged in the field. However, conventional approaches have limitations in that they do not sufficiently reflect actual game situations even if the team formation is assumed to be consistent throughout the game or is assigned on a scene-by-scene basis. Focusing on these problems, the present disclosure proposes Sports Change-Point Detection (SportsCPD), which is a change point detection framework that distinguishes changes in tactically intended formations and player positions from temporary changes during a game of a team sport using spatiotemporal tracking data.

Here, the term "player position" may be interpreted as referring to a role assigned to a player in a team sport (e.g., a center forward or central defender in the case of soccer), and the term "team formation" may be interpreted as referring to a combination of roles ("4-4-2" or "3-4-3" in soccer) assigned to all or most of the players (e.g., field players excluding a goalkeeper in soccer) in a team.

Also, here, an "intended change" is a change in team formation or player position that is wide-ranging and continuous according to the coach's instructions, etc. For example, a team that has applied a "4-4-2" formation in the first half of a soccer game may apply a "3-4-3" formation in the second half under the tactical judgment of its coaches. A "temporary change" is a change that occurs temporarily or arbitrarily. For example, a defender in a soccer game may overlappingly perform the role of an attacker for a short period of time.

The SportsCPD according to an embodiment of the present disclosure may detect a point at which a team formation changes (hereinafter referred to as a "formation change point"). Hereinafter, this is referred to as Formation Change-Point Detection (FormCPD). As an example, FormCPD may be performed by acquiring information reflecting roles assigned to players on a scene-by-scene basis first, acquiring information reflecting a location relationship between the roles, and then detecting a formation change point from a sequence of information on the location relationship between the roles.

Also, the SportsCPD according to an embodiment of the present disclosure may detect a point at which a player position, i.e., a role assigned to a player, changes (hereinafter referred to as a "role change point"). Hereinafter, this is referred to as Role Change-Point Detection (RoleCPD). As an example, RoleCPD may be performed by detecting a role change point from a sequence of information reflecting roles assigned to players.

Here, the information reflecting the roles assigned to the players may be referred to as "player-role assignment." For example, the player-role assignment can be represented as a role permutation, which will be described in more detail later.

Also, here, the information reflecting the location relationship between the roles may be referred to as a role arrangement. For example, the role arrangement can be represented as a role-adjacency matrix, which will be described in more detail later.

According to an example, the detection of the change point may be performed using a nonparametric change point detection technique. However, the change point detection technique is not limited thereto.

According to the results of evaluating the method according to an embodiment of the present disclosure using actual measurement data recorded by those engaged in the field, it was confirmed that the method according to an embodiment of the present disclosure can accurately detect a tactical change point and predict a formation of each segment. Also, in embodiments of the present disclosure, practical usage examples that can be interpreted and utilized by those engaged in the field will be mentioned.

2. Overview

In fluid team sports such as soccer or basketball, players interact with each other while maintaining roles in a particular formation. Therefore, analyzing a team formation is one of the most intuitive methods to understand tactics from the perspective of those engaged in the field. Since it is obvious that team formation has a significant effect on player location during a game, there have been previous studies in the field of sports science that have attempted to estimate team formation during a game using spatiotemporal tracking data.

However, the results according to the previous approaches were different from the formation changes in an actual game. Many approaches assume that the team formation is consistent throughout a game or session, and thus have a limitation in that they do not accurately reflect real situations in which coaches often change their team formations in response to various in-game situations during a match. Other approaches have considered formation changes, but have assigned formations on a scene-by-scene basis or on an attack/defense period basis. Using this assignment scheme, there is a problem in that a team formation changes too frequently, contrary to a coach's intention, given that coaches generally instruct only a few changes during a game.

In order to fill this gap, embodiments of the present disclosure propose a change point detection framework called SportsCPD, which distinguishes tactically intended formation and role changes from temporary changes in team sport games.

The SportsCPD may be exemplarily performed as follows.

First, roles are assigned to players on a scene-by-scene basis. As an example, the scene-by-scene role assignment to players may be performed as follows. The concept of role representation presented in Balkoski's paper "Large-scale analysis of soccer matches using spatiotemporal tracking data (2014)" was partially borrowed for the assignment of roles to players, which will be described later.

Player tracking data sets may be acquired. Each player tracking data set relates to an individual player's location and may include information about the corresponding player's location within a session to be analyzed (hereinafter referred to as a "target session").

Here, the player tracking data set may be, for example, acquired through a positioning sensor (e.g., a Global Positioning System (GPS) sensor or a local positioning system (LPS) sensor) worn by and/or attached to a player or through an image analysis for a sports video and may be represented according to a field coordinate system. The field coordinate system may be a coordinate system having a point of a stadium (e.g., a center or corner point of a stadium) as an origin and the length direction and width direction of the stadium as axes. Also, the player tracking data set may include locations in a time-series form, where the time section may be usually the same as the sampling section of a sensor or an image analysis, but this is not necessarily the case.

Roles may be assigned to players based on the player tracking data set. Here, the role assignment may be performed by assigning role identifiers to the players. First, on the assumption that players have constant roles over the entire session, the location distributions of the players during the session which are obtained from the player tracking data sets may be determined as initial location distributions of the roles. Then, it is possible to assign the roles to the players according to their locations, in consideration of the initial location distributions of the roles. As a simple example, roles may be assigned to individual players on a scene-by-scene basis such that the sum of the distances between the average location of the initial location distribution of the roles assigned to the players and the locations of the individual players in a corresponding scene is minimized. However, instead of simply minimizing the sum of distances, various techniques may be used. For example, a Hungarian algorithm such as a cost matrix based on log probability density may be used. Subsequently, the location distribution of the roles may be newly created in consideration of the roles assigned to the players on a scene-by-scene basis. Since it is assumed that a player has only one role over the entire session, the initial location distribution may be created from only locations related to one player over the entire session. On the other hand, the newly created location distribution may be created from the locations of different players on a scene-by-scene basis because players who perform a single role may differ from scene to scene. When the location distributions of roles are newly created, the roles may be assigned to the players in consideration of the locations of the players on a scene-by-scene basis in consideration of the location distributions again. Then, by repeating the above operation a sufficient number of times or repeating the above operation until the role assignment or location distribution converges sufficiently, the final player-role assignment may be acquired.

Meanwhile, the process of acquiring the above player-role assignment may be understood to be valid in a situation where players are performing specific positions in a team formation. Accordingly, irregular situations in which the team formation is disrupted, such as set-piece situations, may be treated as contaminated data in assigning roles. Accordingly, it is possible to improve the accuracy of player-role assignment by performing pre-processing to eliminate irregular situations from the scenes. Specifically, when an irregular situation is detected, player-role assignment may be performed excluding irregular situations. In detail, the location distribution of roles may be calculated using only player tracking data set of scenes other than scenes corresponding to irregular situations.

The detection of irregular situations may be accomplished in various ways.

As an example, an irregular situation is a situation in which the formation is broken, and since a significant number of irregular situations may occur during a set-piece, the irregular situations may be detected using characteristics occurring in the set-piece. In soccer, for example, in set-piece situations such as free kicks, corner kicks or penalty kicks, the location of the ball is temporarily fixed (and furthermore, in a corner kick or penalty kick situation, the fixed location is specified), and players have a relatively dense location relationship and have little or no movement. Therefore, when the location of the ball is fixed for a certain period of time or below a threshold value (in the case of a corner kick or penalty kick, a condition based on a specific location may be added), when players are stationary for a certain period of time or have movements below a threshold value (in the case of a corner kick or penalty kick, a condition based on a specific location may be added), and/or when players are densely distributed for a certain period of time (which may be, for example, determined as a case in which a predetermined number of players or more are in a predetermined radius or a case in which the sum of the distances between players is less than or equal to a predetermined distance), it may be determined that the scene corresponds to an irregular situation.

As another example, irregular situations may be detected based on the degree to which players deviate from their instructed roles. In detail, when roles are assigned to players on a scene-by-scene basis, a dominant player-role assignment may be determined. Here, the dominant player-role assignment is a role-assignment mainly used by a team within a target session, that is, it may be role-assignment according to an indicated team formation. The dominant player-role assignment may be determined based on the frequency from a scene-by-scene player-role assignment of the target session. For example, the most frequent player-role assignment may be determined as the dominant player-role assignment, given that one or only a few team formations indicated in team sports are over the target session. Alternatively, a predetermined number of player-role assignments in descending order of frequency may be determined as the dominant player-role assignments. Here, when a formation period, which will be described below, is determined, it may be preferable to assume that one dominant player-role assignment is present for each formation period, but it should be noted that it is not necessary to have only one dominant player-role assignment during the entire target session. When the dominant player-role assignment is determined, an irregular situation may be detected by comparing the dominant player-role assignment to the scene-by-scene player-role assignment. For example, when the player-role assignment is represented as a role permutation as described above, the distance between the role permutation of the dominant player-role assignment and the role permutation of the scene-by-scene player-role assignment is greater than or equal to a threshold value, it may be determined that the scene corresponds to an irregular situation. Also, when there are a plurality of dominant player-role assignments and the minimum distance between the dominant player-role assignment and the scene-by-scene player-role assignment is greater than or equal to a threshold value, it may be determined that the scene corresponds to an irregular situation.

As another example, given that the team formation abruptly breaks down in an irregular situation, a case in which a change in sequence of scene-by-scene player-role assignments is more than a certain level may be detected. In detail, a case in which the distance between permutations of adjacent player-role assignments is greater than or equal to a threshold value may be determined as an irregular situation.

When roles are assigned to players on a scene-by-scene basis, change point detection is performed in the following two steps. (1) A formation change point is detected for each session, and (2) for each segment obtained from the result, a role change point is detected. The steps will be described in detail below.

In the FormCPD step, a formation period may be determined in a target session by detecting a formation change point using a player-role assignment. Here, the formation period may be a period in which an instructed formation is constant. Also, a formation for each formation period may be identified.

As an example, in the FormCPD, a formation change point may be detected from a role arrangement.

Here, the role arrangement relates a location relationship between role identifiers and may be generated from the player-role assignments and the player tracking data set. Also, since the role arrangement may be generated on a scene-by-scene basis from the locations of the players in corresponding scenes extracted from the player tracking data set and the scene-by-scene player-role assignment, a sequence of role arrangements may be acquired for a target session.

As an example, the role assignment in a specific scene may be represented using coordinates between roles on a stadium coordinate system, and this may be generated by assigning, to the roles, location coordinates of players in the corresponding scene extracted from the player tracking data set through the player-role assignment in the corresponding scene.

As another example, the role arrangement may yield an adjacency relationship between roles. Here, the adjacency relationship relates to location adjacency between roles and may be referred to as a "role topology." In the role topology, a location relationship between roles may be determined based on adjacencies between roles according to contextual adjacency instead of practical values such as locations in a stadium or corresponding distances. For example, the role topology may be represented as a role-adjacency matrix calculated from a Delaunay triangulation with reference to the presentation of Narizukawa Yamazaki's paper "Characterization of the formation structure in team sports (2017)." A role adjacency matrix using this can be acquired as follows. First, locations of roles may be acquired on a scene-by-scene basis. In this case, the locations may be in accordance with a reference coordinate system. Next, a role adjacency matrix, which is a matrix for performing a Delaunay triangulation, i.e., a triangulation that allows the minimum values of all angles of a polygon to become the maximum on a polygon with vertices representing the roles and for defining roles sharing the triangle as adjacent roles and defining the other roles as non-adjacent roles according to relationships of the roles with respect to the other roles, may be acquired.

Next, considering that the role arrangement is time-series information provided in the form of a scene-by-scene sequence, a change point may be detected from a calculated role arrangement. In this case, it will be appreciated that various change point detection algorithms may be used. The change point detection algorithms may include an online change point detection algorithm that detects a change point from a sequence input in real time and an offline change point detection algorithm that detects a change point from a completed sequence. Examples of the online algorithm may include sequential hypothesis testing or streaming algorithms that detect change points in consideration of factors such as a false alarm rate, a misdetection rate, and a detection delay, and examples of the offline algorithm may include change-in-mean detection based on a hypothesis testing method, maximum likelihood estimation based on a time change, or two-phase regression. Therefore, in the present disclosure, change point detection should be understood as a comprehensive concept including any sequence segmentation or statistical analysis.

According to an example, a change point may be detected from a sequence of the role adjacency matrix. In this case, a nonparametric change point detection algorithm may be applied to detect a change point in consideration of the fact that, without limitation, the role adjacency matrix is high-dimensional data having repeated observations. For example, discrete g-segmentation may be used as the nonparametric algorithm. The discrete g-segmentation may be performed with reference to the presentation of Song and Chen's paper "Asymptotic distribution-free change-point detection for data with repeated observations (2020)."

The detected change point may divide the game into several formation periods in which a team formation is maintained in one formation period.

Also, in the FormCPD, a formation structure may be acquired for each of team formation periods, i.e., target session segments, and the formation of the corresponding segment may be identified from the formation structure. For example, the formation structure in each segment may be represented as an average role adjacency matrix during the corresponding segment. As another example, the formation structure in each segment may be represented as scene-by-scene location information (e.g., average location or location distribution) corresponding to the dominant player-role assignment during the corresponding segment. Also, the represented formation structure may be interpreted with the language of those engaged in the field (e.g., "4-4-2" or "3-4-3"). For example, through an artificial neural network trained with data obtained by clustering the average role adjacency matrices and labeling each cluster with a formation identifier or labeling the location information with a formation identifier, the formation structure represented for each segment may be interpreted as the formation identifier.

In the RoleCPD step, a change point may be detected in a formation period. In this case, it will be appreciated that the change point may be detected from a sequence of role permutations in the formation period and various change point detection algorithms described above may be used. For example, similar to the FormCPD, a role change point may be acquired by applying the discrete g-segmentation to the sequence of permutations with a pairwise Hamming distance. The role change points may cause each formation period to be divided into several role periods. Here, the role period may be a period in which the roles assigned to the players are maintained.

Also, in the RoleCPD step, in order to find players' actual positions (e.g., "center forward" or "right midfielder") for each role period, one dominant role may be assigned to each player for the corresponding role period.

Also, in the RoleCPD step, a position transition (transposition) of players may be calculated. Here, the position transposition may be derived from the role permutation in each formation period.

Meanwhile, the SportsCPD may be used to perform some high-dimensional tactical analyses.

According to an embodiment of the present disclosure, the SportsCPD may be used to analyze a switch pattern. Here, the switch may be the swapping of roles between players. The analysis of the switch pattern may be performed in consideration of a player-role assignment. More specifically and without limitation, the swapping of roles between players, i.e., the position transposition, may include only a temporary swapping of roles between players that occurs while the same formation is maintained, excluding the position transposition that occurs when the team formation changes. In this case, the analysis of the switch pattern may be performed in consideration of a player-role assignment in a formation period.

Specifically, the analysis of the switch pattern may be performed as follows.

As an example, first, a dominant player-role assignment and a secondary player-role assignment may be acquired in the formation period. Since the formation is fixed in one formation period, only one main player-role assignment can be determined. For example, the most frequent player-role assignment may be determined as the dominant player-role assignment among player-role assignments corresponding to the formation period. Next, the secondary player-role assignment may be determined. For example, the secondary player-role assignment may be determined according to whether the number of player-role assignments corresponding to the formation period except the dominant player-role assignment is less than or equal to a predetermined number in descending order of frequency, whether the frequency of the player-role assignment is greater than or equal to a predetermined value, whether the ratio of occurrence frequency during the formation period is greater than or equal to a certain level, or a combination thereof. When the dominant player-role assignment and the secondary player-role assignment are determined, a switch pattern may be analyzed based on the assignments. For example, a player participating in a switch or a role participating in a switch may be determined based on the difference between the primary player-role assignment and the secondary player-role assignment, i.e., a player-wise role changing between the two assignments. As another example, the number of attempts or the tendency of attempts of the corresponding switch may be determined based on the occurrence frequency of the secondary player-role assignment. Meanwhile, when the formation period includes a plurality of target sessions, the above-described process may be performed for each formation period to analyze a switch pattern over the entire target session.

As another example, the switch pattern may be analyzed based on a divided role period of the formation period. First, a representative player-role assignment may be extracted on a role period basis. A role-period-wise representative player-role assignment may be the most frequent player-role assignment in the role period. When the representative player-role assignment is extracted, a player and/or role participating in the switch may be determined or the number of attempts or the tendency of attempts may be determined based on the dominant player-role assignment of the formation period and the role-period-wise representative player-role assignment. Alternatively, when the most frequent assignment is selected from among representative player-role assignments, the above-described information may be acquired based on the representative player-role assignments other than the most frequent assignment. Alternatively, the above-described information may be acquired based on adjacent representative player-role assignments. Meanwhile, when the formation period includes a plurality of target sessions, the above-described process may be performed for each formation period to analyze a switch pattern over the entire target session.

Also, according to an embodiment of the present disclosure, the SportsCPD may be used to detect an irregular situation such as a set-piece. For example, whether a corresponding scene is an irregular situation may be determined based on the scene-by-scene dominant player-role assignment with respect to the dominant player-role assignments during the formation period.

The SportsCPD according to embodiments of the present disclosure may have the following several advantages. First, the SportsCPD can detect a team's basic tactics and their changes in an unsupervised manner by applying a high-level change point detection method to sport tracking data. Second, the SportsCPD can effectively represent a formation structure and a role switch for an arbitrary time section as an average role adjacency matrix and a sequence of permutations, respectively. Third, for example, the SportsCPD can be utilized in practical applications that can be easily understood and used by those engaged in the field to search for a switch pattern or automatically detect a set-piece.

3. Related Techniques 3.1 Nonparametric Change Point Detection

Change-point detection (CPD) is a technique for finding a point at which dominant parameters change in a series of processes. CPD may be classified as a parametric type or a nonparametric type according to whether to parameters are estimated in detail or whether a change point is directly found.

In particular, since the graph-based nonparametric method uses only similarity information and thus is applicable to high-dimensional data or even non-Euclidean data, the nonparametric method is regarded as more flexible in practical application. An example of CPD is g-segmentation, which defines graph-based scan statistics. Using this, it is possible to draw a similarity graph such as a minimum spanning tree for observations and check the number of line segments connected to the observations before and after time t. In this case, when the number of line segments is significantly small, t may be regarded as a potential change point. In addition, techniques for correcting g-segmentation errors that occur when there is a change in both the mean and the deviation or when a change point is not at the center of a sequence can be considered.

However, the above-described methods have a limitation in that they can be applied only to continuous data. For example, a similarity graph for data with repeated observations may not be uniquely determined by the graph-based method described above. To solve this and obtain a unique scan statistic, discrete g-segmentation using the average of the resulting statistics or a combination of multiple optimal similarity graphs may be applied. It has been experimentally proven that discrete g-segmentation works well for discrete data such as network data.

3.2 Estimation of Formations and Roles in Team Sports

The following several studies dealt with spatiotemporal tracking data to estimate a team formation and find positions, i.e., player roles in a sports game. Balkoski's paper "Large-scale analysis of soccer matches using spatiotemporal tracking data (2014)" proposes a role representation algorithm that dynamically assigns a unique role to each player on a scene-by-scene basis. This algorithm is similar to the K-means algorithm, except that a Hungarian algorithm is used in the E-step to satisfy a constraint that no two players should play the same role at the same time. Narizuka and Yamazaki's paper "Characterization of the formation structure in team sports (2017)" proposes a method of representing a temporary formation as a non-directional graph using Delaunay triangulation and clustering graphs for a single game to characterize a formation structure. Narizuka and Yamazaki's follow-up paper "Clustering algorithm for formations in football games (2019)" combines role representation techniques to cluster formations across multiple games.

The above-described approaches cannot distinguish between a fixed role change that is caused by a tactical instruction and a temporary role swap that is mostly not intended from a macroscopic point of view. In an actual team sport game environment, generally, a change according to a coach's instruction occurs not at all or at most several times, and a role change is not instructed every short time section (e.g., every second). By applying the change point detection algorithm according to an embodiment of the present disclosure to tracking data, it is possible to detect a "practical" role change between players.

4. Definition of Problem

In team sports, a coach changes a team formation a few times during a game or instructs only a role swap between players without changing a formation. Therefore, their decision-making process can be tracked according to the following two steps. First, a formation change point is found, and then a role change point is found. In this section, each step will be treated as a separate change point detection problem with reference to FIG. 1.

FIG. 1 is an illustration of a timeline of a change in formation and role according to a result of the SportsCPD according to an embodiment of the present disclosure. In FIG. 1, the upper figures show formation-period-wise team formations. Colored dots represent scene-by-scene coordinates of specific roles that are normalized by the average location of a team. White circles denote the average locations of individual roles, and the thickness of a line connecting the circles corresponds to an element of the average role adjacency matrix. The timeline on the bottom shows roles assigned to players on a role period basis.

4.1 Detection of Formation Change Point

A team formation can be considered using the probability distribution of a role topology. The goal of FormCPD is to find a change point in distribution of a set of observations in the form of player trajectories. Therefore, first, an effective representation method representing a role topology may be found from raw observations, and thus CPD may be performed using a sequence of characteristic factors. The characteristic factors may be found, and then a change point may be detected using the sequence of characteristic factors.

Representing this as a formula, when the sequence of characteristic factors $\{A(t)\}_{t \in T}$ representing the role topology is known, $T_1 < \ldots < T_m$, which is a partition of T satisfying $t \in T_i$, which is $A(t) \sim F_i$ for some distributions $F_1, \ldots, F_m$, which are distinct from one another. Here, each section $T_i$ may be referred to as a formation period in which a team has a unique formation represented as a distribution $F_i$.

4.2 Detection of Role Change Point

Balkoski's above-mentioned paper proposes a role representation in which roles are assigned to field players, except for a goalkeeper in a soccer game, on a scene-by-scene basis, but it is not possible to distinguish between a long-term tactical change and a temporary role swap. Given that players typically play a fixed role instructed by their coach over a certain period of time, the goal of the RoleCPD is to find a change point at which a long-term tactical change occurs. That is, the formation period $T_i$ may be additionally divided into some time sections $T_{i,1} < \ldots < T_{i,ni}$, in which players have fixed roles and which may be referred to as role periods. Then, the mutual change between scene-by-scene roles according to the result of role representation in the role period may be regarded as a temporary swap.

Representing this as a formula, when a role set $\chi = \{X_1, \ldots, X_N\}$ that satisfies the following formula and a player-to-temporary-role map (P-TR map) $\{\beta_t: P \to \chi\}_{t \in T}$ can be found for the set P of players during a game time T according to the role expression.

$$\beta_t(p) \neq \beta_t(q) \ \forall p \neq q \in P, t \in T$$

Here, the temporary role map $\{\beta_t\}_{t \in T}$ may be represented as a combination of a player-to-instructed-role map (P-IR map) $\{\alpha_t: \chi \to \chi\}_{t \in T}$ and a temporary role permutation (RolePerm) $\{\sigma_t: \chi \to \chi\}_{t \in T}$, which is $\sigma_t \in S(\chi)$ for a symmetric group $S(\chi)$ for $\chi$. Specifically, it may be $\beta_t = \sigma_t \circ \alpha_t$. In other words, $T_{i,1} < \ldots < T_{i,ni}$, which is a partition $T_i$ satisfying the following conditions and the P-IR map $\{\alpha_t\}_{t \in T}$ may be found for the P-TR map $\{\beta_t\}_{t \in T}$ for the formation period $T_i$.

The first condition is period-wise consistency, where roles indicated for all players are fixed in each role period $T_{i,j}$. For example, the following equation may be satisfied for some $X_p^{(i,j)} \in \chi$.

$$\alpha_t(p) = X_p^{(i,j)} \ \forall t \in T_{i,j}$$

The second condition is uniqueness, where the same role is not assigned to any two players in one role period. For example, the following formula may be satisfied.

$$X_p^{(i,j)} \neq X_q^{(i,j)} \ \forall p \neq q \in P$$

The third condition is the existence of a role change, where a role period change may be an instruction change. For example, the following formula may be satisfied.

$$X_p^{(i,j)} \neq X_p^{(i,j+1)}$$

The last condition may be valid only for a change in a single formation period. That is, the same player-role assignment may be in distinct adjacent role periods of the formation period. As an example, the first two role periods are shown in FIG. 1.

5. Methodology

This section sequentially describes the detailed process of dividing a game session into multiple formation periods (FormCPD) and dividing each formation period into multiple role periods (RoleCPD). It should be noted in advance that the methodology described below is a non-limiting example.

5.1 Detection of Formation Change Point Based on Role Adjacency Matrix

First, a role topology for each scene may be represented using a role adjacency matrix calculated from the Delaunay triangulation. Then, a formation change point may be found using a pairwise distance between role adjacency matrices through discrete g-segmentation, which is a non-parametric change point detection algorithm. The formation of each segment can be represented with an average role adjacency matrix and may be clustered according to the entire data set in which labels used in the field, such as "3-4-3" or "4-4-2," are assigned to individual formation periods.

5.1.1 Generation of Sequence of Role Adjacency Matrix

Figure 2:
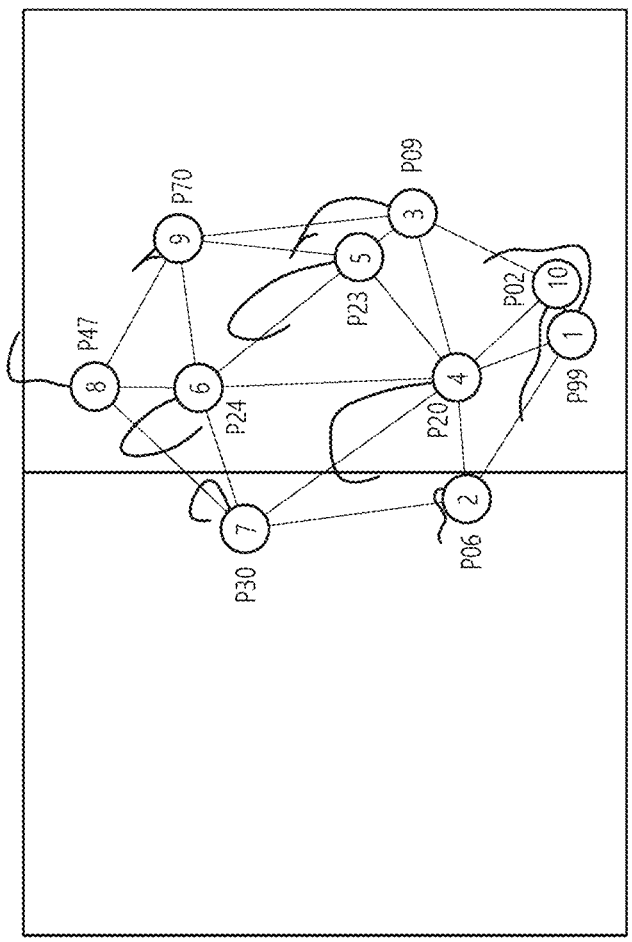
FIGS. 2 and 3 are graphs regarding role adjacency according to an embodiment of the present disclosure.

First, roles may be assigned to players on a scene-by-scene basis according to a role representation scheme. Here, the role representation may be exemplarily performed with reference to the concept presented in Balkoski's above-described paper. Then, an adjacency matrix may be acquired from the role representation. Here, for example, the adjacency matrix may be $\{A(t)\}_{t \in T} \subset R^{N \times N}$ acquired between role labels according to Delaunay triangulation. In this case, the component $A_{kl}(t)$ may be 1 when $X_k$ and $X_l$ are adjacent at t for the role group $\chi = \{X_1, \ldots, X_N\}$, and otherwise 0. FIG. 2 shows an example of a Delaunay graph for role locations.

Figure 3:
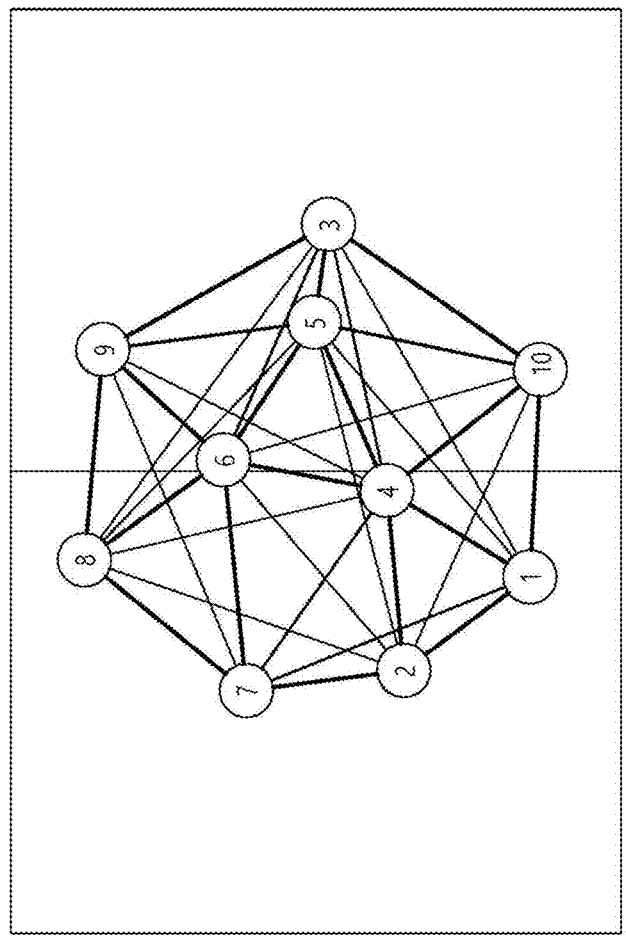

FIGS. 2 and 3 are graphs regarding role adjacency according to an embodiment of the present disclosure. FIG. 2 is a temporary Delaunay graph for player trajectories in an arbitrary scene, and FIG. 3 is a weighted graph drawn from average role locations and an average role adjacency matrix for a formation period. Numbers in circles indicate role labels 1 to 10, and numbers under the circles in FIG. 2 are the jersey numbers of corresponding players.

The application of Delaunay triangulation to player tracking data was first proposed by Narizuka and Yamazaki. However, they used jersey numbers as indices of an adjacency matrix and applied the role representation only if the jersey numbers matched a single index set across several games. According to this, it is possible to explore position swap patterns well, but as a result, player adjacency matrices may be significantly affected by irregular situations such as a temporary switch or a set-piece where an original team formation collapses. Therefore, a more robust representation of a formation structure can be made using a role label, instead of such a player label, as an index of an adjacent matrix.

5.1.2 Application of Discrete G-Segmentation to Matrix Sequence

To find formation changes, CPD may be applied to a sequence of role adjacency matrices obtained from each session (e.g., the first or second half) of a game. Among various CPD methods, discrete g-segmentation has the distinction of being applicable to high-dimensional or non-Euclidean data with repeated observations. Considering that it is a high-dimensional observation (e.g. a 10×10 binary matrix calculated from 10 field players in the case of soccer) in which the sequence of the embodiment of the present disclosure is frequently repeated, high reliability can be expected for applying discrete g-segmentation.

First, g-segmentation may be exemplarily performed as follows. First, for a given observation, a similarity graph G such as a minimum spanning tree may be constructed. Next, for each timestamp, line segments may be classified into three types, i.e., type-0 edges connecting observations before and after t, type-1 edges connecting observations before t, and type-2 edges connecting observations after t. Accordingly, $R_0(t)$, $R_1(t)$, and $R_2(t)$, which are the numbers of corresponding types of line segments, may be obtained. From this, when $\Sigma(t)$ is the covariance matrix of $(R_1(t), R_2(t))^T$ under a null distribution obtained by mixing time indicators, a generalized line-segment-count scan statistic may be defined as follows.

$$S(t) = (R_1(t) - E[R_1(t)], R_2(t) - E[R_2(t)])^T \Sigma^{-1}(t) (R_1(t) - E[R_1(t)], R_2(t) - E[R_2(t)])$$

Similar observations are more likely to be connected by a line segment than distinct observations, so large S(t) may indicate small within-group distances and large inter-group distances (where "group" refers to a time section with respect to t). Thus, when $S(\tau)$ exceeds a predefined threshold according to an algorithm, it may be determined that $\tau = \arg\max_t S(t)$ indicates a change point.

However, the similarity graph may not be uniquely defined in the g-segmentation, and thus the g-segmentation may not be suitable for data processing with repeated observations. Therefore, the discrete g-segmentation can overcome the shortcomings of g-segmentation using averaging statics $(R_{1,(a)}(t), R_{2,(a)}(t))$ or union statics $(R_{1,(u)}(t), R_{2,(u)}(t))$ instead of $(R_1(t), R_2(t))$. The statistics may be acquired using a similarity graph G0 created by the distinct values of the observations and the numbers of observations before and after t.

When obtaining a matrix sequence by applying discrete g-segmentation, the following L1,1 matrix norm (hereinafter referred to as "Manhattan distance") may be used to measure the distance between role adjacency matrices.

$$d_M(A(t), A(t')) = \|A(t) - A(t')\|_{1,1} = \Sigma_{k=1 to N} \Sigma_{l=1 to N} |A_{kl}(t) - A_{kl}(t')|$$

Also, when temporary roles assigned to players in each scene t differ from their most frequent roles throughout the session, it may be determined that the players swap the roles in a corresponding scene t. A switch ratio at t may be calculated from the number of switching players, and scenes with a high switch ratio (e.g., 0.7 or more) may be excluded as invalid situations, such as set-pieces, where players do not maintain the formation at all. In summary, the discrete g-segmentation can use pairwise Manhattan distances to return a predicted change point among the remaining sequence of valid adjacency matrices.

When a change point is found for a given period of time, the algorithm may determine its significance depending on each or a combination of the three conditions. As a specific example, an estimated change point $\tau$ may be considered significant only when (1) the p-value of the scan statistic is less than 0.01, (2) two segments last for at least a minimum amount of time (e.g., five minutes), and (3) the average role adjacency matrices computed from the segments are sufficiently far from each other (i.e., the Manhattan distance is large). A critical distance for (3) may be empirically set to 7.0.

Since two or more formation change points may exist during a session, a recursive framework may be constructed to find multiple change points. First, when a significant change point is within a given period, a CPD algorithm is applicable to sequences before and after the change point. Branch change point detection (branchCPD) may be terminated when there is no significant change point in a segment of interest. Consequently, a given session T may be divided into several formation periods $T_1 < \ldots < T_m$.

5.1.3 Formation Clustering Based on Average Role Adjacency Matrix

Based on the above, formation in a formation period $T_i$ may be calculated as a weighted graph $F(T_i) = (V(T_i), A(T_i))$ when average role locations $V(T_i) = |T'_i|^{-1} \Sigma_{t \in T'_i} V(t)$ are provided as vertices and average role adjacency matrices $$A(T_i) = |T'_i|^{-1} \Sigma_{t \in T'_i}$$

A(t) are provided as edge matrices. Here, T'i is a set of valid timestamps with a low switch ratio among Ti, and $V(t)=(v_1(t), \ldots, v_N(t))^T \in R^{N \times 2}$ indicates two-dimensional locations of N roles which are normalized such that the average is 0 (e.g., $\Sigma_{k=1 to N} v_k(t)=(0,0)$) for each scene t. FIG. 3 is an example of a formation graph.

Here, the distance between a pair of arbitrary formations may be defined by aligning the roles and calculating the Manhattan distance between the above-described role adjacency matrices. Specifically, it is assumed that any pair of formations are F=(V,A) and F'=(V',A') in a formation period. Here, F and F' do not necessarily belong to the same game and may be calculated from different games. Next, the rows and columns of A may be realigned into the rows and columns of A'. For example, a Hungarian algorithm may be used for the rearrangement, and in this case, the pairwise Euclidean distance between V and V' may be used. In other words, an optimal permutation matrix Q for minimizing an assignment cost $c(V,V'; Q)=\Sigma_{k=1 to N} \|(QV)_k - v'_k\|_2$ may be calculated. For example, $QAQ^T$ and A' may be used as in the case where the distance between the formations F and F' is calculated as $d(F,F')=d_M(QAQ^T, A')$.

According to this distance, the clustering of formations may be performed to determine whether the formations are the same or different using the entire data set. When agglomerative clustering is applied to the pairwise formation distance, a formation graph may be grouped into multiple clusters. In the embodiment of the present disclosure, for example, the soccer field is classified into seven groups, which are labeled with terms familiar to those engaged in the field.

Figure 4:
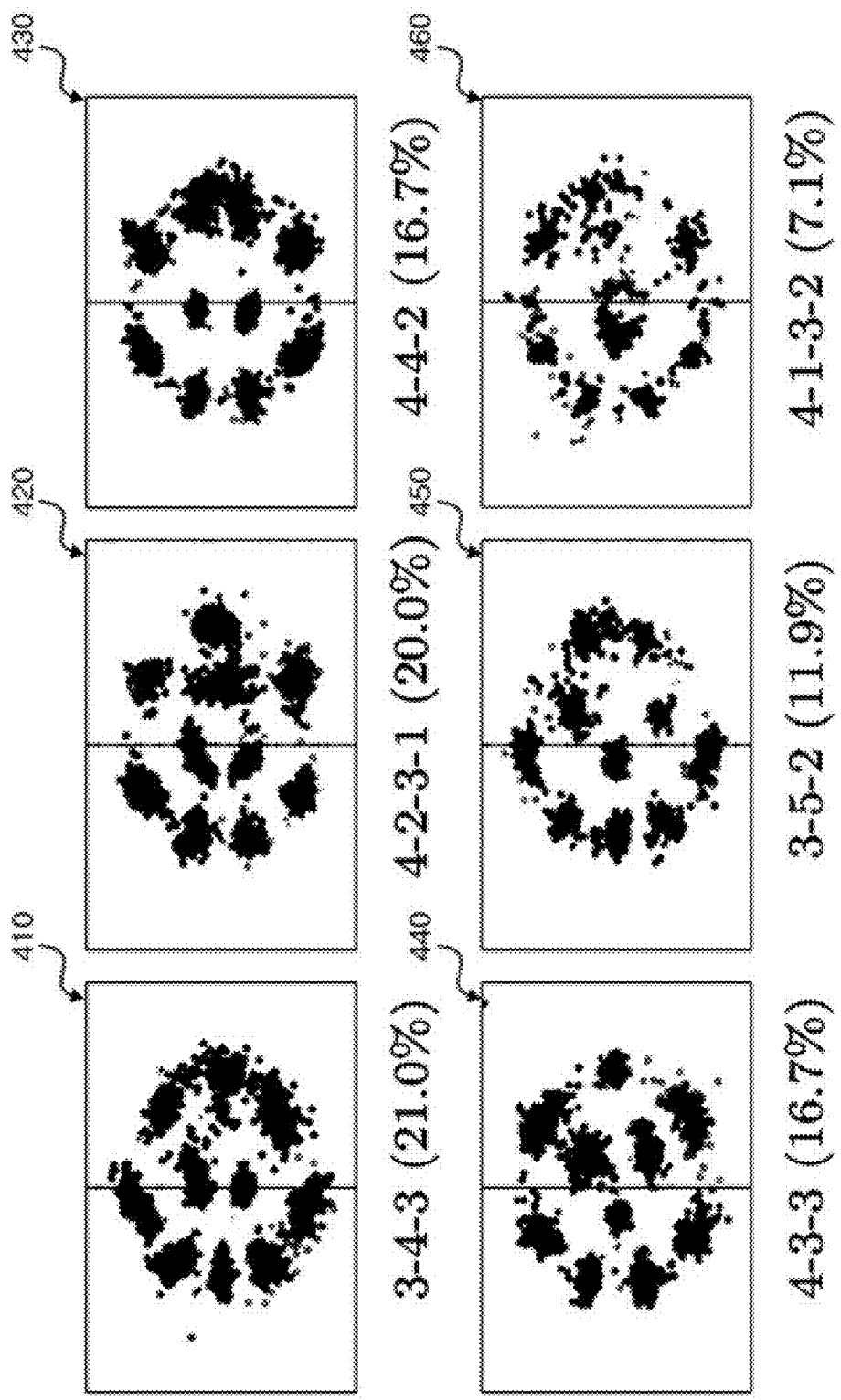
FIG. 4 shows an example of a formation group according to an embodiment of the present disclosure.

FIG. 4 shows an example of a formation group according to an embodiment of the present disclosure. FIG. 4 shows the average role locations of formation groups, which are labeled with soccer terms. The figures in parentheses represent proportions with respect to the total playtime. The result of FIG. 4 is calculated using raw data, that is, location data obtained from GPS data as player tracking data. Specifically, the result of FIG. 4 is obtained by applying the SportsCPD to 809 sessions for 2.33 million seconds, dividing the sessions into 866 formation periods and 2,158 role periods, clustering the 866 formation periods into 32 clusters, and then merging the 32 clusters into seven formation groups.

While the technique proposed by Balkoski uses Earth Mover's Distance (EMD) between role locations, the clustering according to an embodiment of the present disclosure may use the distance between average role adjacency matrices. Also, only formations for the halves of a game, which have a nearly constant time length, are targeted in the conventional art, but in the embodiment of the present disclosure, formations may be handled for formation periods that are shorter or vary in length so that they are likely to cause distortion of a formation graph. This is because an average role adjacency matrix based on adjacency relationships rather than absolute locations is more robust against this distortion.

5.2 Detection of Role Change Point Based on Role Permutation

The RoleCPD may be performed in a similar way to the FormCPD, except that a role permutation is used instead of a role adjacency matrix. A role change point may be found by recursively applying discrete g-segmentation to each formation period. Next, an original role given to each player may be found on a role period basis, and a scene-by-scene player-role assignment may be represented as the permutations of designated roles.

5.2.1 Generation of Role Permutation

In the above-described role representation, an initial role $X_p$ may be assigned to each player p according to, for example, a standard number such as a jersey number. Using this, temporary role assignments to players $p_1, \ldots, p_N$ at time t may be represented as permutations $\pi_t = (\pi_t(Xp_1), \ldots, \pi_t(Xp_N)) \in S(\chi)$ for initial role assignments $(Xp_1i, \ldots, Xp_N)$. This may be represented as the following formula.

$$\beta_t(p) = \pi_t(X_p)$$

5.2.2 Application of Discrete G-Segmentation to Permutation Sequence

Similar to that applied to the role adjacency matrix, g-segmentation may be applied to a sequence of role permutations $\{\pi_t\}_{t \in T_i}$ for each formation period $T_i$. According to this, a predicted change point may be determined from a sequence of valid permutations (e.g., permutations when a switch ratio is less than or equal to 0.7) using the distance between the role permutations as a Hamming distance $d_H(\pi_t, \pi'_t) = |\{X : \pi_t(X) \neq \pi'_t(X), X \in \chi\}|$.

Similar to the FormCPD, the significance of a change point may be tested. In this case, the last condition applied to the FormCPD may be excluded. Since the goal of the RoleCPD is to find when a dominant role assignment is changed, the change point τ may be determined to be significant only when the most frequent permutations are different before and after the change point τ.

Finally, by applying recursive CPD to the sequence in each formation period $T_i$, the partitions $T_{i,1} < \ldots 21 T_{i,ni}$ of $T_i$ may be acquired.

5.2.3 Derivation of Designated Role for Player on Role Period Bsis

For each role period $T_{i,j}$, a designated role for a player may be set as the most frequent permutation, and all temporary roles obtained from a role representation may be represented as the permutations of the designated roles. Expressing this as a formula, the P-IR map $\{\alpha_t : P \to \chi\}_{t \in T_{i,j}}$ may be represented as $\alpha_t(p) = \pi_{i,j}(X_p)$, which is a fixed value for $t \in T_{i,j}$ when, for example, $\pi_{(i,j)} \in S(\chi)$ is the most frequent permutation among $\{\pi_t\}_{t \in T_{i,j}}$. For $t \in T_{i,j}$, the role permutation $\sigma_t(X_p) = \beta_t \circ \alpha^{-1}$ may be acquired as follows.

$$\sigma_t(X_p) = \beta_t(\alpha_t^{-1}(X_p)) = \pi_t(\pi_t(\pi_{(i,j)})^{-1}(X_p))$$

Accordingly, the P-IR map may satisfy the above-described three conditions. Specifically, since $\alpha_t(p)$ is constant for $t \in T_{i,j}$ and is a permutation of a distinct initial role, $\alpha_t(p)$ is distinguished over $p \in P$ and thus has temporal consistency and uniqueness. Also, the existence of a role change can be secured between adjacent role periods due to the significance test.

6. Experiment

The accuracy of the SportsCPD may be evaluated by comparing the results according to an embodiment of the present disclosure to actual values recorded by experts in the field. Also, according to an embodiment of the present disclosure, an interpretation technique for identifying play patterns of a team in terms of a role switch may be provided. Also, a switch ratio according to an embodiment of the present disclosure may be used as a simple and reliable indicator for set-piece detection.

6.1 Model Evaluation

The performance of the SportsCPD may be measured in two ways. One is the accuracy of a predicted formation by the FormCPD, and the other is the robustness of role change point detection according to the RoleCPD. For the former, the ratio of precisely detected minute-wise segments to the total number of segments (e.g., the total of play minutes) may be calculated. For the latter, given that change point detection is about the classification of timestamps between change points and non-change points, how accurately the RoleCPD can detect the change points can be measured.

For the two types of evaluation, actually measured labels may be used by experts who work in the field as video analysts or coaches for professional or semi-professional sport teams. Since it is very exhausting to record formations and roles in minutes, a record of one game by an expert was used for evaluation according to an embodiment of the present disclosure.

Figure 5:
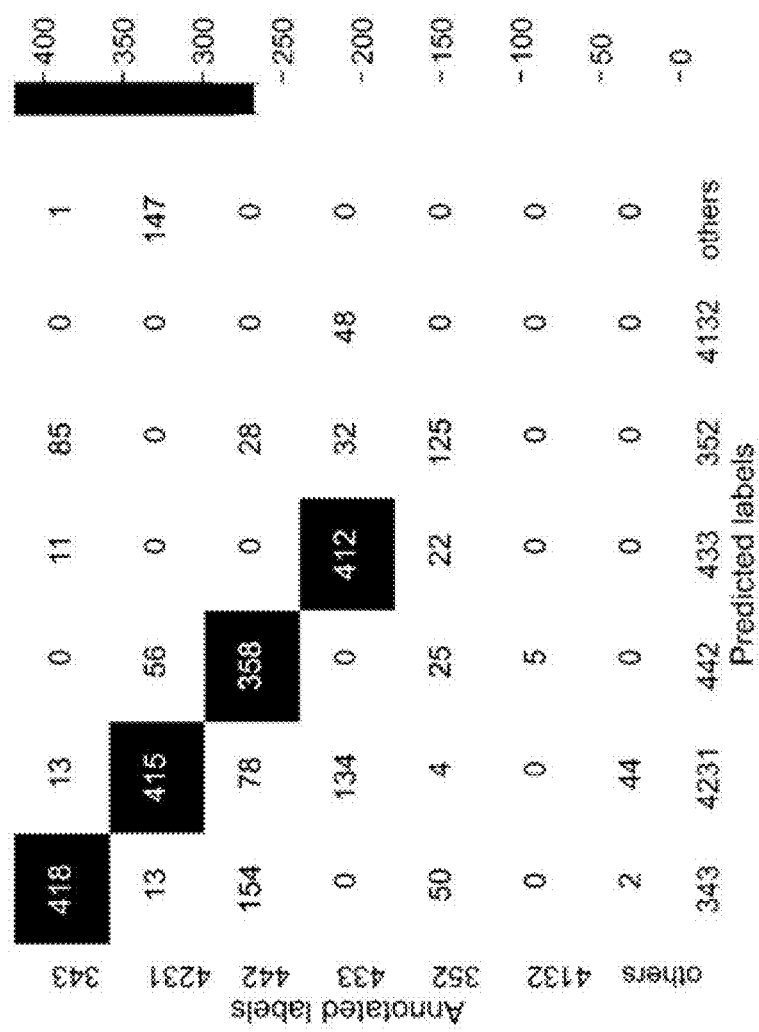
FIG. 5 is a diagram related to formation prediction according to an embodiment of the present disclosure.

For the formation prediction, a comparison was performed using labels for minute-wise segments rather than formation periods. This is because a change point detected through the method according to an embodiment of the present disclosure and a change point detected by a human expert are somewhat different. The record for 2,047 minutes out of a total playtime of 2,680 minutes and the result of the FormCPD were matched, which showed a matching percentage of 76.4%. FIG. 5 shows a detailed result as a confusion matrix.

FIG. 5 is a diagram related to formation prediction according to an embodiment of the present disclosure. FIG. 5 shows the accuracy of the formation prediction using a confusion matrix, which is obtained by comparing a formation predicted in minutes to an actually measured and recorded formation.

Meanwhile, the RoleCPD detected 96 change points in 28 games. 86 change points were located within a five-minute distance from the recorded change points, and there were a total of 7 missing change points (false negatives). Therefore, the recall points and $F_1$ scores regarding the accuracy of the RoleCPD are 0.8958 (86/96), 0.9247 (83/93), and 0.9101 (2*(precision×recall)/(precision+recall)).

6.2 Switch Pattern Search

The role permutation obtained as described above may indicate a temporal role switch between players. The role permutation $\sigma_t$ may be an identity permutation when all players retain their original roles given at time t. In other words, the non-identity role permutation may mean that a switch play occurred at a corresponding time. Therefore, by analyzing the non-identity permutation, the play pattern of a team may be identified.

Figure 6:
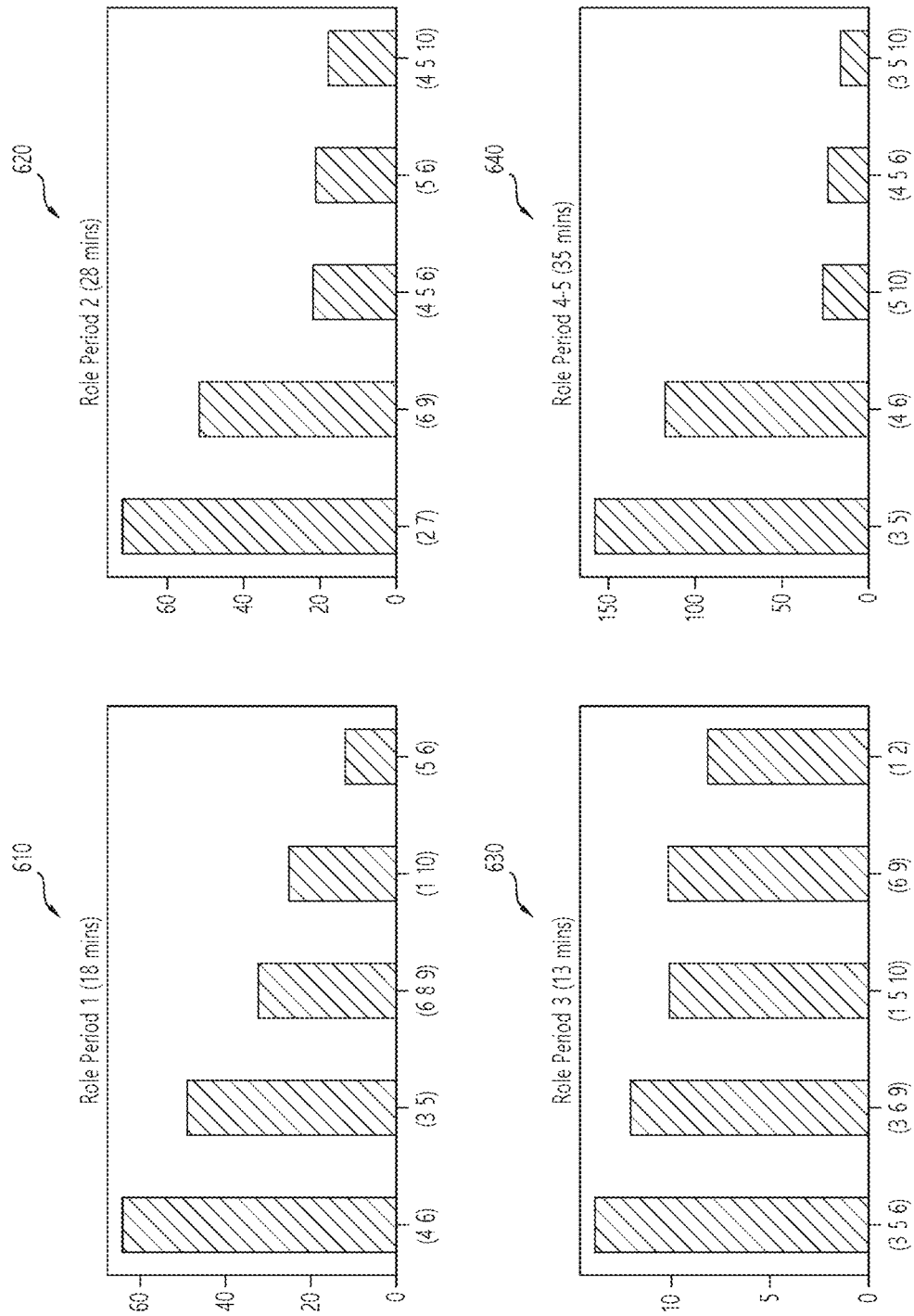
FIG. 6 is a graph relating to a role permutation for each formation period according to an embodiment of the present disclosure.
Figure 7:
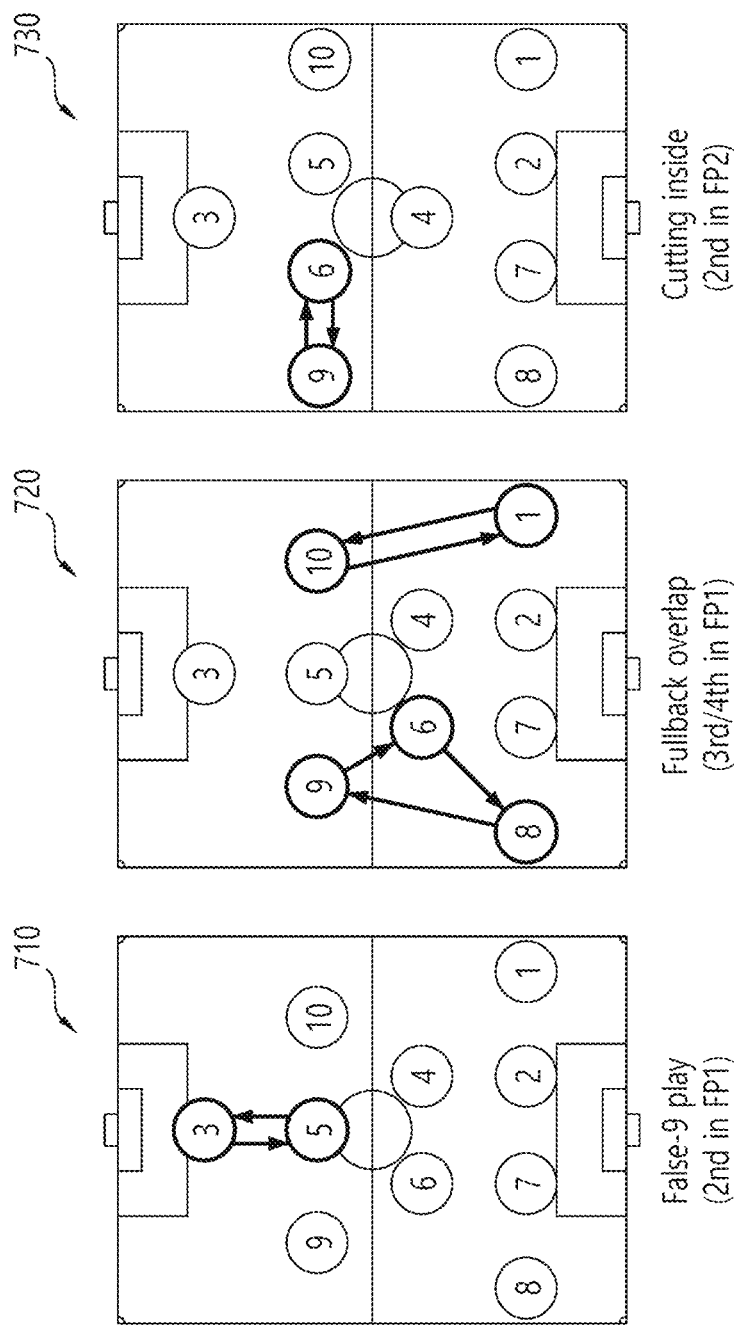
FIG. 7 is a diagram relating to an example of a tactical analysis using a role permutation according to an embodiment of the present disclosure.

FIG. 6 is a graph relating to a role-period-wise role permutation according to an embodiment of the present disclosure. In FIG. 6, the periods of the top five most frequent role permutations on a role period basis are represented in seconds. FIG. 7 is a diagram relating to an example of a tactical analysis using a role permutation according to an embodiment of the present disclosure.

Referring to the results of FIGS. 6 and 7 for the game shown in FIG. 1, it is obvious that a team's tactical pattern may be discerned from a role permutation for a specific game. FIG. 6 shows the five most frequent role permutations for each role period, and the following analysis was performed from the role permutations. In the analysis below, the formation period and the role period are referred to as FP and RP, respectively, and a player assigned a specific role k will be denoted as Rk.

First, players actively perform a role switch for $Rp_1$ (in this section, the total time of the top 3 most frequent role permutations is 140 seconds out of 18 minutes, and players hardly perform a switch for RP3 (in this section, the total time of the top 3 most frequent role permutations is 35 seconds out of 13 minutes).

Second, a role permutation (3 5) occurs frequently for $Rp_1$ and refers to "false 9play" shown in FIG. 7 in which a center forward moves behind a midfielder to provide space for fellow players. However, the corresponding player reduced the corresponding play when the team formation changed to "4-3-3."

Third, in $Rp_1$ unlike other RPs, fullbacks R1 and R8 have taken an offensive role along the sides and have actively performed an overlap play with wingers R9 and R10. Here, it was revealed that the overlaps were different on both sides. On the left side, R6 covered the location of R8, resulting in a three-person cycle of (6 8 9), whereas on the right side, R4 did not cover the location of R1, resulting in a two-person cycle of (1 10).

Fourth, in RP2, the left winger R9 continuously attempted a cut-in play towards a penalty box through the (6 9) switch.

Fifth, in RP4, after a center forward R5 was added, the team kept the formation constant except for normal switches (e.g. switches in the same position) such as a switch (R3 R5) between center forwards or a switch (R4 R6) between central midfielders.

6.3 Set-Piece Detection

In a sports game, a set-piece may be a situation in which a game is paused and then resumed. In particular, in the case of soccer, a ball may be sent to a scoring area in a set-piece situation, and a set-piece such as a free kick or a corner kick is regarded as a good opportunity to score points. Accordingly, many teams carefully review set-piece situations in the last game and even conduct special tactical training for a set-play.

Figure 8:
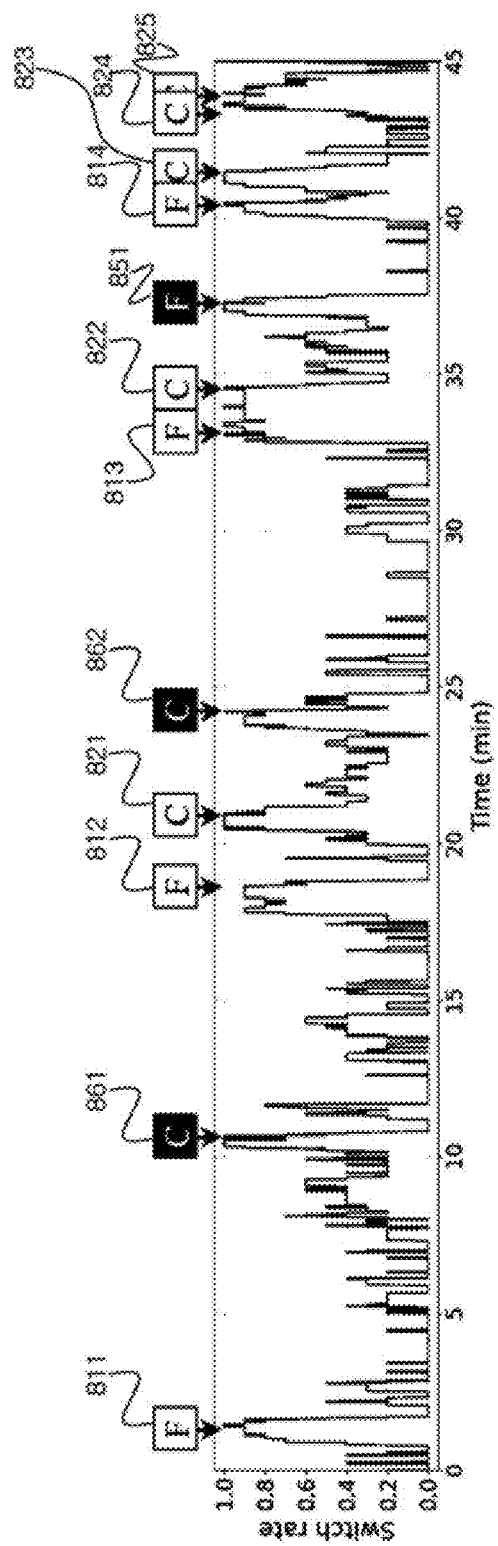
FIG. 8 is a diagram illustrating a relationship between a switch ratio and set-piece generation according to an embodiment of the present disclosure.

By automatically detecting set-piece situations using statistical switch ratios, the result of the SportsCPD may allow sports teams to easily extract and handle set-play data. The term "switch ratio" has been defined above as the ratio of switching players but may also be defined as a value obtained by dividing the distance to the identity permutation (e.g., Hamming distance) by the number of roles. Since players are completely mixed in set-piece situations, the switch ratio in these situations may be close to almost 1.0. Thus, by using the switch ratio, it is possible to provide a simple, completely unsupervised, and fairly accurate set-piece detection model. For example, a situation in which the switch ratio is greater than or equal to a threshold value (e.g., 0.9) may be selected to detect a set-piece. FIG. 8 shows a strong cross-correlation between a switch ratio and a set-piece.

FIG. 8 is a diagram illustrating a relationship between a switch ratio and set-piece generation according to an embodiment of the present disclosure. FIG. 8 is a time-series diagram illustrating switch ratios and set-piece generation during the first half of the game shown in FIG. 1. In FIG. 8, "C" and "F" indicate corner kicks and free kicks that allow kicking into the opponent's penalty box, respectively. A white square indicates that a team for which the switch ratio is calculated in a corresponding situation is an offending team, and a black square indicates that the team is a defending team.

7. Implementation

An apparatus, system and method for implementing the SportsCPD according to the above embodiment of the present disclosure will be described below.

Figure 9:
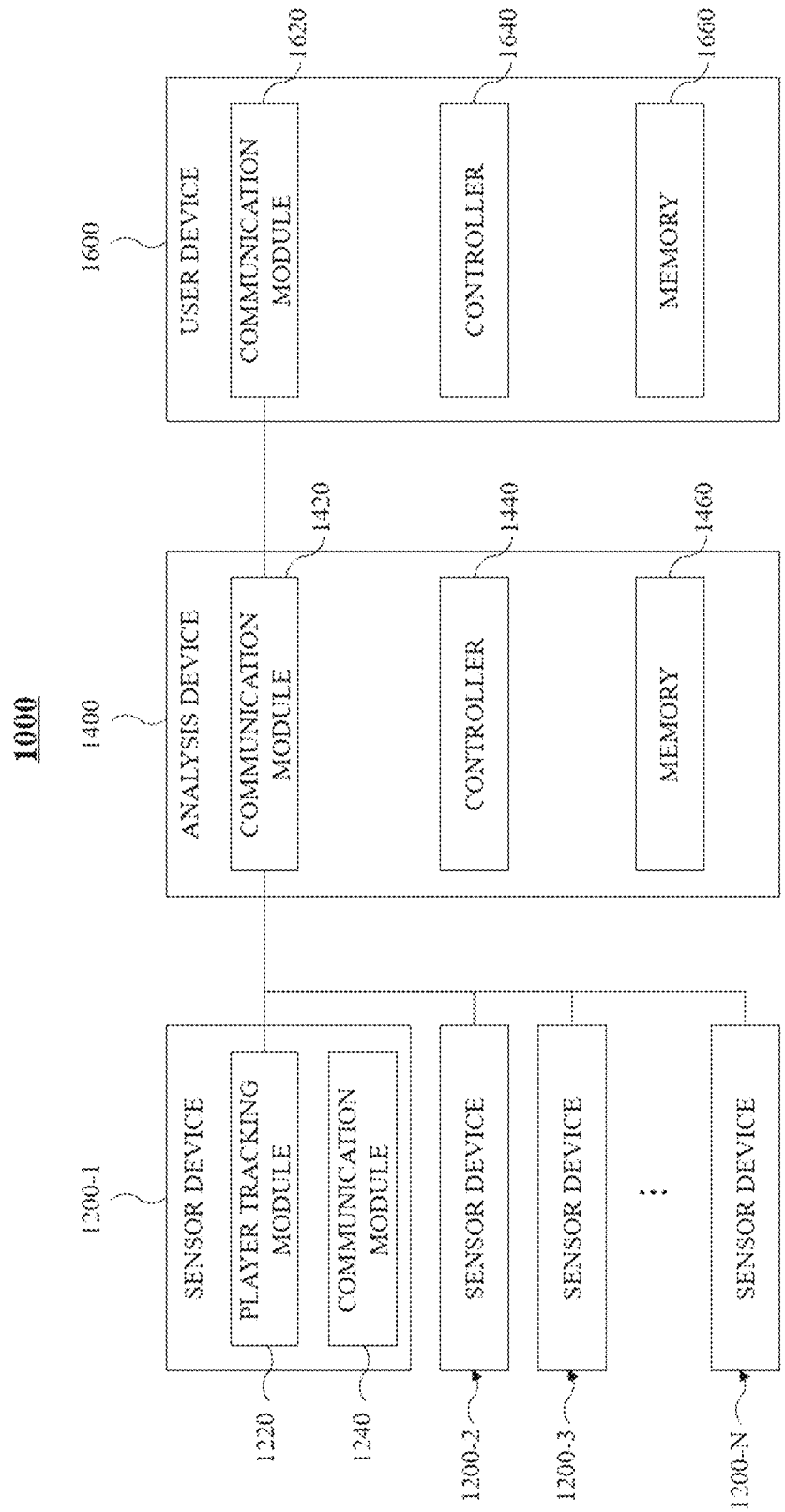
FIG. 9 is a block diagram illustrating the configuration of a system for providing tactical analysis of team sports according to an embodiment of the present disclosure.

FIG. 9 is a block diagram of a system for providing tactical analysis of team sports according to an embodiment of the present disclosure.

Referring to FIG. 9, a system 1000 may include a sensor device 1200, an analysis device 1400, and a user device 1600. The elements of the system will be described in more detail below.

The sensor device 1200 may be provided in the form of an attachable device. Here, the term "attachable device" may refer to a device that is directly or indirectly attached to a player. For example, the attachable device may be a wearable device in the form of a pocket device inserted into a player's clothes or in the form of a band wrapped around a sport player's body part such as a wrist or ankle. Since the sensor device 1200 in the form of an attachable device is attached to each player, a plurality of the sensor devices 1200 may be used in team sports.

As an example, the sensor device 1200 may perform global positioning of a player. In this case, a player tracking module 1220 may be a Global Navigation Satellite System (GNSS) module, including a Global Positioning System (GPS) module. For example, the GPS module may perform global positioning of the player by a GPS processor calculating a GPS global location (e.g., latitude and longitude) through a triangulation technique using GPS signals received from navigation satellites through a GPS antenna. The calculated global location may be delivered to the analysis device 1400 through a communication module 1240. Thus, the analysis device 1400 may acquire a player tracking data set. Also, in this process, the analysis device 1400 may transform the global location delivered from the sensor device 1200 into a player field coordinate system.

As another example, the sensor device 1200 may perform local positioning of the player. In this case, the sensor device 1200 may operate as a tag node of a local positioning system (LPS) and may transmit or receive an LPS signal to and from an anchor node fixedly installed in a positioning area. When global positioning is performed, the sensor device 1200 may independently perform positioning. On the other hand, when local positioning is performed, the sensor device 1200 may simply function as a transceiver for LPS signals of the local positioning network, and a positioning result may be calculated by an external device.

For example, the sensor device 1200 may transmit or receive an LPS signal to or from the anchor node, and the positioning of the player may be performed by an external device using a result of transmitting or receiving the LPS signal between nodes in the network. At this time, the analysis device 1400 may receive the result of transmitting or receiving the LPS signal and directly perform positioning to generate player tracking data or receive the positioning result from a separate external device that performs positioning using the result of transmitting or receiving the LPS signal.

Meanwhile, the sensor device 1200 in the tactical analysis system 1000 may be replaced with an image analysis platform unlike that shown in FIG. 9. The image analysis platform may be provided as an image analysis device for calculating the location of an object (e.g., player or ball) in an image through an image analysis that uses a camera, a top-view transformation and deep learning algorithm, etc. In this case, the analysis device 1400 may directly receive an image from a camera and perform an image analysis to generate a player tracking data set or may receive the positioning result from a separate external device for performing an image analysis.

The analysis device 1400 may perform the various operations described above in relation to the SportsCPD according to an embodiment of the present disclosure. Basically, unless otherwise stated, the various operations described above with respect to the SportsCPD may be interpreted as being performed by the analysis device 1400, and in particular, it should be noted that the operations may be performed by a controller 1440. For example, the analysis device 1400 may receive information that directly or indirectly reflects a player location from the sensor device 1200, generate a player tracking data set from the information, and perform the above-described SportsCPD and various related applications (such as irregular-situation detection) using the player tracking data set. The analysis device 1400 may be provided in the form of a personal computer or a local or remote server and may not necessarily be physically provided as a single entity.

The analysis device 1400 may include a communication module 1420, the controller 1440, and a memory 1460.

The communication module 1420 may perform data transmission or reception between the analysis device 1400 and an external device (e.g., the sensor device 1200 or the user device 1600). For example, the analysis device 1400 may collect data from an attachable device through the communication module 1420, receive an image from a camera, or transmit various types of information to the user device 1600 through a web.

The controller 1440 may control the overall operation of the analysis device 1400. The controller 1440 may be implemented as a hardware configuration, a software configuration, or a combination thereof. In terms of hardware, the controller 1440 may be provided in various forms capable of performing computations or data processing, including electronic circuits, integrated circuits (ICs), microchips, and processors. Also, since the physical configuration of the controller 1440 is not necessarily limited to a single physical entity, the controller 1440 may be provided as a single processor that comprehensively processes all operations of the analysis device 1400 or a plurality of processors that perform different functions or may be provided in a form combined with some of the other components of the analysis device 1400.

The memory 1460 may store various data related to operation of the analysis device 1400. The memory 1460 may include various volatile and nonvolatile memories.

The user device 1600 may function as a user interface that provides various data or information collected or calculated by the system 1000 to a user or receives a user input from a user. For example, the user device 1600 may receive a tactical analysis result from the analysis device 1400 through the communication module 1620 under the control of the controller 1640 and may provide the result to the user through a display 1660 as visual information. The user device 1600 may be a smart device such as a smartphone or tablet, a personal computer such as a notebook or a desktop computer, or a similar electronic device.

Various examples of the tactical analysis method in an embodiment of the present disclosure will be described below with reference to FIGS. 10 to 18. FIGS. 10 to 18 are flowcharts of examples of a method of providing a tactical analysis of team sports according to an embodiment of the present disclosure.

The following methods may be used alone or in combination with each other, and not all operations of the methods are essential. Thus, it will be appreciated that some or all of the operations of the methods may be performed. Also, since the order in which the operations are mentioned in the methods is only for convenience of description, the operations are not necessarily performed only in the described order. Also, the methods will be described below assuming that they are performed by the above-described system and device, but this is also only for convenience of description. Thus, each of the methods may not be performed only by the tactical analysis system 1000 and the tactical analysis device 1400.

Figure 10:
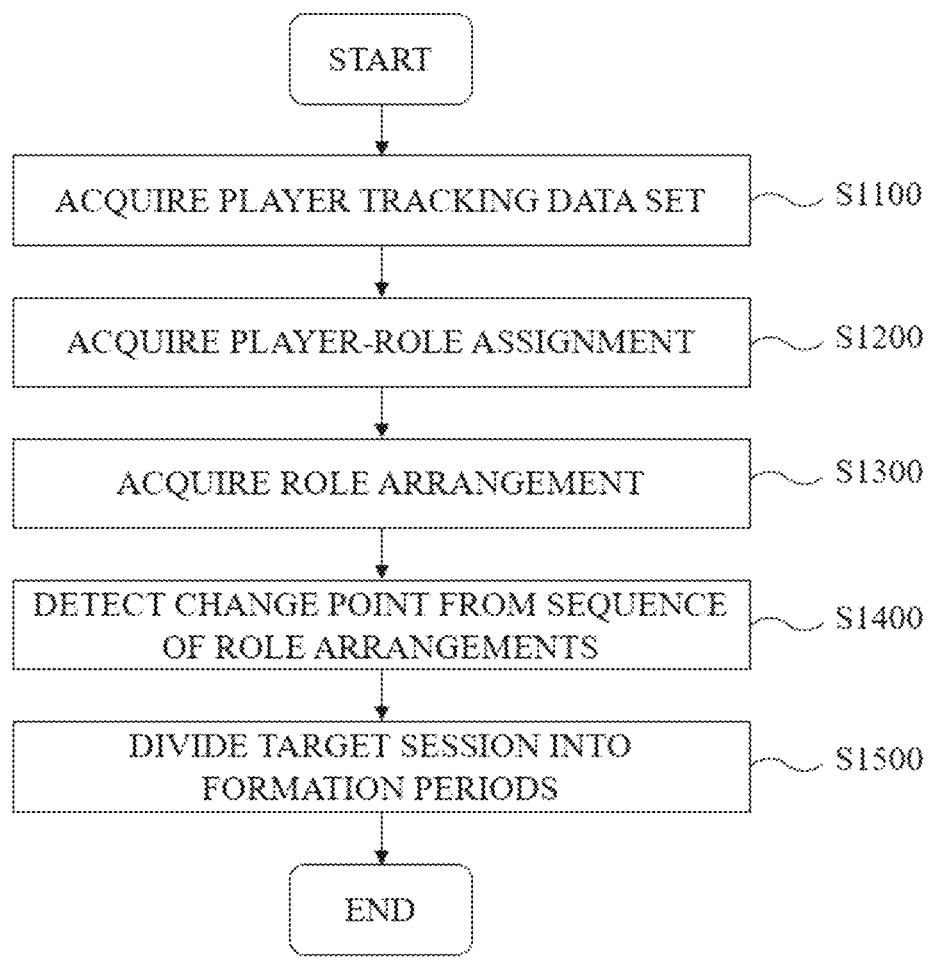
FIGS. 10 to 17 are flowcharts of examples of a method of providing tactical information for team sports according to an embodiment of the present disclosure.

Referring to FIG. 10, an example of the method of providing tactical information for team sports according to an embodiment of the present disclosure may include operations of acquiring a player tracking data set (S1100), acquiring a player-role assignment (S1200), acquiring a role arrangement (S1300), detecting a change point from a role arrangement sequence (S1400), and dividing a target session into formation periods (S1500). The operations of this example will be described below.

An analysis device 1400 may acquire a player tracking data set (S1100).

Specifically, a controller 1440 may receive a player tracking data set from a sensor device 1200 through a communication module 1420. When the sensor device 1200 performs global positioning, the analysis device 1400 may receive player location information represented as a global location during a target session and transform the player location information into a stadium coordinate system. When the sensor device 1200 performs local positioning, the analysis device 1400 may receive a result of transmitting or receiving an LPS signal from a local positioning network, calculate a player location using the result, and acquire a tracking data set. Alternatively, the analysis device 1400 may acquire the player tracking data set by receiving an image captured by a camera and calculating a player location from the received image or by receiving a player location calculated by an external device from a camera image.

Meanwhile, by using the locations of some or all players (e.g., the same team, field players excluding a goalkeeper, or a combination thereof) who participate in a target session in a corresponding scene, the location of each player may be corrected. For example, the corrected location of each player may be corrected as the average location of the field players of the same team in the corresponding scene.

Next, the analysis device 1400 may acquire a player-role assignment using the player tracking data set (S1200). For example, the controller 1440 may acquire a player-role assignment through a process of initially assigning single random roles to players over the entire session, acquiring the representative location of the roles based on the assignment, performing a scene-by-scene player-role assignment in consideration of the location distribution of the roles, re-calculating the location distribution of the roles in consideration of the scene-by-scene player-role assignment, and re-performing the scene-by-scene player-role assignment based on the re-calculated location distribution. In this process, the controller 1440 may exclude scenes corresponding to irregular situations when calculating the location distribution of the roles. Whether a scene corresponds to an irregular situation will be described in detail in an embodiment to be described later.

Next, the analysis device 1400 may acquire a role arrangement using the player-role assignment (S1300). For example, the controller 1440 may acquire the role arrangement using the location distribution of the roles, which has been described in detail above.

When the role assignment is acquired, the analysis device 1400 may detect a change point from a role assignment sequence (S1400) and divide a target session into formation periods using the sequence (S1500). Specifically, the controller 1440 may detect one change point by applying a change point detection algorithm to the role arrangement sequence, divide the target session into preceding and succeeding periods, and acquire a formation period by applying a change point detection algorithm to the divided periods to perform subdivision. Furthermore, the controller 1440 may determine whether the change point detected by the change point detection algorithm is valid according to some conditions, which has been described in detail above.

Figure 11:
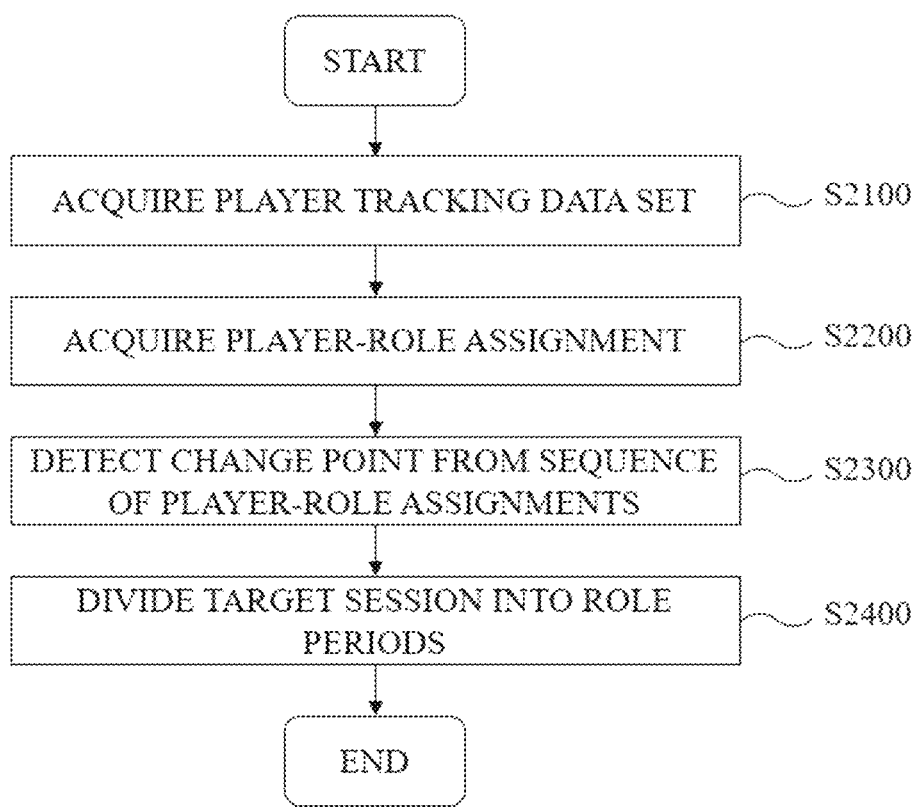

Referring to FIG. 11, an example of the method of providing tactical information for team sports according to an embodiment of the present disclosure may include operations of acquiring a player tracking data set (S2100), acquiring a player-role assignment (S2200), detecting a change point of a player-role assignment sequence (S2300), and dividing a target session into role periods (S2400). The operations of this example will be described below.

First, an analysis device 1400 may acquire a player tracking data set (S2100). The process of acquiring a player tracking data set may be performed similarly to operation S1100. However, in this case, the player tracking data set may be related to the entire target session, or alternatively, may be related to one formation period. When the entire session is divided into a plurality of formation periods, the method of the present example may be repeatedly performed for each formation period.

Next, the analysis device 1400 may acquire a player-role assignment (S2200), detect a change point from a sequence of player-role assignments (S2300), and divide a target session into role periods (S2400). Specifically, similar to the description of operation S1200, the controller 1440 may acquire a player-role assignment for each scene and may determine a change point by applying a change point detection algorithm to a sequence of the player-role assignments. Even in this case, the controller 1440 may determine the validity of the change point through some conditions (this has been described in detail above) and may divide the role period based on the valid change point.

Figure 12:
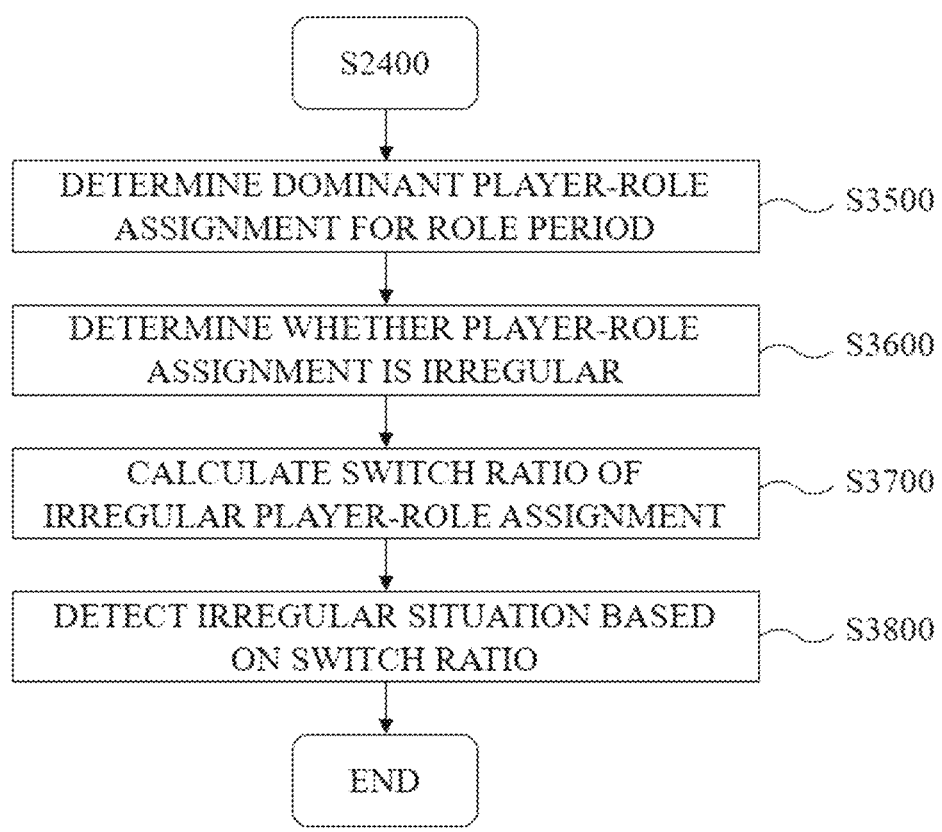

Referring to FIG. 12, an example of the method of providing tactical information for team sports according to an embodiment of the present disclosure may further include, in addition to the method of FIG. 11, operations of determining a dominant player-role assignment for the role period (S3500), determining whether the player-role assignment is an irregular player-role assignment (S3600), calculating a switch ratio for the irregular player-role assignment (S3700), and detecting an irregular situation during the target session based on the switch ratio (S3800). The operations of this example will be described below.

In this example, an analysis device 1400 may determine a dominant player-role assignment for each of the role periods into which the session is divided (S3500). Specifically, the controller 1440 may determine the most frequent player-role assignment as a dominant player-role assignment during a corresponding period.

When the dominant player-role assignment is determined, the analysis device 1400 may determine whether the scene-by-scene player-role assignment is an irregular player-role assignment based on the dominant player-role assignment (S3600) and calculate a switch ratio for the irregular player-role assignment (S3700). Specifically, the controller 1440 may determine whether a scene corresponds to an irregular situation based on the difference between the scene-by-scene player-role assignment and the dominant player-role assignment. For example, when the player-role assignment is represented as a role permutation and the distance between the two (e.g., Hamming distance) is greater than or equal to a threshold value or the two are different, the controller 1440 may determine that the corresponding player-role assignment is an irregular player-role assignment, The controller 1440 may calculate a switch ratio for the irregular player-role assignment, and the switch ratio is a value reflecting the difference between the dominant player-role assignment and the irregular player-role assignment. This has been described in detail above.

When the scene-by-scene switch ratio is calculated, the analysis device 1400 may detect an irregular situation during the target session based on the switch ratio. For example, the controller 1440 may determine that a scene where a switch ratio is greater than or equal to a threshold value is an irregular situation.

Figure 13:
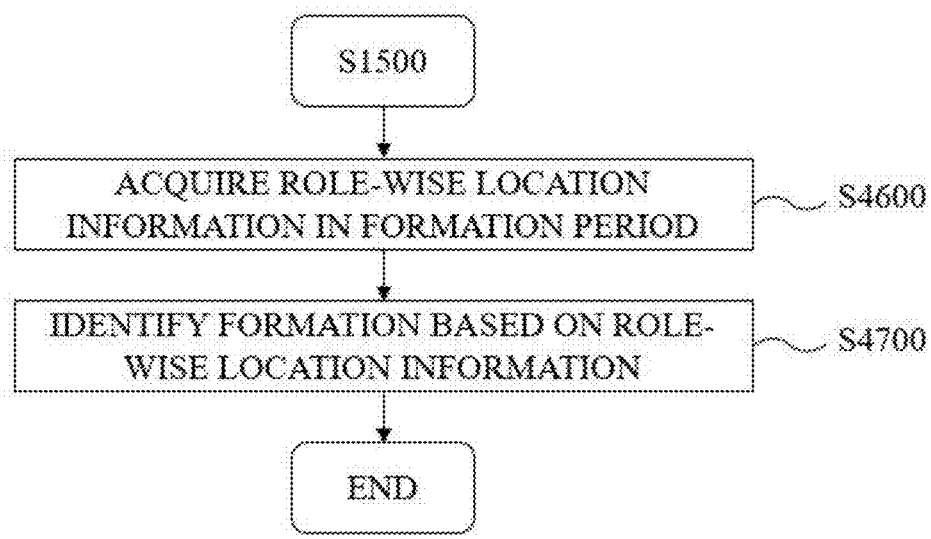

Referring to FIG. 13, an example of the method of providing tactical information for team sports according to an embodiment of the present disclosure may further include, in addition to the method of FIG. 10, operations of acquiring role-wise location information for the formation period (S4600) and identifying a formation based on the role-wise location information (S4700). The operations of this example will be described below.

In this example, when a formation period obtained by dividing the target session is acquired, an analysis device 1400 may acquire role-wise location information for the formation period (S4600). Here, the acquisition of the formation period may be performed by the analysis device 1400, for example, according to the method described with reference to FIG. 10, and the analysis device 1400 may acquire the role-wise location information over the entire session based on the acquired formation period. For example, the controller 1440 may determine the location of the scene-wise role with reference to the player tracking data set and the scene-wise player-role assignment and acquire role-wise location information over the entire session using the scene-wise role. Here, the role-wise location information may be the location distribution or average location of the roles over the entire session.

Then, the analysis device 1400 may identify a formation based on the role-wise location information (S4700). For example, the controller 1440 may determine the formation of a corresponding session by inputting the location information of the role to a deep learning algorithm trained using training data in which the location information of the role is labeled with a formation identifier recognizable by those engaged in the field. As another example, the controller 1440 may cluster location information of roles obtained from multiple different sessions, determine a group including location information of this session, and determine a formation identifier assigned to the group as a formation identifier for this session. This has been described in detail above.

Figure 14:
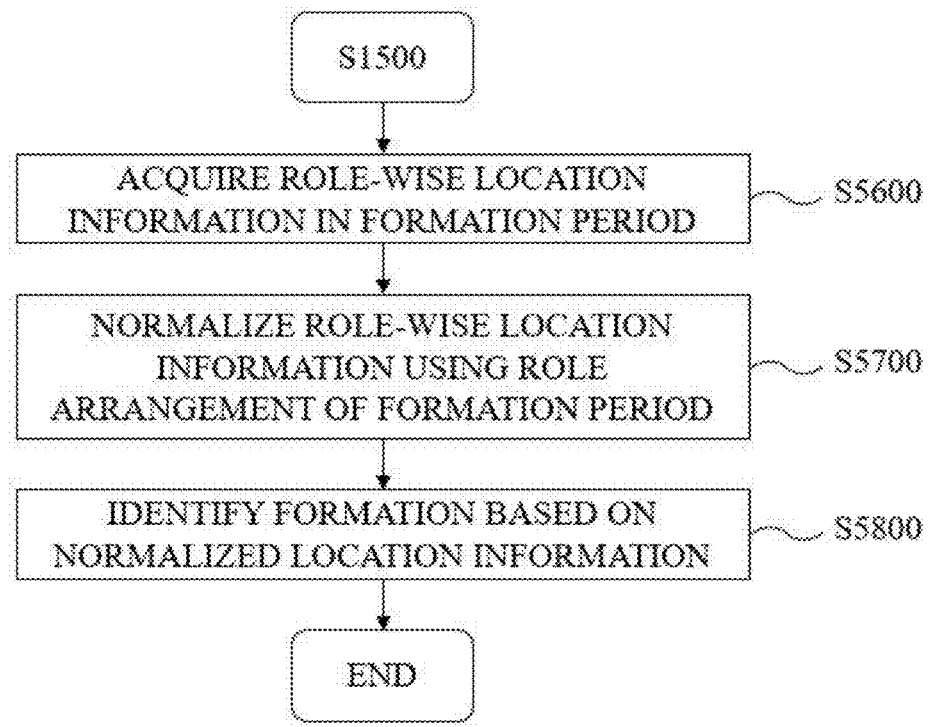

Referring to FIG. 14, an example of the method of providing tactical information for team sports according to an embodiment of the present disclosure may further include, in addition to the method of FIG. 10, operations of acquiring role-wise location information for the formation period (S5600), normalizing the role-wise location information using a role arrangement for the formation period (S5700), and identifying a formation based on the normalized role-wise location information (S5800). The operations of this example will be described below.

In this example, when a formation period obtained by dividing the target session is acquired, an analysis device 1400 may acquire role-wise location information for the formation period (S5600) and normalize the role-wise location information using a role arrangement for the formation period (S5700). Here, the normalization may be performed by reassigning roles according to role-wise location information obtained during different formation periods. Given that an initial role assignment is arbitrarily performed for the player-role assignment in this description, the player-role assignment defined in this session may be different from player-role assignments defined in other sessions. That is, for example, when the player-role assignment is represented as a role permutation, the order of vectors may not match between different sessions, so it is necessary to normalize the order in vectors between similar roles. By using role-wise location information and role arrangements, it is possible to secure compatibility between player-role assignments during different sessions (e.g., different games). This task may be performed by the controller 1440. To this end, the analysis device 1400 may use an algorithm that can match the turn numbers of players in the player-role assignment through clustering or classification of data for the role-wise location distribution, the role arrangements, and the player-role assignments obtained in advance in various sessions.

Then, the analysis device 1400 may identify a formation based on the role-wise location information (S5800). For example, the analysis device 1400 may identify a formation for the corresponding session from the role-wise location information using a deep learning algorithm or a classification algorithm acquired during the clustering process. This has been described in detail above and thus will be omitted here.

Figure 15:
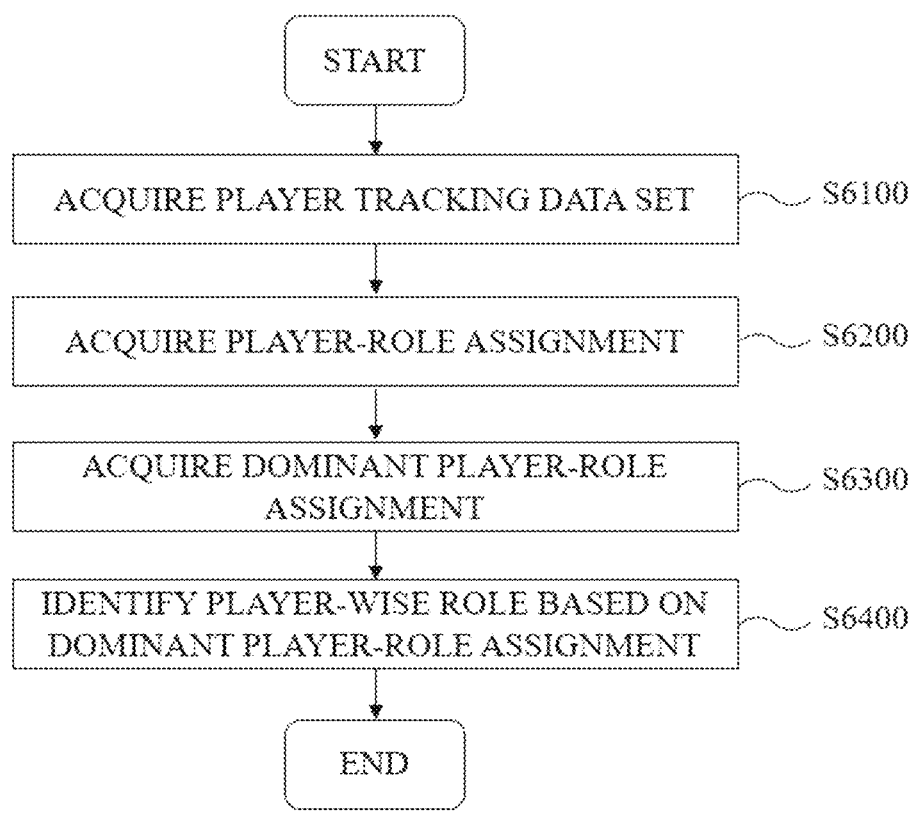

Referring to FIG. 15, an example of the method of providing tactical information for team sports according to an embodiment of the present disclosure may include operations of acquiring a player tracking data set (S6100), acquiring a player-role assignment (S6200), acquiring a dominant player-role assignment (S6300), and identifying a player-wise role based on the dominant player-role assignment (S6400). The operations of this example will be described below. The operations of this example will be described below.

In this example, an analysis device 1400 may acquire a player tracking data set (S6100), acquire a player-role assignment (S6200), and acquire a dominant player-role assignment (S6300). Here, the player tracking data set relates to the entire session or the formation period, and in the latter case, a player-wise role that is constantly maintained during the formation period is acquired.

Next, the analysis device 1400 may identify a player-wise role based on the dominant player-role assignment (S6400). Accordingly, the player-wise role may be finally interpreted as a position name that can be identified by those engaged in the field. Specifically, a controller 1440 may determine a player's dominant role according to the dominant player-role assignment, determine location information of the role as location information of the player, and identify the player's position from the location information of the player. In this case, a deep learning algorithm that receives location information of an individual player or other players and outputs a position label may be used. Alternatively, other classification algorithms may be used. Also, a formation identifier according to the above-described example may be additionally used in team sports having a more complex formation.

Figure 16:
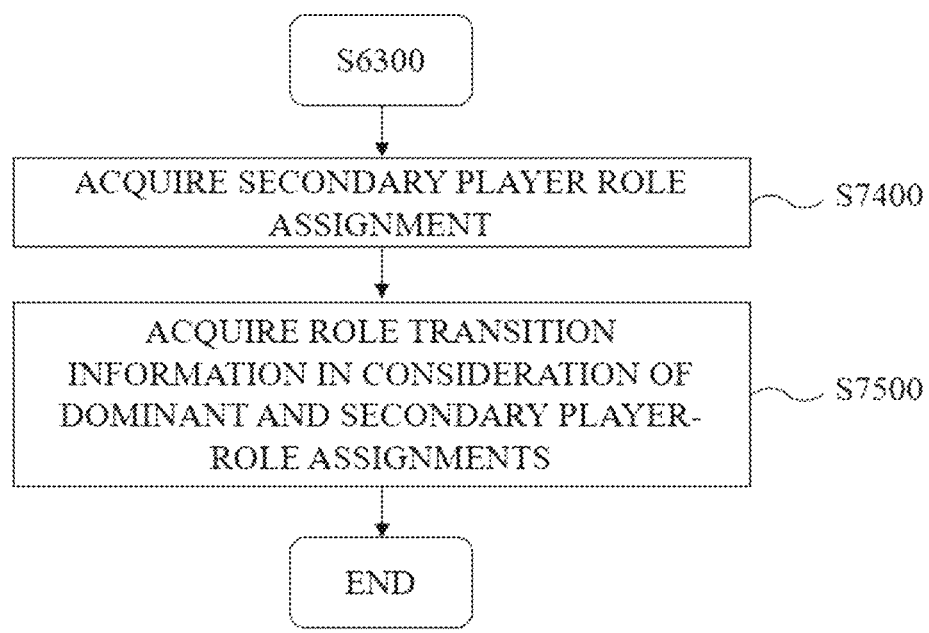

Referring to FIG. 16, an example of the method of providing tactical information for team sports according to an embodiment of the present disclosure may further include, in addition to the method of FIG. 15, operations of acquiring a secondary player-role assignment (S7400) and acquiring role transition information in consideration of the dominant player-role assignment and the secondary player-role assignment (S7500). The operations of this example will be described below.

In this example, when the dominant player role assignment is completed according to some examples described above, the analysis device 1400 may acquire a secondary player-role assignment (S7400) and acquire role transition information in consideration of the dominant player role assignment and the secondary player role assignment (S7500). Here, the secondary player role may be a player-role assignment with high frequency except for the dominant player role. A controller 1440 may detect a secondary player-role assignment for a session by applying the above-described secondary player-role determination condition.

Next, the analysis device 1400 may acquire role transition information in consideration of the dominant player-role assignment and the secondary player-role assignment. For example, the controller 1440 may determine a frequency at which two player-role assignments occur based on the frequency of the dominant player-role assignment and the frequency of the secondary player-role assignment or may determine roles or players that switch roles with each other in consideration of player-wise roles changed in the dominant player-role assignment and the secondary player-role assignment. In addition, the role transition information has been described in detail above.

Figure 17:
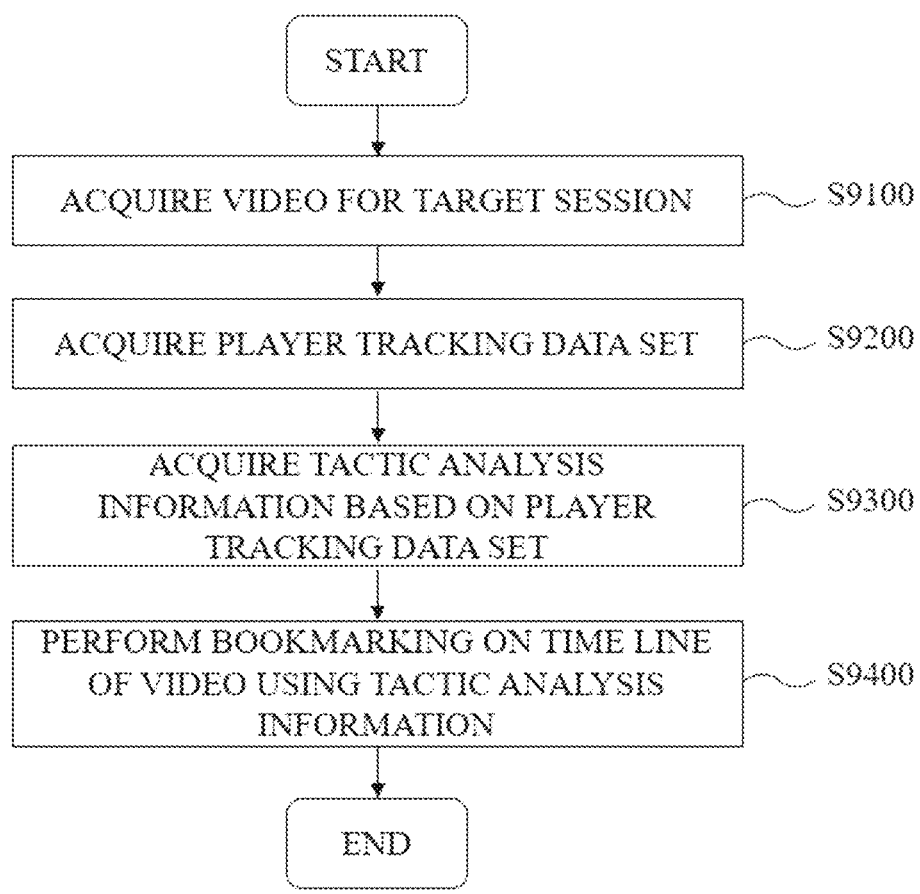

Referring to FIG. 17, an example of the method of providing tactical information for team sports according to an embodiment of the present disclosure may include operations of acquiring an image for a target session (S9100), acquiring a player tracking data set for the target session (S9200), acquiring tactical analysis information from the player tracking data set (S9300), and bookmarking a timeline of the image using the tactical analysis information (S9400). The operations of this example will be described below.

First, an analysis device 1400 may acquire an image for a target session (S9100) and acquire player tracking data set (S9200). Here, the image, which is an image captured by an external camera, may be an image related to a sports game or training, and the player tracking data set may be player location information for the same session.

Next, the analysis device 1400 may acquire tactical analysis information from the player tracking data set (S9300). Here, the tactical analysis information may include the above-described role transition information, information on whether it is an irregular situation, and information on a formation period or a role period. For example, the controller 1440 may specify a time at which a position switch between players occurs or a period during which the position switch is performed using information acquired from some examples described above (e.g., the result of comparison between the dominant player-role assignment and the secondary player-role assignment). As another example, the controller 1440 may specify an occurrence time or period of an irregular situation through detection of the irregular situation based on a switch ratio. As still another example, the controller 1440 may specify a formation period or a role period by detecting a formation change point or a role change point.

When the tactical analysis information is acquired as described above, the analysis device 1400 may bookmark the timeline of an image using the tactical analysis information. For example, the controller 1440 may bookmark the timeline of the image with time information related to the position switch, time information related to the role period, time information related to the formation period, etc. To this end, the analysis device 1400 may perform time synchronization between the image and the player tracking data set in advance. Meanwhile, here, during bookmarking, information that identifies the type of event that occurred (e.g., "full-back overlap," "forward-midfielder position swap," "corner kick," etc.) may also be displayed in addition to simply marking a timestamp.

Meanwhile, it should be noted in advance that the methods according to the above embodiments of the present disclosure are described and illustrated, for convenience of description, as using some of the methods according to other embodiments of the present disclosure.

The above embodiments of the present disclosure may be provided as a computer software program implementing some or all of the above-described methods or operations. For example, a computer software program may include program code provided in a form in which it is tangibly recorded on a machine-readable medium, and the program code contains instructions for executing steps or operations of a method according to an embodiment of the present disclosure. Such a computer program may be downloaded from a network through a communication part and then installed and/or may be installed from a removable medium. Also, the computer program may be executed by a processor capable of reading program code to perform steps or operations according to an embodiment of the present disclosure.

Also, the above embodiments of the present disclosure may be provided in the form of a computer-readable recording medium in which all or part of the above-described software program is recorded. Such a recording medium may be a conventional memory device such as a floppy disk, a hard disk, a CD-ROM, or a memory card or may be downloaded through the Internet or a computer communication network and then used.

8. Conclusion

An embodiment according to the present disclosure provides SportsCPD, which is a change point detection framework. The SportsCPD can distinguish tactically intended changes in formation and role in team sports from a temporary change. First, a temporary role topology and a position transposition may be represented as a binary matrix and a permutation sequence, respectively. This may be used to find formation and role assignment change points by applying a non-parametric change point detection algorithm (e.g., discrete g-segmentation) to high-dimensional or non-Euclidean data with frequent repetition values. Since the concepts of formation and role are the most basic and intuitive ways to express the most basic and intuitive sports team tactics, tracking and summarizing changes in team formation and role is valuable in itself to those engaged in the field. Furthermore, additional information such as a temporary permutation may be used to search for a switch pattern or to detect a set-piece. Accordingly, embodiments of the present disclosure may be widely used in the field of team sports.

Embodiments in which the SportsCPD of the present disclosure is used in the field of team sports will be described in more detail below. However, the scope of the technical spirit of the present disclosure is not limited by the following embodiments, and it should be noted that the following embodiments are merely for exemplarily describing at least a part of the technical spirit of the present disclosure.

Acquisition of Player Tracking Data

Figure 18:
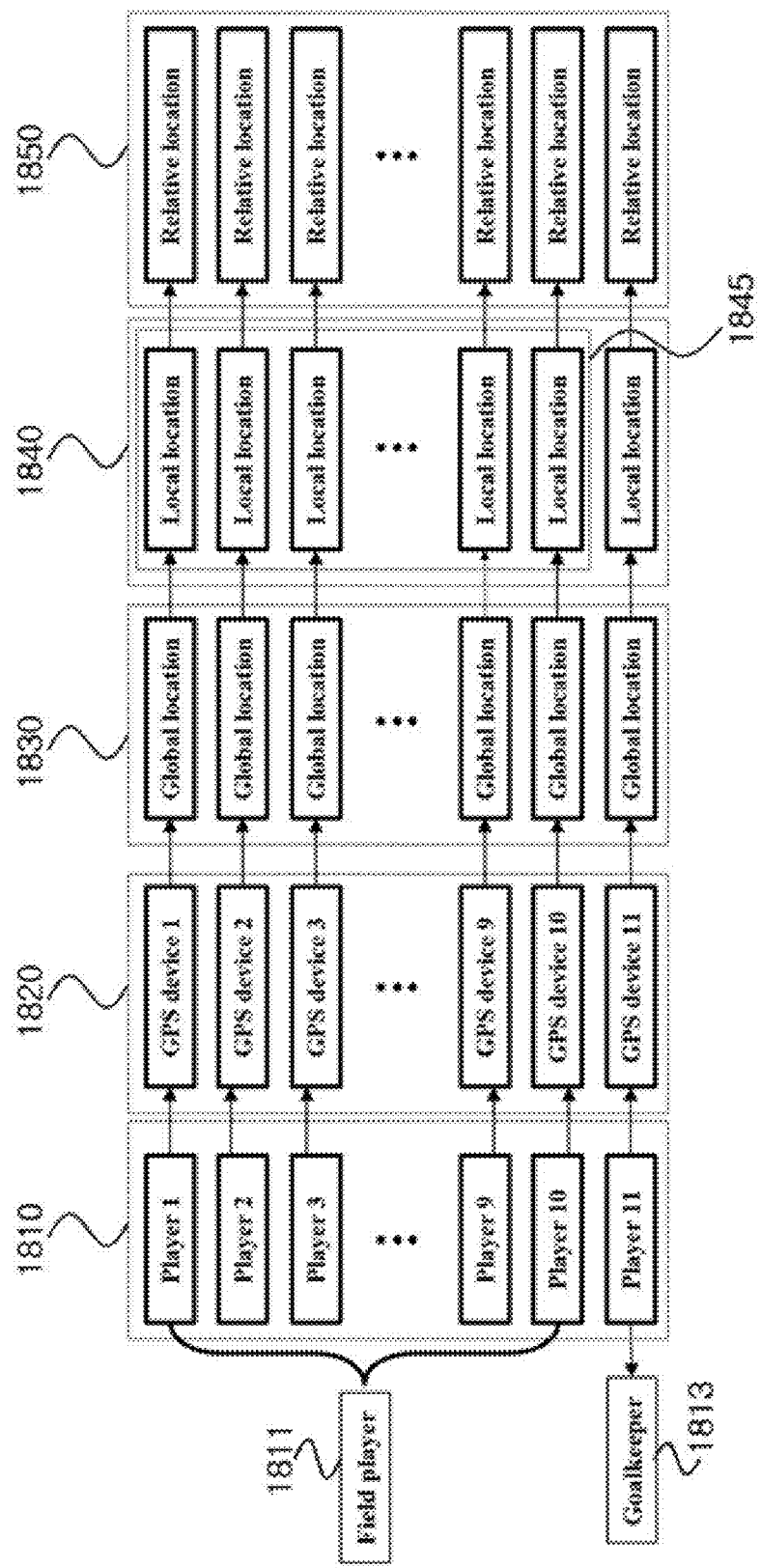
FIG. 18 illustrates an example process for acquiring player tracking data to be used according to an embodiment of the present disclosure.

FIG. 18 illustrates an example process for acquiring player tracking data to be used according to an embodiment of the present disclosure. A process of acquiring player tracking data to be used in embodiments of the present disclosure will be described in detail below with reference to FIG. 18.

In this description, the term "player tracking data" may be used as a concept including a sequence of location data of a corresponding player during a target time period to be analyzed. The target time period includes a plurality of time points, and location data including information on a player's location may be acquired at each of the plurality of time points. The player tracking data may include location data at each of the plurality of time points.

FIG. 18 shows, for example, an acquisition procedure for a sequence of location data of players in a team participating in a soccer game. In a soccer game, one team includes a total of 11 players 1810, which may be composed of 10 field players 1811 and one goalkeeper 1813.

In order to acquire location data of each of the players 1810, location information acquisition devices 1820 may be matched to corresponding players 1810. The location information acquisition device 1820 may be, for example, the sensor device 1200 described above with reference to FIG. 9. Although, for example, a GPS device is shown as the location information acquisition device 1820 of FIG. 18, a device 1820 for acquiring location information of players 1810 according to the present disclosure is not limited to a GPS device. For example, as described above in association with the sensor device 1200, any technique for acquiring the location information of the players 1810, such as GPS, LPS (e.g., based on UWB or Bluetooth), or OTS (image analysis) may be applied. For convenience of description, a GPS technology-based location tracking procedure will be exemplified and described.

The players 1810 may each be instructed to wear corresponding GPS devices 1820 and participate in the game. The GPS device 1820 may receive a GPS signal from a satellite, and thus the GPS devices 1820 may output global locations 1830 of corresponding players. For example, the GPS device 1820 may be configured to output GPS data (latitude, longitude, and altitude) at a sampling rate of 10 Hz, i.e., at 0.1-second sections. Information output by the GPS device 1820 may be delivered to a server. For example, the server may be an analysis device 1400 as described above with reference to FIG. 9.

Therefore, when it is assumed that the time normally taken from the start to the end of a soccer game, including halftime, is 120 minutes, 72,000 pieces (120 minutes×60 seconds/minute×10 Hz) of location data are secured for each player. According to an embodiment, the number of local locations 1840 or relative locations 1850 acquired from the above GPS location data may or may not be the same as the number of global locations 1830.

The analysis device 1400 may receive a global location 1830 from a GPS device and convert the global location 1830 into a local location 1840 according to a stadium coordinate system. The stadium coordinate system may be a two-dimensional coordinate system in which any one of the corners of a stadium is the origin, for example, the x-axis is the length of the stadium, and the y-axis is the width of the stadium.

With reference to a reference point determined based on the local location 1830, the analysis device 1400 may be configured to calculate a relative location 1850 of each player with respect to the reference point. In a fluid team sport such as soccer, the location of each player is very variable, and it may be difficult to derive a meaningful tactical change based on an actual location before conversion to a relative location. However, the relative location with respect to the reference point at each time point may have a relatively small amount of change, and a more efficient tactical analysis may be performed through the analysis of the relative location.

Here, the reference point may be, for example, the average of the locations of the field players 1811, but the present disclosure is not limited thereto. Since the location of the goalkeeper 1813 shows a relatively small change throughout the game, it may be advantageous to determine the reference point based on the locations of the field players 1811. As the reference point, various representative values such as the midpoint as well as the average of the locations of the players 1810 may be used.

Since the reference point is calculated for each frame included in a target period, for example, the reference point may be calculated every 72,000 frames for 120 minutes, and thus the relative location 1850 of each of the players 1810 may be calculated for each frame. The location data of the players used in the embodiments of the present disclosure may be, for example, data on the relative locations 1850, but the present disclosure is not limited thereto.

As described above, by securing location data for each player at each time point within the target period to be analyzed, a player tracking data set including a sequence of location data of a corresponding player during the target period may be acquired.

Acquisition of Role Assignment Information

Figure 19:
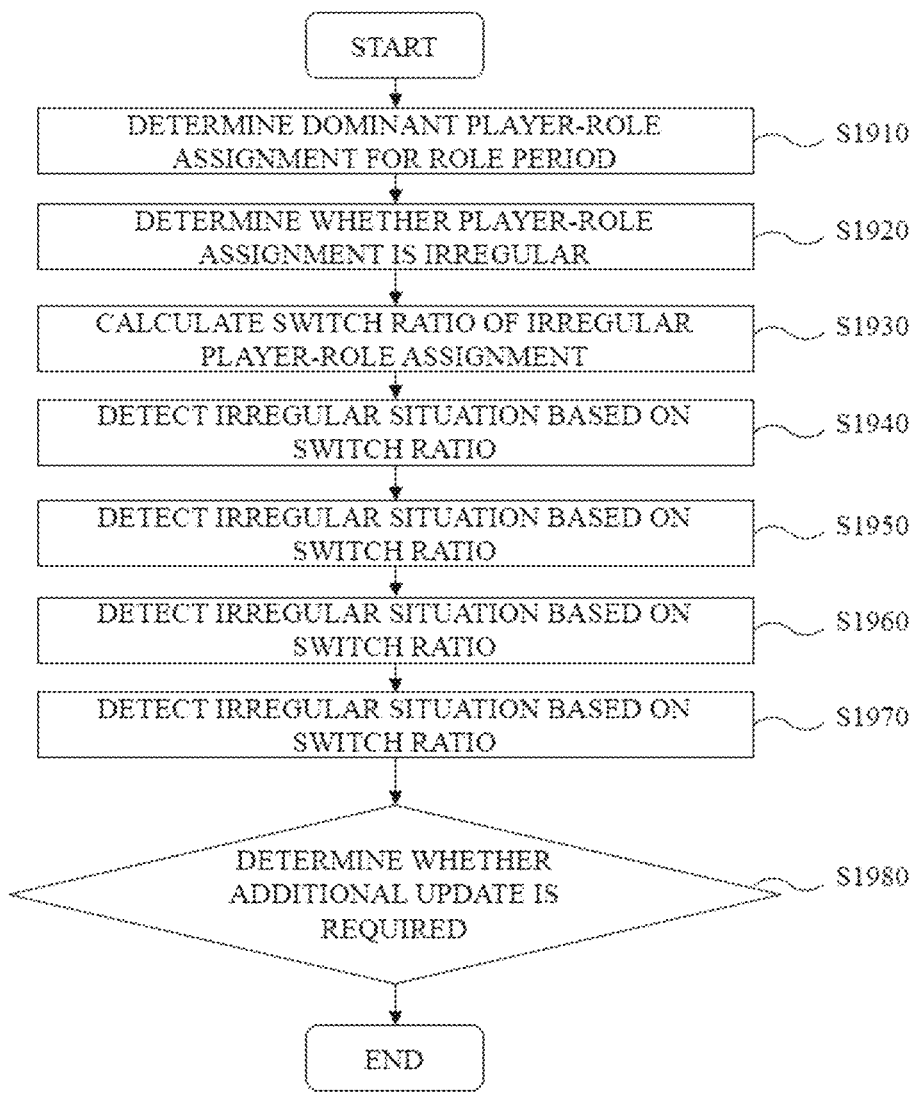
FIG. 19 is a schematic flowchart of a role assignment information acquisition process according to an embodiment of the present disclosure.
Figure 20:
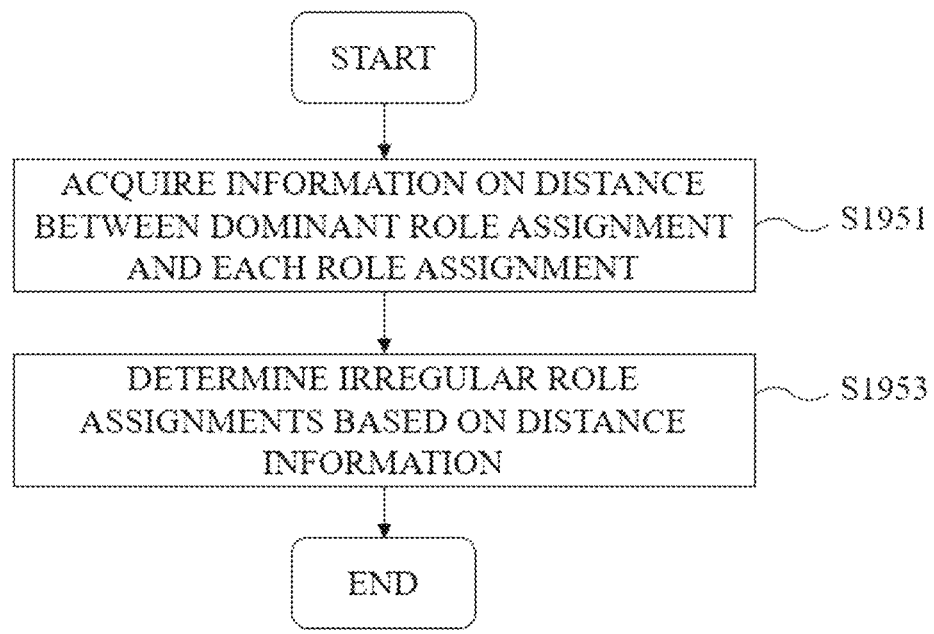
FIG. 20 is a detailed flowchart illustrating an irregular role assignment process of FIG. 19.

FIG. 19 is a schematic flowchart of a role assignment information acquisition process according to an embodiment of the present disclosure, and FIG. 20 is a detailed flowchart illustrating an irregular role assignment process of FIG. 19. A role assignment information acquisition process according to an embodiment of the present disclosure will be described in more detail below with reference to FIGS. 19 and 20.

The method and/or processes according to an embodiment of the present disclosure may be performed by a computing device. According to an aspect, the computing device may be an analysis device 1400 as described with reference to FIG. 9, but the present disclosure is not limited thereto. Any device capable of computation with a processor and a memory may be used.

In this description, the term "role assignment information" may refer to information including role assignments determined at a plurality of time points in a target period to be analyzed. "Role assignment" may indicate a plurality of role indices assigned to a plurality of players at each time point. For example, role A may be assigned to a first player, and role B may be assigned to a second player. Like this, a role index may be assigned to each player to distinguish which role he or she is performing, and the role assignment may refer to information on which role index is assigned to each player at each time point.

Referring to FIG. 18, a role assignment information acquisition process according to an embodiment of the present disclosure may include one or more of an operation of dividing a target session into at least two time sections (S1910), an operation of acquiring a player tracking data set (S1920), an operation of acquiring role assignment information (S1930), an operation of determining a dominant role assignment (S1940), an operation of determining an irregular role assignment (S1950), an operation of acquiring a space information set (S1960), an operation of updating the role assignment information (S1970), and an operation of determining whether an additional update is required (S1980). The operations of this example will be described below.

As shown in FIG. 18, the computing device may divide a target session into at least two time sections (S1910). The division of the target session may be, for example, division into formation periods and/or role periods as described in the present disclosure, but the present disclosure is not limited thereto.

More specifically, for example, the computing device may divide a target session for one team sport game into at least two time periods. Here, the at least two time periods may include a first time period and a second time period obtained through division based on a formation change of a team participating in the team sport game or a role change of at least some of a plurality of players. The division into time periods may be performed, for example, by the change point detection process as exemplified in the present disclosure but may include period division performed by any division criterion. According to one aspect, a target period subject to the role assignment may be, for example, one of the first time period or the second time period obtained through the above division.

Referring back to FIG. 18, subsequently, the computing device may acquire a player tracking data set (S1920). More specifically, the computing device may acquire a plurality of player tracking data sets for a plurality of players, and each of the player tracking data sets may include a sequence of location data of a corresponding player during a target period. That is, the computing device may acquire, for each of the plurality of players, information on locations at a plurality of time points included in the target period. It should be noted that the process for acquiring player tracking data according to an embodiment of the present disclosure described above with reference to FIG. 18 may be applied, but the present disclosure is not necessarily limited thereto. Also, according to an aspect, when the computing device divides the target session into at least two time sections, player tracking data for a plurality of time points included in the first time period or a plurality of time points included in the second time period may be acquired.

Next, the computing device may acquire role assignment information (S1930). That is, the computing device may acquire role assignment information using the plurality of player tracking data sets. The role assignment information may include a plurality of role assignments for a plurality of time points within the target period, and each of the role assignments may indicate a plurality of role indices assigned to the plurality of players at a corresponding time point.

More specifically, when the player tracking data sets are acquired and the location of each player is identified, a player-wise role may be assigned using the location.

In this disclosure, "role" may refer to one of a plurality of participant categories that can match player positions constituting a formation. That is, "role" may be a category according to the role of the game participant that can match one of a plurality of positions before determining which of the plurality of positions it corresponds to, such as "MF" or "CF." For example, a role index, such as "role A," may be assigned to such a role. As will be described below in the present disclosure, to which position each role index corresponds may be automatically identified by, for example, a computer-based technique such as an artificial neural network-based deep learning technique or a clustering technique.

Meanwhile, the term "player" used herein may refer to an entity whose location is tracked by a process of acquiring player tracking data. For example, when there is no substitution of players throughout one team sport game and also there is no change in role between players, "player" and "role" may be matched on a one-to-one basis. However, in general, in team sports, at least one player substitution occurs in one game, and a position change may also occur between field players. Accordingly, a sequence of location data for one "role" may be a mixture of at least a portion of player tracking data for two or more "players."

The role assignment is information indicating which role identifier is assigned to each of the plurality of players at each time point. The assignment of roles to the players may allow an optimal assignment to be performed based on the location distributional for the plurality of roles and the locations of the players at each time point. For example, as described above in this disclosure, a Hungarian algorithm such as a log probability density-based cost matrix may be used.

For such role assignment, first, it is required to acquire a role-wise location distribution. The role-wise location distribution may indicate a location distribution of each role in the entire session (e.g., 120 minutes) or in a target period. The role-wise location distribution may be understood to be included in a "space information set" below in the present disclosure, and the space information set may include a sequence of location data of each role at each of a plurality of time points included in a time period to be analyzed for the corresponding role. For example, when the target session is 120 minutes and the location data is acquired at a sampling rate of 10 Hz, the space information set for each role may be a sequence of 72K locations of the corresponding role.

However, the operation of acquiring role assignment information for the first time (S1930) after the player tracking data set is acquired (S1920) is performed when information on a player's location is acquired but information on a role's location is not secured. Accordingly, in the operation of role assignment information (S1930), an initial role-wise location distribution acquired by temporarily assigning one role to a player-wise location distribution may be used.

Figure 22:
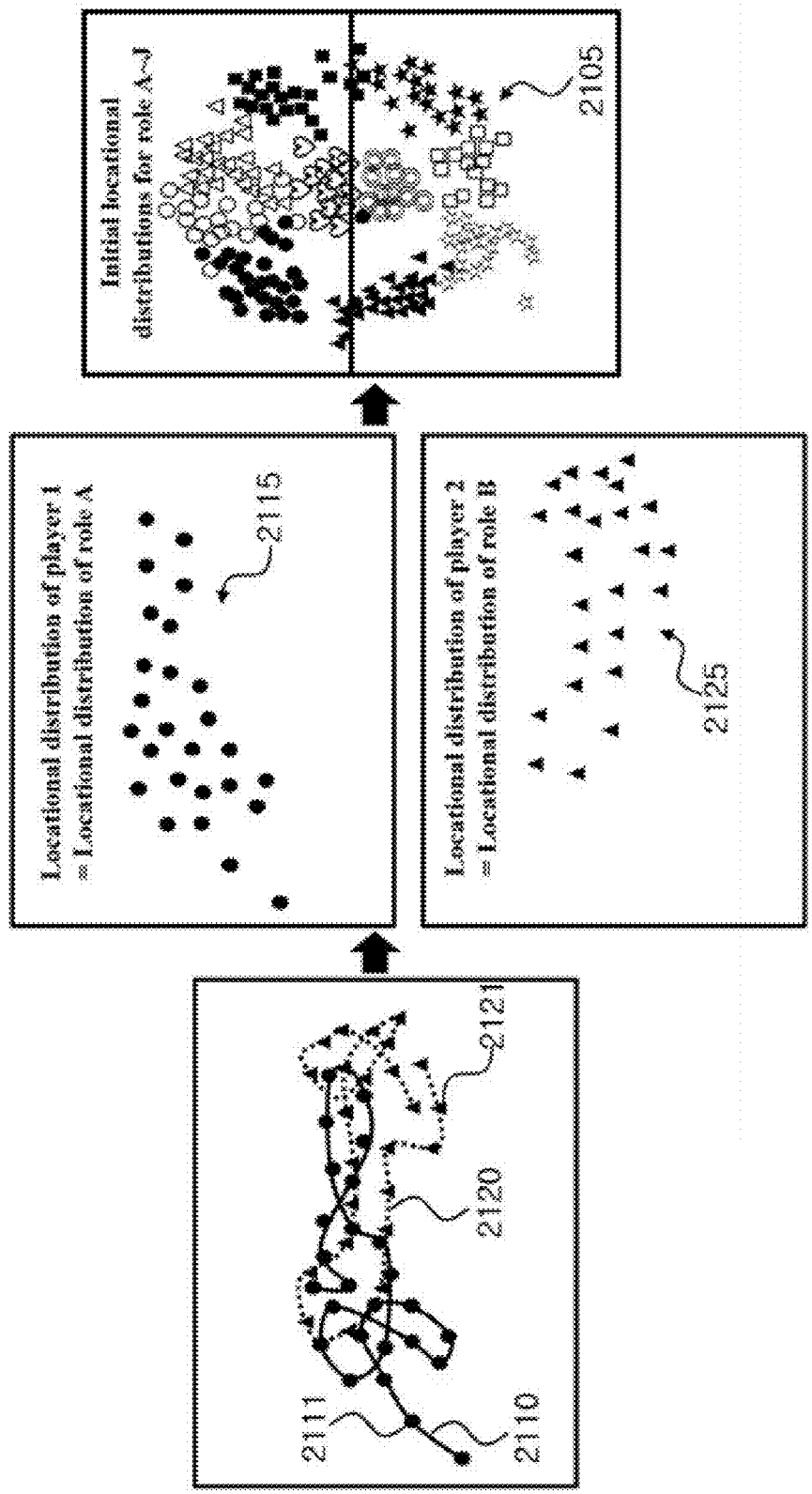
FIG. 22 shows an exemplary initial role assignment result.

In this regard, FIG. 21 is an example of an initial role assignment table based on player tracking data, and FIG. 22 shows an exemplary initial role assignment result. An initial role assignment will be described below with reference to FIGS. 21 and 22.

In the operation of acquiring role assignment information for the first time (S1930) after the player tracking data set is acquired (S1920), a player tracking data set for the player-wise location distribution is secured, but a space information set for the role-wise location distribution is not secured. That is, for example, the locations of a first player (Player 1) at each time point may be known, but the locations of role A at each time point may not be known at all.

For example, when role A is CF, Player 1 may play the CF role in the first half, and Player 2 may play the CF role in the second half. In this case, the location distribution of CF may be a set of location data of Player 1 in the first half (e.g., the locations of Player 1 from first to $36,000^{th}$ time points) and location data of Player 2 in the second half (e.g., the locations of Player 2 from $36,001^{th}$ to $72,000^{th}$ time points).

However, in the operation of acquiring role assignment information for the first time (S1930) after the player tracking data set is acquired (S1920), it is not known which player is performing the CF position at which time point, and thus a fixed role may be temporarily assigned to each player. For example, it can be assumed that Player 1 and Player 2 perform role A and role B through the target session, respectively.

As shown in FIG. 22, a trajectory 2110 of the first player may include the locations 2111 of the first player measured at each of the plurality of time points, and a trajectory 2120 of the second player may include the locations 2121 of the second player measured at each of the plurality of time points. Here, when, for example, role A is temporarily assigned to the first player and role B is temporarily assigned to the second player, a location distribution 2115 for the first player is the same as a location distribution 2115 of role A, and a location distribution 2125 for the second player is the same as a location distribution 2125 of role B.

As shown in FIG. 21, when roles A to J are temporarily assigned to the first to tenth players, respectively, the same role assignment as the temporary assignment is performed at all time points.

Accordingly, as shown in 22, for each of the roles A to J, an initial role-wise location distribution 2105 may be acquired.

When the initial role-wise location distribution is acquired according to the temporary role assignment for the player tracking data set, role assignment information may be acquired by performing role assignment to each player on a frame-by-frame basis on the player tracking data set and the initial role-wise location distribution, for example, through a Hungarian algorithm, as described above. However, the algorithm for assigning roles to players is not limited to the Hungarian algorithm, and for example, the assignment of a role to each player may be performed in a manner that minimizes a cost for each of the plurality of players.

For convenience of description, a simplified assignment procedure is exemplified. For example, when ten roles are assigned to ten players in a non-overlapping manner, the role assignment may be performed such that a cost for each player is minimized Here, the cost may be, for example, assigning roles to players such that the sum of the distances between a representative location of a specific role and the locations of the players in a corresponding frame is minimized. The representative location of the specific role may be, for example, the average location of the specific role over the target period. That is, when, for example, ten roles are assigned to ten players, it may be determined that an optimal assignment has been made when the sum of the distances between the ten players and the average location of the ten roles assigned to the players is minimized.

Figure 23:
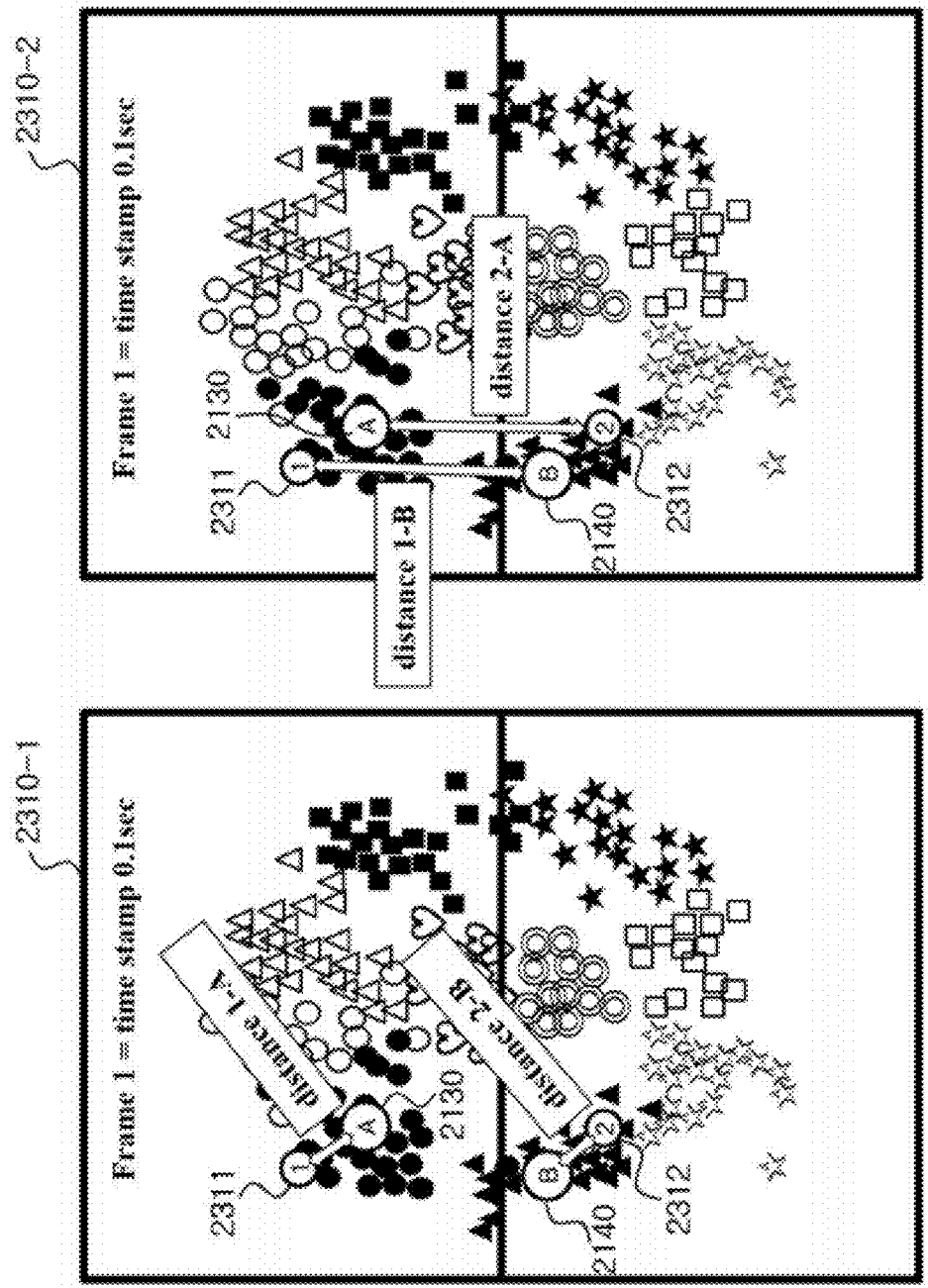
FIG. 23 shows role assignment considering the distance between a player location and a role location.

In this regard, FIG. 23 shows role assignment considering the distance between a player location and a role location. As shown in FIG. 23, in a first frame, for example, at a time point for a timestamp of 0.1 sec, a first assignment example 2310-1 and a second assignment example 2310-2 may be reviewed.

In the first assignment example 2310-1, it is assumed that role A is assigned to the first player and role B is assigned to the second player. In the second assignment example 2310-2, it is assumed that role B is assigned to the first player and role A is assigned to the second player.

In the first assignment example 2310-1, the sum of the distance between the representative location 2130 of role A and the location 2311 of the first player in the first frame and the distance between the representative location 2140 of role B and the location 2312 of the second player in the first frame may be calculated to determine a cost for the first assignment example 2310-1. In the second assignment example 2310-2, the sum of the distance between the representative location 2130 of role A and the location 2312 of the second player in the first frame and the distance between the representative location 2140 of role B and the location 2311 of the first player in the first frame may be calculated to determine a cost for the second assignment example 2310-2.

Since the cost in the first assignment example 2130-1 is smaller than the cost in the second assignment example 2310-2, role A may be assigned to the first player and role B may be assigned to the second player according to the first assignment example 2130-1 in the first frame.

FIG. 23 shows, as an example, assignments to the first player and the second player for convenience of description, but it has been previously described that a role is assigned to each of a plurality of players participating in a team sport at a corresponding time point.

Figure 24A:
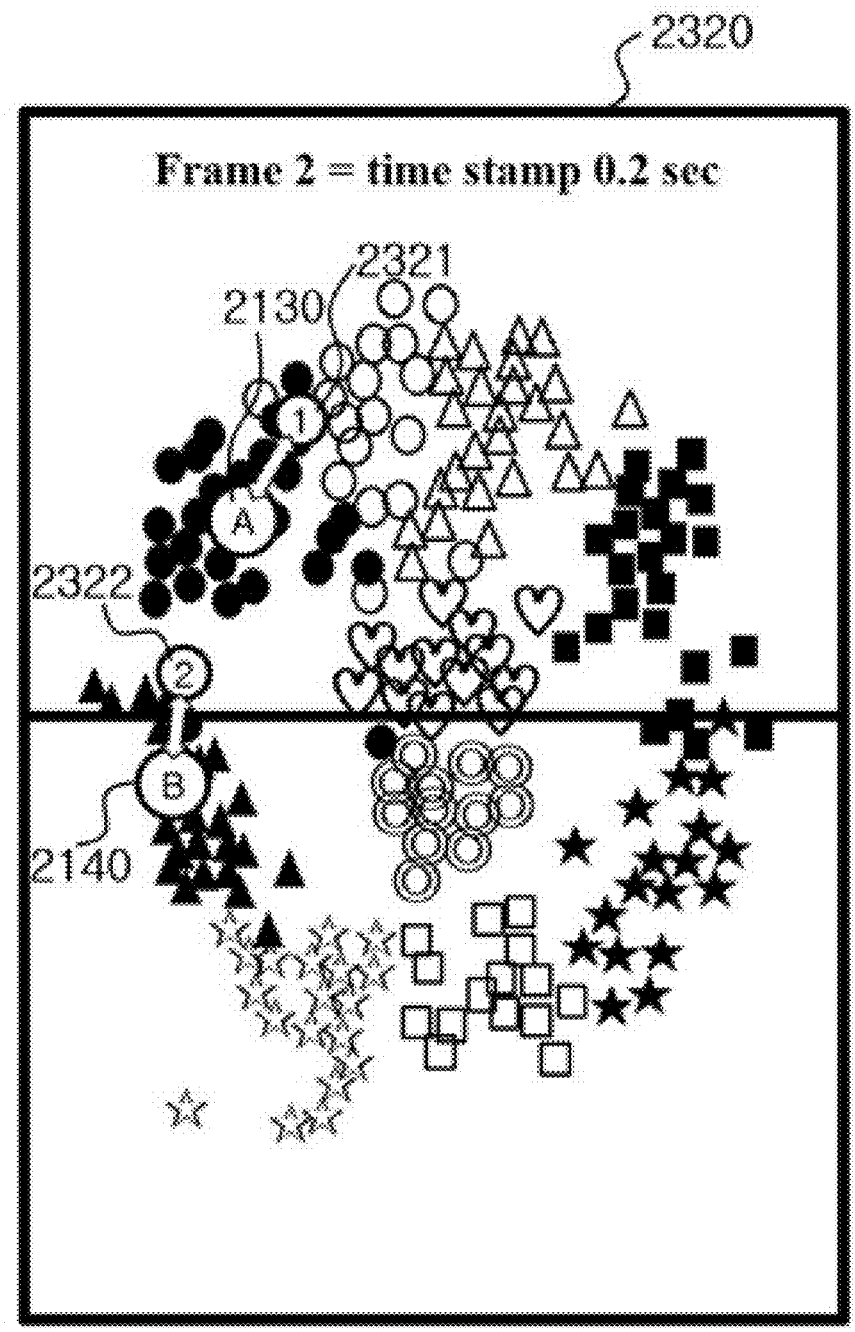
FIGS. 24A to 24C show a role assignment change at each of a plurality of time points.
Figure 24B:
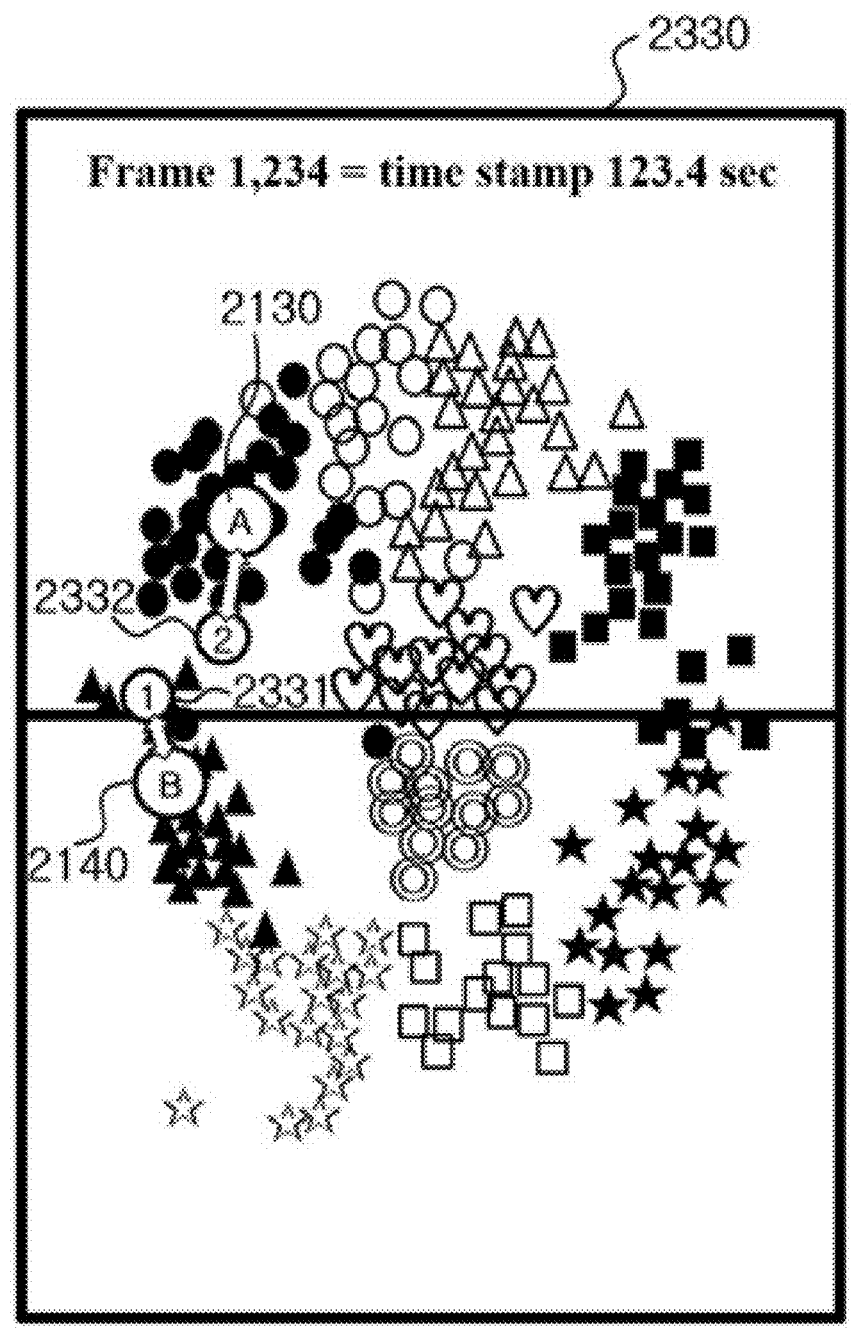
Figure 24C:
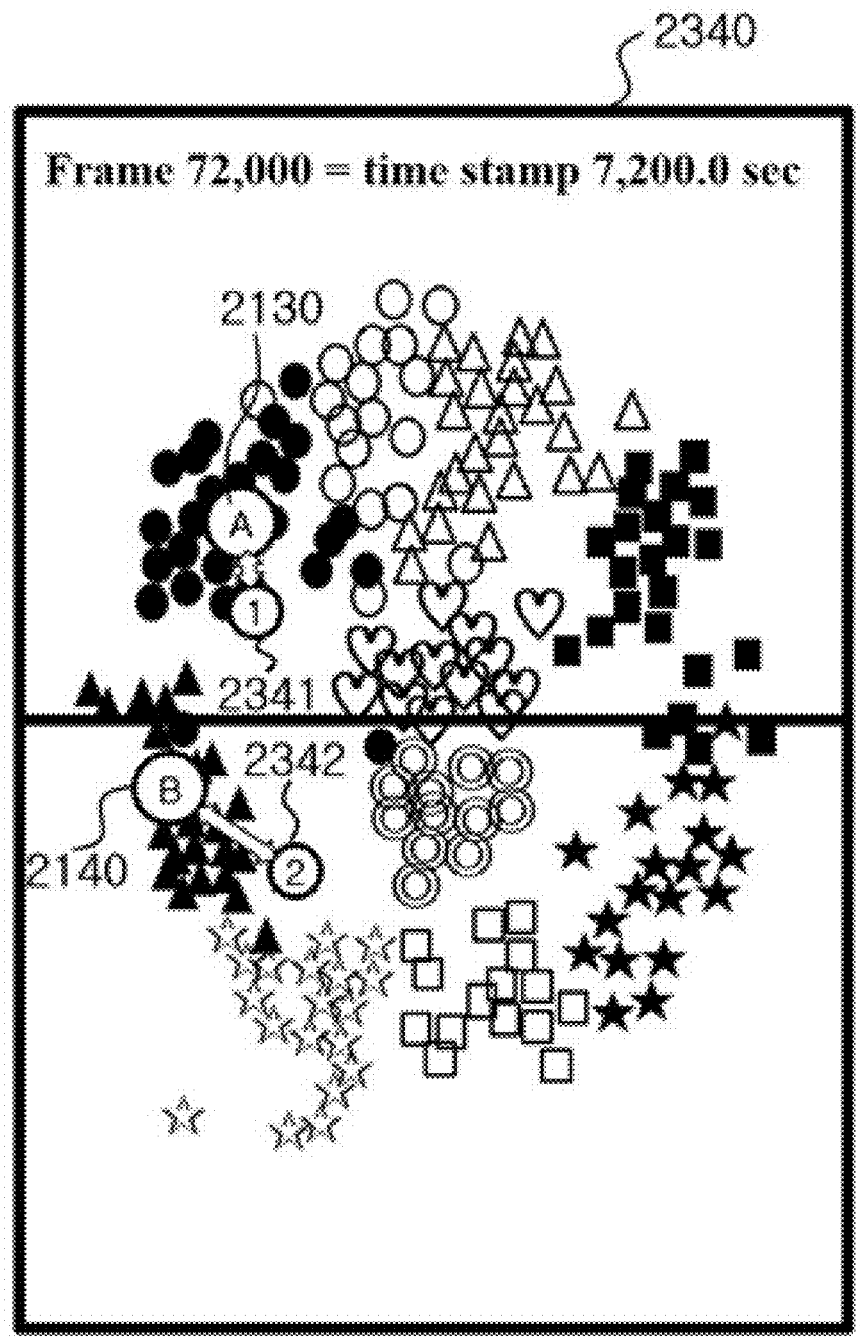

Also, role assignment may be performed at each of a plurality of time points included in a target period to be analyzed, i.e., for each frame. FIGS. 24A to 24C show a change in role assignment at each of a plurality of time points.

FIG. 24A illustrates role assignments 2320 to a first player and a second player in a second frame. In the second frame, a cost corresponding to the sum of the distance between the representative location 2130 of role A and the location 2321 of the first player in the second frame and the distance between the representative location 2140 of role B and the location 2322 of the second player in the second frame is smallest, and thus role A and role B may be assigned to the first player and the second player, respectively.

However, in the case of role assignment 2330 shown in FIG. 24b which is applied to the first player and the second player in the $1{,}234^{th}$ frame, a cost corresponding to the sum of the distance between the representative location 2130 of role A in the $1{,}234^{th}$ frame and the location 2332 of the second player in the $1{,}234^{th}$ frame and the distance between the representative location 2140 of role B and the location 2331 of the first player in the $1{,}234^{th}$ frame is smallest. Thus, role B may be assigned to the first player, and role A may be assigned to the second player.

Referring back to FIG. 24C, the role assignments 2340 to the first player and the second player in the $72{,}000^{th}$ frame are shown. In the $72{,}000^{th}$ frame, a cost corresponding to the sum of the distance between the representative location 2130 of role A and the location 2341 of the first player in the $72{,}000^{th}$ frame and the distance between the representative location 2140 of role B and the location 2342 of the second player in the $72{,}000^{th}$ frame is smallest, and thus role A and role B may be assigned to the first player and the second player, respectively. FIG. 25 shows an example of a changed role at the time of role assignment change. As described with reference to FIGS. 24A to 24C, referring to a result of the role assignment for the first player and the second player, role A is assigned to the first player, and role B is assigned to the second player at a timestamp of 0.1. However, role B is assigned to the first player, and role A is assigned to the second player in the case of role assignment 2510 at a timestamp of 123.4, and then role A and role B may be assigned back to the first player and the second player, respectively, in the case of role assignment 2520 at a timestamp of 7,200.0.

FIG. 26 is an example of the entire role assignment including a role assignment change section. As shown in FIG. 26, a regular situation in which role A and role B are assigned to the first player and the second player may be during a first period 2610. However, a position switch may occur between the first player and the second player at a first time point 2621. The position switch may include, for example, a situation in which the first player keeps empty space of the second player due to the overlapping of the second player. Accordingly, the first player and the second player may swap roles during a second period 2620 from the first time point 2621 to a second time point 2623. Role B may be assigned to the first player, and role A may be assigned to the second player (see 2625). At the second time point 2623, the position switch is completed, and a regular situation in which role A and role B are assigned to the first player and the second player, respectively, may be provided during a third period 2630.

By performing role assignment for each of the plurality of players at each of the plurality of time points included in the target period to be analyzed, with a similar effect to that described above by exemplifying the first and second players, the operation of acquiring role assignment information as shown in FIG. 19 may be accomplished. That is, information on which role index (e.g., role A) is assigned to which player (e.g., a first player) may be acquired at each of a plurality of time points within the target period.

Referring back to FIG. 19, the computing device may acquire a space information set (S1960). Specifically, the computing device may acquire a plurality of space information sets associated with a target period for each of a plurality of role indices based on the previously acquired role assignment information and player tracking data sets.

For example, a space information set for the role index of role A may include information on location data of role A at each of the plurality of time points within the target period. Since an initial role-wise location distribution used for the acquisition of role assignment information (S1930) of FIG. 19 is that an arbitrary role index is assigned to a player-wise location distribution, an initial role-wise location distribution for one role identifier includes only location data of one player. However, for example, role B rather than role A may be assigned to the first player in the operation of acquiring role assignment information (S1940) of FIG. 19. Like this, the locations of the plurality of players may be included in a space information set for one role identifier after role assignment is performed based on the initial role-wise location distribution.

Figure 27:
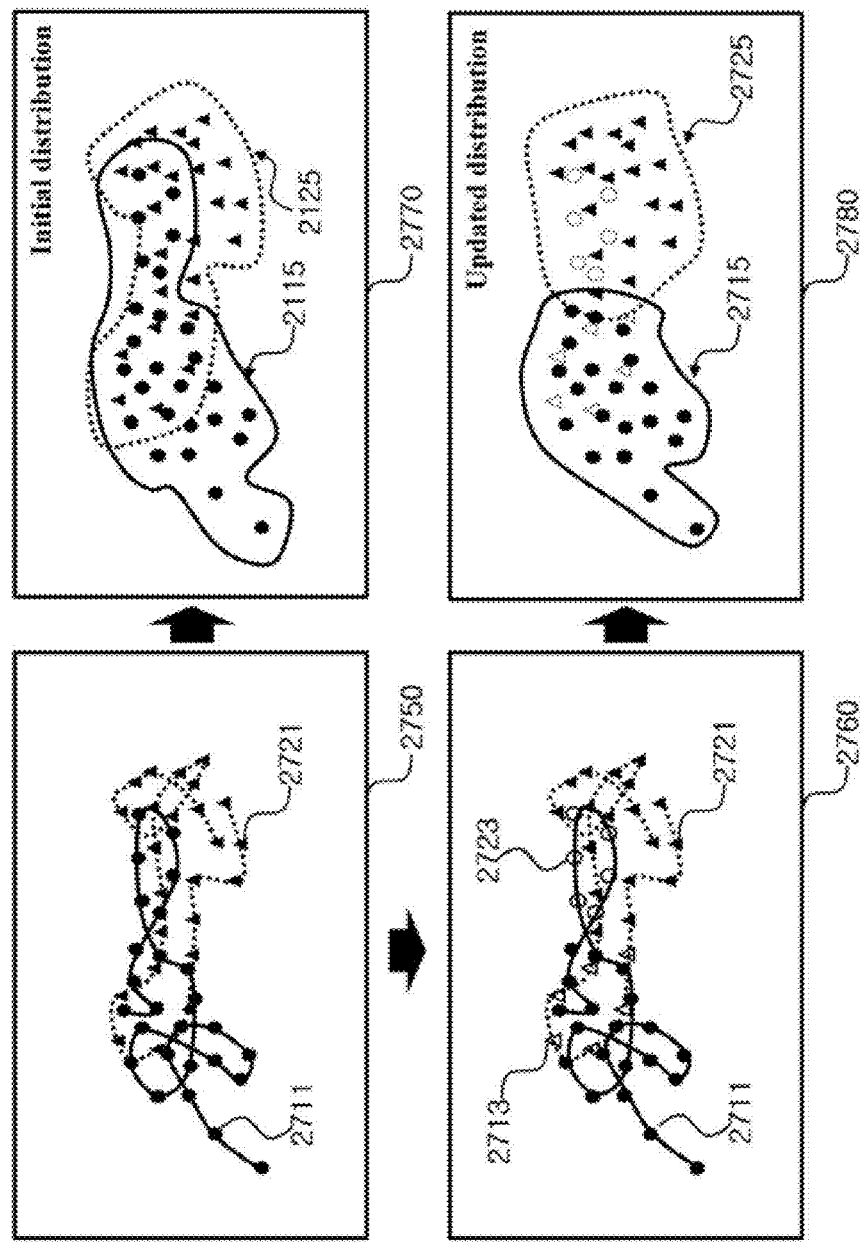
FIG. 27 shows the update of the space information set for each role through role assignment.
Figure 28:
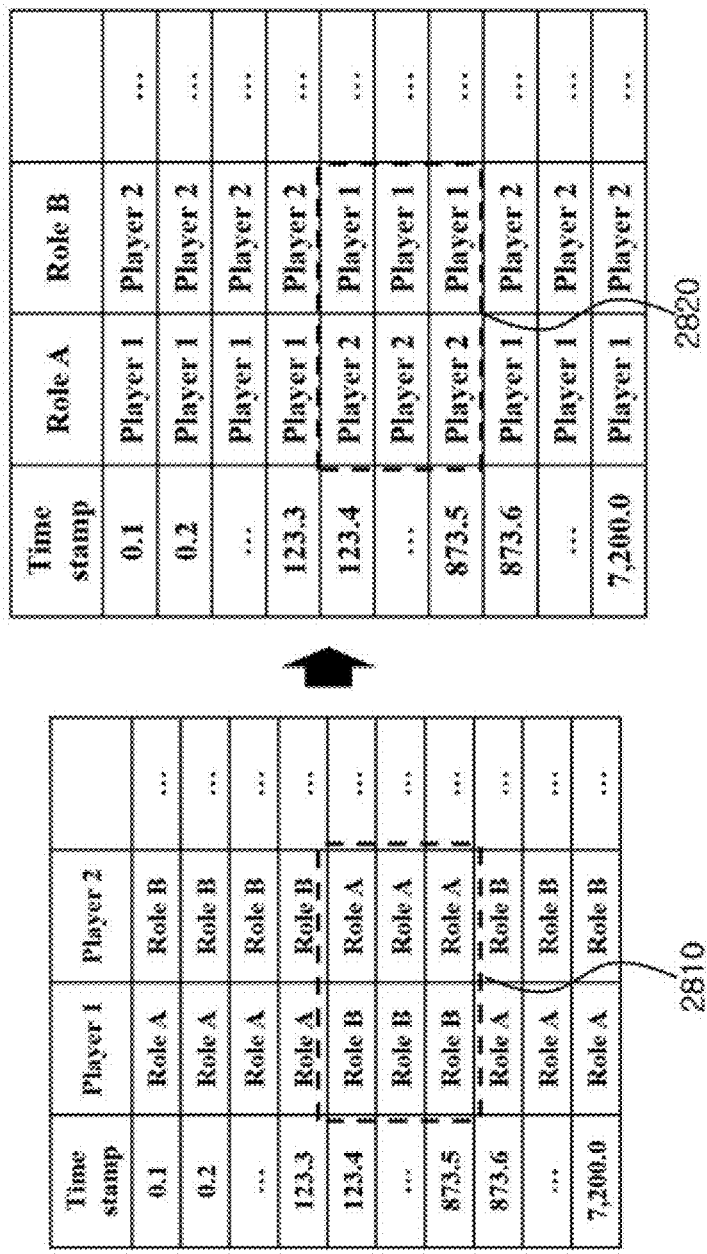
FIG. 28 is an example of a role assignment table indicating the update of the space information set of FIG. 27.

In this regard, FIG. 27 shows the update of the space information set for each role through role assignment, and FIG. 28 is an example of a role assignment table showing the update of the space information set of FIG. 27.

As shown in FIG. 27, while a role identifier is temporarily assigned to each of the plurality of players (2750), the location of role A includes the locations of the first player indicated by black circles 2711, and the location of role B includes the locations of the second player indicated by black triangles 2721. Therefore, referring to the initial role-wise location distribution 2770, the initial role-wise location distribution 2115 of role A is determined based on the location distribution of the first player, and the initial role-wise location distribution 2125 of role B is determined based on the location distribution of the second player.

Meanwhile, referring to a situation 2760 after roles are assigned to players at each time point by the operation of acquiring role assignment information (S1930) of FIG. 19, the locations of role A may include locations which are indicated by black circles 2711 and where role A is assigned to the first player and locations which are indicated by white triangles 2713 and where role A is assigned to the second player. Also, the locations of role B may include locations which are indicated by black triangles 2721 and where role B is assigned to the second player and locations which are indicated by white circles 2723 and where role B is assigned to the first player. Therefore, referring to the updated role-wise location distribution 2780, the role-wise location distribution 2715 of role A has a more concentrated form than the initial role-wise location distribution 2115 of role A, and the role-wise location distribution 2725 of role B has a more concentrated form than the initial role-wise location distribution 2125 of role B.

In other words, when the role assignment for each player on a frame-by-frame basis based on the initial role-wise location distribution is primarily completed, the location distributions of the roles may be updated based on the role assignment. In the initial role-wise location distribution, the location distribution is obtained assuming that the first player and the second player perform role A and role B in a fixed manner throughout the target period, respectively. However, after the role assignment for each player is completed on a frame-by-frame basis, a role-wise location distribution may be recalculated using the acquired role assignment and player tracking data.

For example, referring to the role assignment shown in FIG. 28, it can be seen that, in alignment by players, role B is assigned to the first player and role A is assigned to the second player in a first time section 2810. Accordingly, in alignment by roles, the location of role A may be the location of the first player and the location of role B may be the location of the second player in the first time section 2820.

More specifically, with respect to role A, the first player performs role A in the first to $1,233^{rd}$ and $8,736^{th}$ to $72,000^{th}$ frames, and the second player performs role A in the $1,234^{th}$ to $8,735^{th}$ frames. Thus, the role-wise location distribution of role A may be composed of the locations of the first player in the first to $1,233^{rd}$ and $8,736^{th}$ to $72,000^{th}$ frames and the locations of the second player in the $1,234^{th}$ to $8,735^{th}$ frames.

The role-wise space information sets acquired in the operation of acquiring a space information set of FIG. 19 (S1960) may each include a role-wise location distribution reflecting role assignment according to the role assignment information acquisition operation (S1930) as described above. Space information sets for each of the role indices acquired based on a role assignment result may include an updated role-wise location distribution that is more concentrated and better represents the location of a corresponding role than the initial role-wise location distribution corresponding to the temporary role assignment.

Meanwhile, according to an aspect of the present disclosure, a role assignment corresponding to noise may be eliminated from among role assignments at a plurality of time points, and a space information set for each role may be acquired using only the remaining valid role assignments. In other words, the elimination of noise components may also be performed when the role-wise location distribution is updated in the operation of acquiring a space information set (S1960).

The role-wise location distribution is acquired to indicate the location characteristics of the corresponding role. For example, in team sports such as soccer or basketball, the movements of players are very fluid, and a situation may arise in which the formations or player positions of teams participating in team sports have collapsed and the distinction is meaningless. A typical example of the situation in which the formations or positions have collapsed is a set-piece situation such as a corner kick or a free kick. When the role-wise location distribution is updated while the situation in which formations or positions have collapsed is excluded as noise, the location characteristics of the corresponding role can be more accurately reflected in the role-wise location distribution, and thus it is possible to improve the accuracy of tactical analysis for various team sports.

In particular, when the target session is divided into at least two time sections (S1910) and a space information set is acquired for the sections (S1960) according to an aspect of the present disclosure, the need for noise elimination and the effect of improving accuracy may be increased. As exemplified above, under the assumption that the entire session for a team sport is 120 minutes, when an analysis is performed on the entire session without separate time period division, for example, even if an analysis is performed including a set-piece situation for about 10 minutes, the accuracy of analysis of a given role may not be significantly affected. However, when a target session is divided according to a predetermined criterion, such as a change point of a formation or a change point of a role, one time section may have a short time length of about 20 minutes. When repeated set-piece situations occur continuously in a short time section of 20 minutes, set-piece situations longer than 10 minutes are included as noise situations, and thus the accuracy of tactical analysis based on the role-wise location distribution during the entire section of 20 minutes may be very low. Accordingly, when the target session is divided into at least two time sections (S1910) and a space information set is acquired for the sections (S1960) according to an aspect of the present disclosure, it is required to eliminate noise situations to update the role-wise location distribution.

The noise to be eliminated may be referred to herein as an "irregular situation." In this regard, FIG. 29 is an example of a role assignment table for determining an irregular role assignment, and FIG. 30 is an example of determining a switch ratio according to the role assignment table of FIG. 29. The determination of an irregular role assignment according to an embodiment of the present disclosure will be described below with reference to FIGS. 29 and 30.

As shown in FIG. 19, before acquiring the space information set (S1960), the computing device may be configured to determine a dominant role assignment (S1940), determine an irregular role assignment (S1950), and acquire a plurality of space information sets associated with a target period for each of a plurality of role indices based on the remaining role assignment information other than at least one irregular role assignment and some of the player tracking data sets corresponding to the remaining role assignment information (S1960).

That is, when the plurality of role assignments for the plurality of time points are acquired through the role assignment information acquisition operation (S1930), the computing device may determine a dominant role assignment based on the plurality of role assignments (S1940). According to an aspect, the dominant role assignment may be the most frequent role assignment among the plurality of role assignments. As exemplarily shown in FIG. 29, like that at the first time point 2910, a role assignment in which roles A to J are assigned to the first to tenth players, respectively, occurs with the highest frequency in the entire time section to be analyzed. Thus, the role assignment in which roles A to J are assigned to the first to tenth players, respectively, may be determined as a dominant role assignment. However, the determination of the dominant role assignment is not limited to the most frequent role assignment, and it should be understood that various selection criteria for dominant role assignments are applicable.

Subsequently, as shown in FIG. 19, the computing device may determine at least one irregular role assignment from the plurality of role assignments in consideration of the dominant role assignment (S1950).

As shown more specifically in FIG. 20, the operation of determining an irregular role assignment (S1950) may include operations of acquiring distance information between the dominant role assignment and each role assignment (S1951) and determining an irregular role assignment based on the distance information (S1953).

The computing device may acquire information on the distance from the dominant role assignment to each of the plurality of role assignments (S1951). Here, the distance may reflect the degree of difference between the dominant role assignment and each of the plurality of role assignments. Also, according to an aspect, the distance may be a switch ratio from the dominant role assignment with respect to each of the plurality of role assignments.

More specifically, the computing device may determine the degree of difference between the dominant role assignment and each of the role assignments for the plurality of time points included in the target period. The role assignments of time points included in the second period 2920 of FIG. 29 are role assignments in which the role of the first player and the role of the second player are role B and role A, respectively, unlike the dominant role assignment, and may not be significantly different from the dominant role assignment. On the other hand, it can be seen that the role assignments of time points included in the third period 2930 of FIG. 29 are substantially different from the dominant role assignment in terms of the roles assigned to the players.

The degree of difference between the dominant role assignment and each role assignment may be represented as a switch ratio calculated based on the number of different roles. Referring to FIG. 30, the roles of the first player and the second player at all the time points included in the second period 2920 are different from those of the dominant role assignment, and the switch ratio may be 20%. On the other hand, referring to the time points included in the third period 2930, it can be seen that the switch ratio is 70% or more because seven or more players have different roles from those of the dominant role assignment.

Referring to FIG. 20, the computing device may determine an irregular role assignment based on the information on the distances from each role assignment to the dominant role assignment (S1953). For example, when the switch ratio is 70% or more, a corresponding frame may be considered as an irregular situation, which may be excluded when the role-wise location distribution is being updated. Referring to the example of FIG. 30, the role assignments corresponding to the time points included in the second period 2920 have a switch ratio of 20% and thus are not included in the irregular situation. However, the role assignments corresponding to the time points included in the third period 2930 all have a switch ratio of 70% or more. Thus, the corresponding role assignments may be regarded as irregular situations, and the location of the role according to the corresponding time point may not be taken into account in updating the role-wise location distribution.

That is, referring back to FIG. 19, the computing device may acquire a plurality of space information sets associated with a target period for each of a plurality of role indices based on the remaining role assignment information other than at least one irregular role assignment and some of the player tracking data sets corresponding to the remaining role assignment information (S1960). According to the remaining role assignment information other than the irregular role assignment, it is possible to know which role index is assigned to which player at each time point corresponding to a regular situation, and it is also possible to know locations at corresponding time points of a corresponding player through the player tracking data set. Thus, it is possible to know the locations of the roles at each time point corresponding to the regular situation. Accordingly, the computing device may acquire a plurality of space information sets for each role including a sequence of location data at each time point in a target session of the corresponding role.

Figure 31:
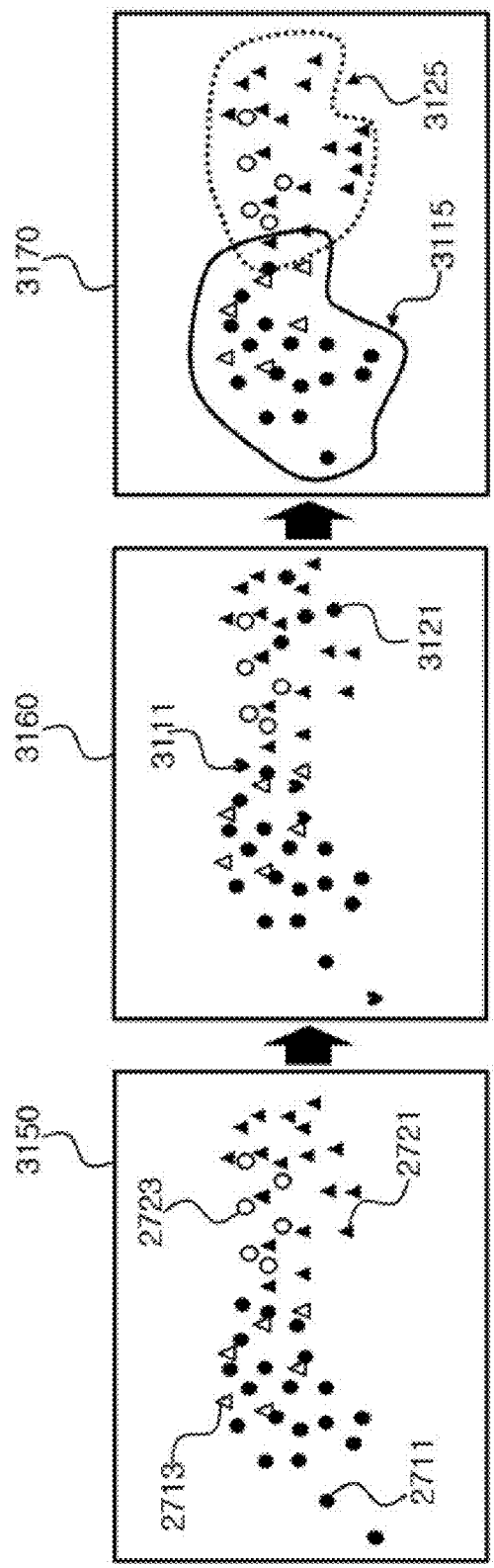
FIG. 31 shows the update of the space information set for each role according to the elimination of irregular frames.
Figure 32:
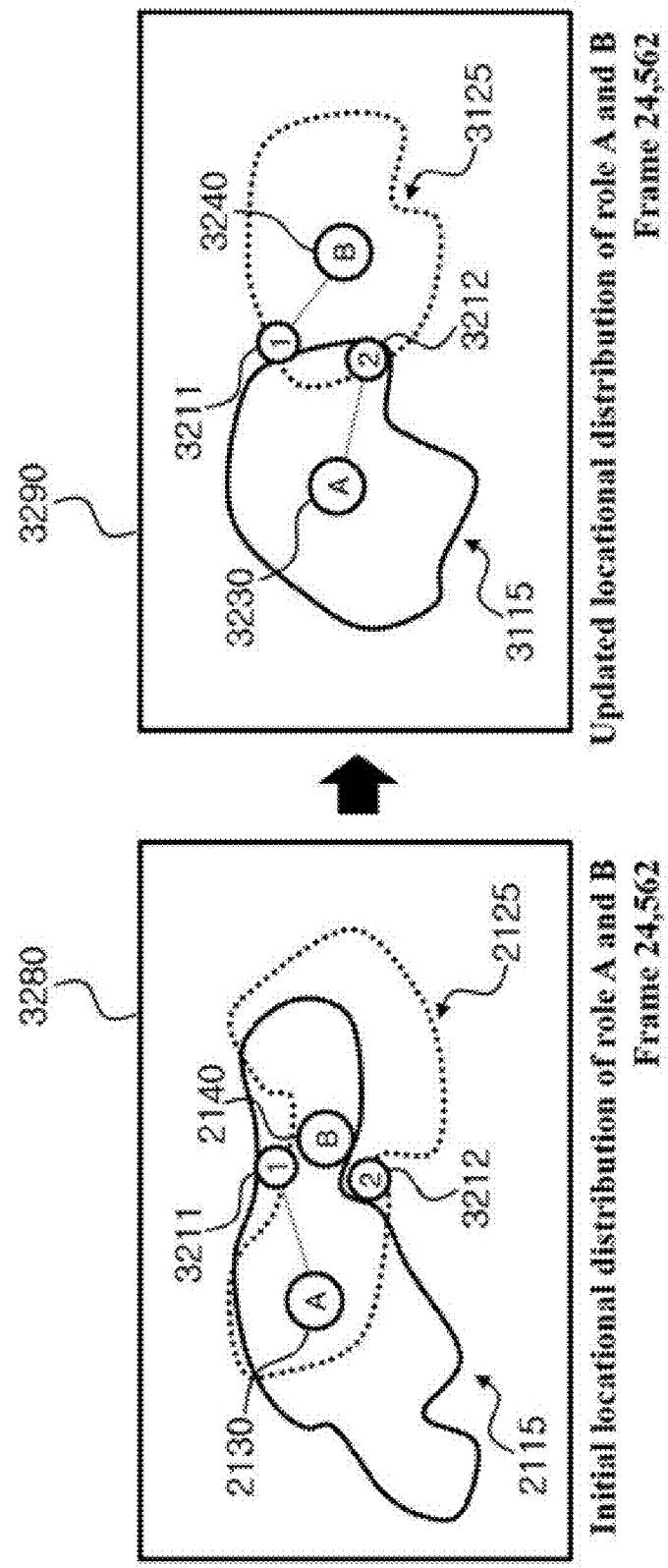
FIG. 32 exemplarily illustrates that role assignment changes at the same time according to the update of the space information set of FIG. 31.

FIG. 31 shows the update of the space information set for each role through the elimination of irregular frames, and FIG. 32 illustrates that a role assignment is changed at the same time point according to the update of the space information set of FIG. 31. The effects of elimination of irregular situations will be described below with reference to FIGS. 31 and 32.

As shown in FIG. 31, referring to the role-wise location distribution 3150 before the determination of irregular frames, the locations of role A may include locations which are indicated by black circles 2711 and where role A is assigned to the first player and locations which are indicated by white triangles 2713 and where role A is assigned to the second player, as described with reference to FIG. 27. Also, the locations of role B may include locations which are indicated by black triangles 2721 and where role B is assigned to the second player and locations which are indicated by white circles 2723 and where role B is assigned to the first player.

Subsequently, referring to a situation after the determination of irregular frames (3160), locations corresponding to noise may be eliminated from the locations of role A as indicated by black hearts 3111, and locations corresponding to noise may be eliminated from the locations of role B as indicated by black crosses 3121. In FIG. 31, for convenience of description, it is shown that noise occurs when player 1 performs role A or role B, but in reality, it may be determined that not only roles A and B but also any other roles are performed at the time of formation collapse corresponding to noise.

As a result, referring to a denoised role-wise location distribution 3170, the role-wise location distribution 3115 of role A has a more concentrated form than either of the initial role-wise location distribution 2115 of role A and the updated role-wise location distribution 2715 of FIG. 27, and the role-wise location distribution 3125 of role B has a more concentrated form than either of the initial role-wise location distribution 2125 of role B and the updated role-wise location distribution 2725 of FIG. 27. Accordingly, the role-wise location distribution of each role may better represent the location characteristics of the corresponding role.

Referring to FIG. 32, even for the location of the same player at the same time point, it can be seen that the role assignment according to the initial role-wise location distribution is different from the role assignment based on the denoised role-wise location distribution.

More specifically, referring to role assignment 3280 according to an initial role-wise location distribution, role assignment may be performed based on the initial role-wise location distribution 2115 of role A and the initial role-wise location distribution 2125 of role B. A cost determined by calculating the sum of the distance between the representative location 2130 of role A and the location 3211 of the first player in the $24{,}562^{nd}$ frame and the distance between the representative location 2140 of role B and the location 3212 of the second player in the $24{,}562^{nd}$ frame is lowest, and thus in the $24{,}562^{nd}$ frame in the role assignment 3280 according to the initial role-wise location distribution, role A may be assigned to the first player, and role B may be assigned to the second player.

On the other hand, referring to role assignment 3290 according to the denoised role-wise location distribution, the role assignment may be performed based on the role-wise location distribution 3115 updated by reflecting the noise of role A and the role-wise location distribution 3125 updated by reflecting the noise of role B. A cost determined by calculating the sum of the distance between the representative location 3230 of role A and the location 3212 of the second player in the $24{,}562^{nd}$ frame and the distance between the representative location 3240 of role B and the location 3211 of the first player in the $24{,}562^{nd}$ frame is lowest, and thus in the $24{,}562^{nd}$ frame in the role assignment 3290 according to the denoised role-wise location distribution, role B may be assigned to the first player, and role A may be assigned to the second player.

In other words, different role assignments may occur according to the use of the role-wise location distribution updated through denoising for the same player in the same frame. This can help improve the accuracy of tactical analysis by better reflecting the location distribution of the corresponding role.

Referring back to FIG. 19, the computing device may update role assignment information using a plurality of space information sets (S1970). That is, by reassigning roles to a plurality of players using role assignment information acquired based on the initial role-wise location distribution, and space information sets for each denoised role according to an aspect, the computing device may update the role assignment information. According to an aspect of the present disclosure, the operations of determining a dominant role assignment (S1940), determining an irregular role assignment (S1950), acquiring a space information set based on the remaining role assignment information other than the irregular role assignment (S1960), and updating the role assignment information may be repeatedly performed until a predetermined condition is satisfied.

That is, a process of performing role assignment and noise removal for players based on a role-wise location distribution of each role and with improved accuracy, acquiring a role-wise location distribution with more improved accuracy, performing player role assignment and noise removal, acquiring a more updated role-wise location distribution, and then performing role reassignment to each player may be repeated.

In this iterative process, as described with reference to FIG. 32, in the role assignment performed based on the changed role-wise location distribution, different roles may be assigned to the same player in the same frame. However, this change of role assignment does not occur for all players in all frames, and as the update of the role assignment and the update of the space information set are repeated, the number of frames where the role assignment changes or the number of players for whom role assignment changes may decrease, and further reassignment may not change the roles assigned to the players.

In this regard, as shown in FIG. 19, the computing device may determine whether an additional update of a plurality of space information sets or role assignment information is required (S1980). When it is determined that the additional update of space information sets or role assignment information is required according to a predetermined criterion, the computing device may perform the additional update of the role assignment information by acquiring a space information set based on previously updated role assignment information and performing role assignment for each player. When it is determined that the additional update of space information sets or role assignment information is not required according to the predetermined criterion, the computing device may calculate a role-wise location distribution based on role assignment information corresponding to the last role assignment information update, and finally may acquire a space information set for each role.

According to an aspect of the present disclosure, the computing device may determine whether the additional update is required based on whether at least a portion of the role assignment information has been changed by the operation of updating the previous role assignment information. For example, when the role assignment information has not been changed at all by the operation of updating the previous role assignment information, the computing device may determine that the update procedure for the role assignment information is converged and determine that no additional update is required. In this case, the previous space information set may be determined as a final space information set.

However, there may be cases in which convergence does not occur despite repetitive role assignments. In this regard, according to an aspect of the present disclosure, the computing device may determine whether the additional update is required based on whether the number of time points at which role assignment is changed by the operation of updating the previous role assignment information is less than or equal to a predetermined threshold value. For example, when the number of time points at which a change occurs in role assignment before an update by the operation of updating the previous role assignment information, among a plurality of time points included in a target period, is greater than or equal to a predetermined number, it may be determined that an additional update is still required. For example, when the entire sequence for the target session includes 72,000 time points, it may be determined that an additional update is performed until the role assignment is changed only at less than 1% of the total time points.

According to another aspect of the present disclosure, the computing device may determine whether an additional update is required based on whether a predetermined number of updates have been accomplished. For example, when the update of the role assignment has been completed 10 times, the computing device may terminate the role assignment process without performing any further updates.

In addition, by defining various numbers of repetitions or conditions, the computing device may repeat the update until a corresponding condition or number is satisfied.

When it is determined that the additional update is no longer necessary, finally, role assignment information of each of the players at all the time points is acquired, and space information sets including a sequence of location data at a plurality of time points for each of the roles may be acquired.

Meanwhile, a device for providing tactical information for team sports according to an aspect of the present disclosure may include a processor and a memory, wherein the processor may be configured to acquire a plurality of player tracking data sets for a plurality of players, wherein each of the player tracking data sets includes a sequence of location data of a corresponding player during a target period; acquire role assignment information using the plurality of player tracking data sets, wherein the role assignment information includes a plurality of role assignments for a plurality of time points in the target period and each of the role assignments indicates a plurality of role indices assigned to the plurality of players at a corresponding time point; determine a dominant role assignment based on the plurality of role assignments; determine at least one irregular role assignment from the plurality of role assignments in consideration of the dominant role assignment; acquire a plurality of space information sets associated with the target period for each of the plurality of role indices based on the remaining role assignment information other than the at least one irregular role assignment and some of the player tracking data sets corresponding to the remaining role assignment information; and update the role assignment information using the plurality of space information sets. A specific operation of the device for providing tactical information for team sports according to an aspect of the present disclosure may follow the above-described role assignment information acquisition process.

Division into Formation Periods

Figure 34:
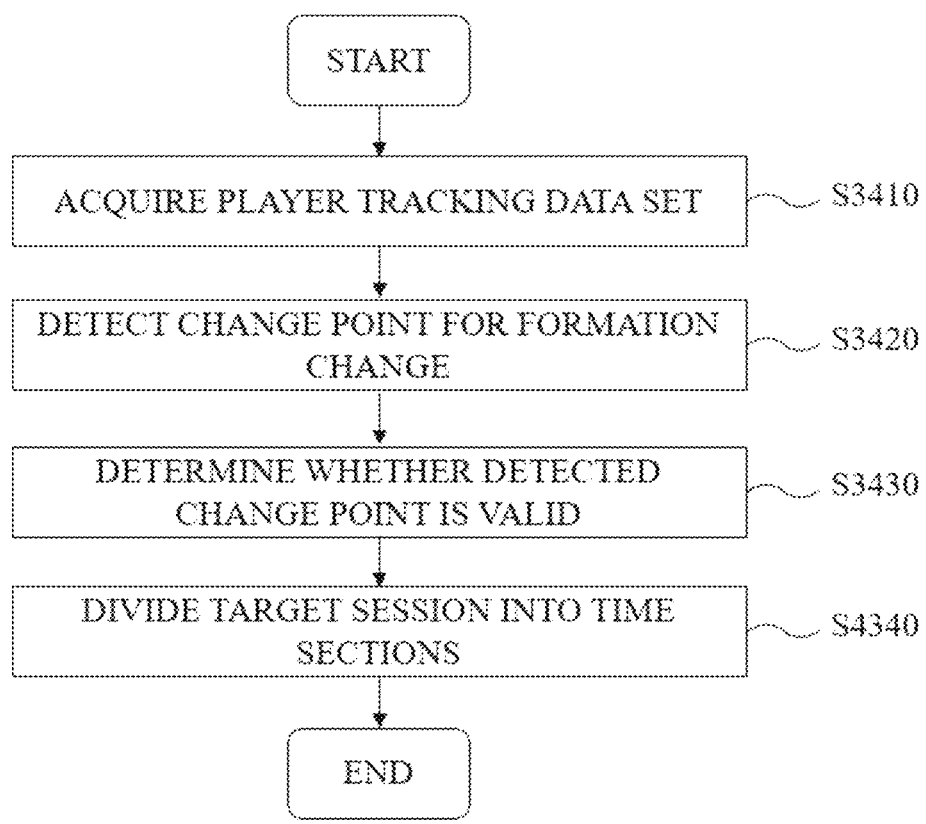
FIG. 34 is a schematic flowchart illustrating a formation time period division process according to an embodiment of the present disclosure.
Figure 35:
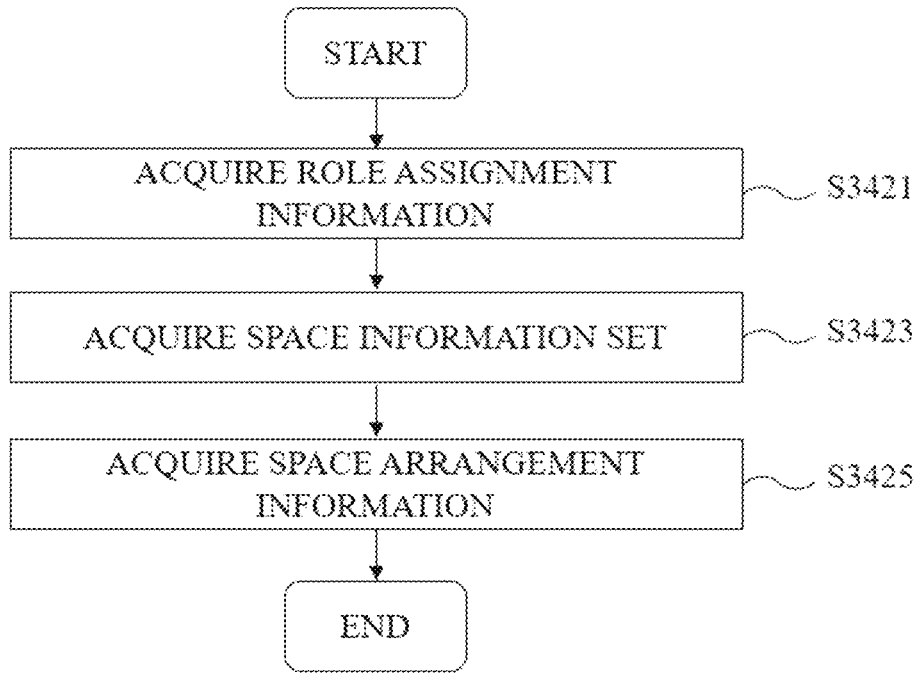
FIG. 35 is a detailed flowchart illustrating the acquisition of space arrangement information for a change point detection process of FIG. 34.
Figure 36:
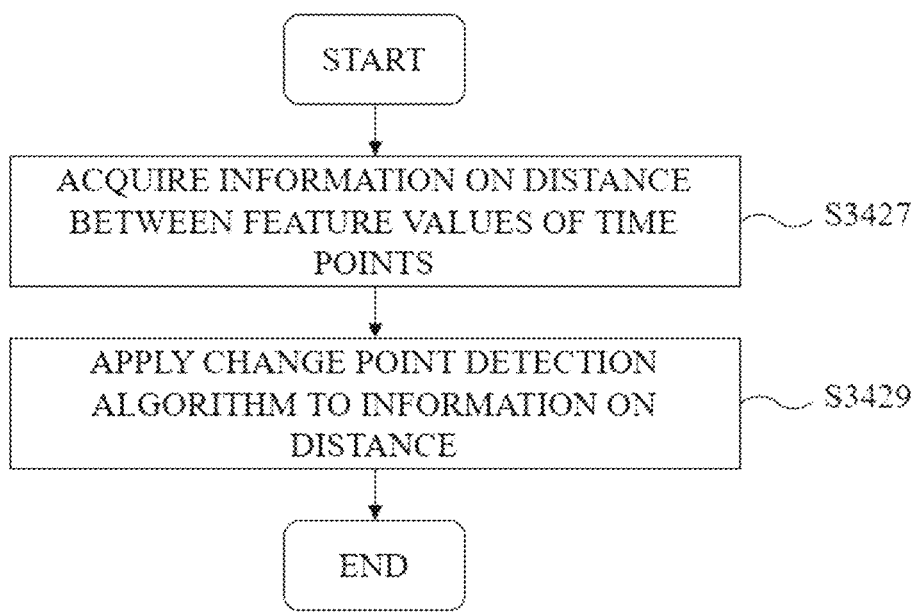
FIG. 36 is a detailed flowchart illustrating the acquisition of distance information for a change point detection process of FIG. 34.

FIG. 34 is a schematic flowchart illustrating a formation time period division process according to an embodiment of the present disclosure. FIG. 35 is a detailed flowchart illustrating the acquisition of space arrangement information for a change point detection process of FIG. 34. FIG. 36 is a detailed flowchart illustrating the acquisition of distance information for a change point detection process of FIG. 34. Division into formation periods according to an embodiment of the present disclosure will be described in more detail below with reference to FIGS. 34 to 36.

The method and/or processes according to an embodiment of the present disclosure may be performed by a computing device. According to an aspect, the computing device may be an analysis device 1400 as described with reference to FIG. 9, but the present disclosure is not limited thereto. Any device capable of computation with a processor and a memory may be used.

According to an embodiment of the present disclosure, for example, the computing device may divide a target session for one team sport game into at least two formation time sections with respect to a time point at which the team formation of a team participating in the team sport game is changed. When analyzing tactics for team sports, it is very important to analyze the formations of teams participating in team sports. Also, even when performing a more specific and high-dimensional analysis such as an analysis of a role change for at least some players in the formation, as well as the analysis of the team formation, a method of finding a time point at which the team formation of a team participating in the team sport is changed, dividing the session into formation sections, and performing a high-dimensional tactical analysis for the formation time sections may help to secure more accurate and meaningful tactical information.

Referring to FIG. 34, the formation period division process according to an embodiment of the present disclosure may include one or more of an operation of acquiring a player tracking data set (S3410), an operation of detecting a change point for a formation change (S3420), an operation of determining whether the detected change point is valid (S3430), and an operation of dividing a target session into time sections (S3440). The operations of this example will be described below.

As shown in FIG. 34, first, the computing device may acquire a player tracking data set (S3410). More specifically, the computing device may acquire a plurality of player tracking data sets for a plurality of players, and each of the player tracking data sets may include a sequence of location data of a corresponding player during a target session. A target to be divided into formation time periods may be a target session corresponding to the operating time of one team sport game. The computing device may acquire information on the locations of the players for each of a plurality of time points during the target session. It should be noted that the process for acquiring player tracking data according to an embodiment of the present disclosure described above with reference to FIG. 18 may be applied, but the present disclosure is not necessarily limited thereto.

Next, as shown in FIG. 34, the computing device may detect a change point for a formation change (S3420). More specifically, the computing device may generate feature values corresponding to each of the plurality of time points within the target session based on the plurality of player tracking data sets acquired previously and may apply a CPD algorithm to the feature values. As a result, the computing device may detect a change point indicating a time point at which the formation of a team participating in the target session is changed, from among the plurality of time points in the target session.

The division of the target session into at least two formation time periods may be performed by detecting a change point, which is a specific time point at which a formation change is performed, from among the plurality of time points included in the target session to be analyzed. Accordingly, in order to detect a change point, it may be required to generate feature values capable of reflecting different features for the plurality of time points included in the target session. When the feature values of the time points are generated, a change point detection based on the feature values may be accomplished by applying a predetermined change point detection algorithm to sequences of the feature values.

Here, for example, as described above in "3. Related Art" of the present disclosure, a non-parametric variable detection technique may be applied as the change point detection algorithm. More specifically, the change point detection algorithm may include a discrete g-segmentation algorithm. However, as also mentioned in "3. Related Art," the change point detection technique of the present disclosure is not limited to such a specific algorithm, and it should be understood that any CPD algorithm capable of detecting a change point of a characteristic based on a sequence of values to be determined may be used.

According to an aspect of the present disclosure, the feature values for the time points to which the change point detection algorithm is to be applied may be generated based on, for example, information on the location of a player or role at a corresponding time point or information on a location relationship between players or roles.

More specifically, the feature value for each of the plurality of time points may be generated based on at least one of the locations of the plurality of players at each time point, a player space arrangement at each time point, the locations of the plurality of roles at each time point, or a role space arrangement at each time point.

Since the player tracking data set is previously acquired (S3410), information on the locations of each of the plurality of players at each time point may be acquired. A feature value indicating the feature of each time point may be calculated based on the locations of the players placed at a corresponding time point. For example, the average location of all players at a corresponding time point may be determined as a feature value for the time point. By applying the change point detection algorithm to a sequence of the plurality of time points, a time point at which the average location of all players significantly changes may be detected as a change point indicating a formation change.

Meanwhile, a feature value indicating the feature of each time point may be generated based on a player space arrangement at each time point. The player space arrangement may reflect a location relationship between the players at each time point. As described above in the present disclosure, the feature value based on the player space arrangement may include, for example, player adjacency information calculated based on the adjacency between the players.

In another aspect, a feature value indicating a characteristic of a corresponding time point may be calculated based on the locations of roles at each time point, and for example, the average location of all roles at a corresponding time point may be determined as a feature value of the time point.

Also, a feature value indicating the feature of each time point may be generated based on a role space arrangement at a corresponding time point. The role space arrangement may reflect a location relationship between the roles at each time point. As will be described above in the present disclosure, the feature value based on the role space arrangement may include, for example, role adjacency information calculated based on the adjacency between the roles.

In the embodiments of the present disclosure, information used to generate the feature value of each time point is not limited to any one in terms of "player" or "role" and is not limited to any one in terms of "plurality of locations" or "space arrangement."

However, in terms of "player" or "role," as described above, "player" and "role" may be different from each other. In particular, when a player substitution in the target session or a position change indicated between players occurs, "role" may better reflect changes in positions constituting the formation.

Also, in terms of "plurality of locations" and "space arrangement," for example, in fluid team sports such as soccer or basketball, players change their locations very actively over the target session. Thus, irrespective of the change of the formation, various situations may occur in which the locations of the players or roles change. On the other hand, "space arrangement" that reflects the location relationship between the players or the location relationship between the roles may have much less change than the location of the player or role itself when the formation remains the same. Thus, "space arrangement" may be more advantageous in detecting a formation change than the location itself.

Although the feature values according to the embodiments of the present disclosure are not limited to those acquired based on predetermined basis data, a process of generating a feature value of each of a plurality of time points based on a role space arrangement at a corresponding time point will be described in detail.

The operation of detecting a change point for a formation change based on a role space arrangement of FIG. 34 may include an operation of acquiring role assignment information (S3421), an operation of acquiring a space information set (S3423), and an operation of acquiring space arrangement information (S3425), as shown in FIG. 35.

First, a computing device may acquire role assignment information using the plurality of player tracking data sets (S4321). The role assignment information may include a plurality of role assignments for a plurality of time points in the target session, and each of the role assignments may indicate a plurality of role indices assigned to the plurality of players at a first corresponding time point. That is, the role assignment information may include a plurality of role assignments for a plurality of time points, and the role assignment at each time point may include information on which role index is assigned to each of the plurality of players at a corresponding time point. For example, at least a portion of the "role assignment information acquisition" process as described above with reference to FIGS. 19 and 20 in this description may be applied to a procedure of generating role assignment information based on player tracking data sets.

Subsequently, the computing device may acquire a plurality of space information sets associated with a target period for each of a plurality of role indices based on the role assignment information and the player tracking data sets (S4323). The space information set for each of the plurality of roles may include a sequence of role location data over the target period of the corresponding role. For example, at least a portion of the space information set acquisition procedure of the "role assignment information acquisition" process as described above with reference to FIGS. 19 and 20 in this description may be applied to the space information set acquisition procedure.

When the space information sets are secured, the computing device may acquire role space arrangement information including a plurality of role space arrangements for the plurality of time points (S3425). Each role space arrangement may reflect a location relationship between the role indices at a second corresponding time point. That is, for each of the plurality of time points included in the target period, the computing device may acquire role space arrangements that may represent information on which location relationship the plurality of role indices have at each time point. The role space arrangement information may be understood as information including the role space arrangements for the plurality of time points.

An example of the role space arrangement will be described in more detail below.

By acquiring the player tracking data set (S3410), acquiring the role assignment information (S3421), and acquiring the space information sets (S3423), a role assignment for each player can be known for each of a plurality of time points included in the target session, and the locations of the players at each point can be known. Therefore, it is possible to acquire information on the locations of all the roles at each time.

A role space arrangement may be considered as a feature value for each time point for detecting a change point indicating a time point at which a formation changes. In team sports, a formation may be represented as a location relationship between roles, and thus the location relationship between the roles at each time point can be more advantageously utilized as a feature value for a corresponding time point for determining a formation change time point.

For example, if 2, 5, and 3 players are arranged in the front, the center, and the rear, the formation may be determined as a 3-5-2 formation. As described above, when considering the location change of roles in a fluid team sport, a location relationship between the roles may be more suitable for detection of a formation change than the locations of the roles.

As for locations in a stadium, even if the locations of the roles change very dynamically, a relationship between a specific role and other roles adjacent to the role may not change significantly as long as the formation is maintained. Specifically, referring to the center forward in 3-5-2 formation, the distances between the center forward and both wing forwards may change very flexibly. However, by reviewing positions adjacent to the center forward, it can be seen that the wing forwards are the adjacent positions in most cases even if their locations are changing.

Therefore, according to an embodiment of the present disclosure, information on which role is adjacent to each of the plurality of roles may be utilized as inter-role location information. That is, a feature value for each time point may be generated based on a role space arrangement reflecting the location relationship between the roles.

However, according to an embodiment of the present disclosure, inter-role location information may be extracted based on the role-wise adjacency role information, but the technical spirit of the present disclosure is not limited thereto. For example, a feature value based on deep learning may be generated through the locations of 10 positions. Like this, a stadium-based (x, y) coordinate system may be used.

More specifically with respect to the generation of a feature value based on a role space arrangement, a role space arrangement at each time point may include role adjacency information reflecting whether a first role out of the plurality of roles is adjacent to a second role out of the plurality of roles at a corresponding time point. That is, the role adjacency information may be information indicating whether at least one of the plurality of roles is adjacent to another one of the plurality of roles.

More specifically, the role adjacency information may include a role adjacency matrix reflecting whether each of the plurality of roles is adjacent to the others of the plurality of roles. That is, whether all of the plurality of roles are mutually adjacent to each other in a relationship between all other roles may be indicated as a matrix having rows for all the roles and columns for all the roles.

Here, the role adjacency matrix may be acquired by performing Delaunay triangulation on the plurality of roles. That is, Delaunay triangulation may be used to determine which roles are adjacent to which roles.

Figure 38:
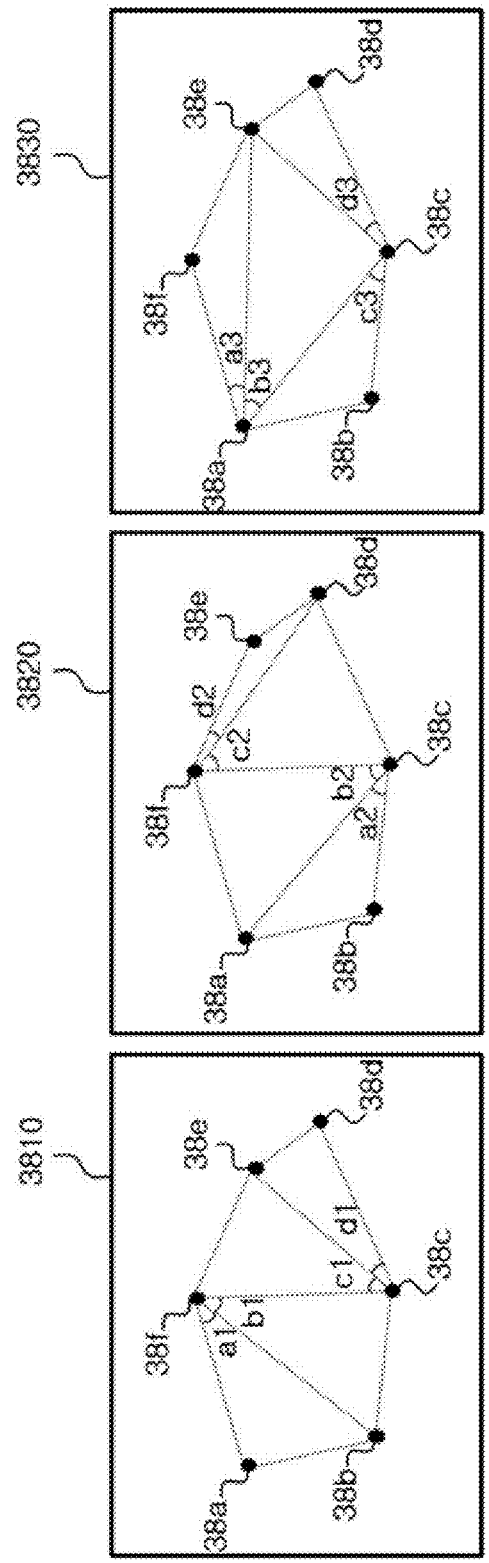
FIG. 38 illustrates a Delaunay triangulation for role adjacency determination.

In this regard, FIG. 38 illustrates the Delaunay triangulation for role adjacency determination. The Delaunay triangulation may be dividing a polygon generated by connecting the positions of the roles into triangles such that the sum of the minimum angles can be largest. For example, as shown in FIG. 38, a hexagonal polygon may be created by connecting the locations 38*a*, 38*b*, 38*c*, 38*d*, 38*e*, and 38*f* of the plurality of roles, and the polygon may be divided into triangles. Comparing a first division form 3810, a second division form 3820, and a third division form 3830, the sum of the minimum angles of the triangles in the first division form 3810 is a1+b1+c1+d1, the sum of the minimum angles of the triangles in the second division form 3820 is a2+b2+b2+d2, and the sum of the minimum angles of the triangles in the third division form 3830 is a3+b3+c3+d3. The sum of the minimum angles of the triangles in the first division form 3810, a1+b1+c1+d1 is largest, and the first division form 3810 may be determined as the division into triangles according to the Delaunay triangulation. Intuitively, the division into triangles as close to an equilateral triangle as possible may be the form of the Delaunay triangulation. According to this, the division may have the smallest acute angle, and due to the characteristic of a triangle in which the angle becomes smaller as the vertices are farther away, it is possible to derive the result of connecting points as close to each other as possible. Accordingly, this can reduce the probability that points that are excessively spaced apart are determined to be adjacent to each other when determining adjacent points of each of the plurality of points.

Specifically, according to the Delaunay triangulation, points sharing a triangle may be determined to be adjacent to each other. For example, the points 38*a*, 38*b*, and 38*f* in the first division form 3810 may be determined as adjacent points, and points having an excessively large distance are not found among the other points determined to be adjacent to each other according to the triangle. However, for example, a triangle including the points 38*a*, 38*c*, and 38*e* is in the third division form 3830. Although the distance between the points 38*a* and 38*c* and the distance between the points 38*a* and 38*b* are relatively large, the points may be determined to be adjacent to each other. Accordingly, the first division form 3810 according to the Delaunay triangulation can be effectively used to determine whether a plurality of points are adjacent to each other without the problem of having an excessively large distance.

In the method according to an embodiment of the present disclosure, Delaunay triangulation may be used in determining whether a plurality of roles are adjacent to each other with respect to a location relationship between the roles. Accordingly, for example, when roles A to J exist, it may be determined whether the plurality of roles are adjacent to each other. For example, role B may be determined to be adjacent to role A, role C, and role D. Like this, adjacent roles may be determined for each individual role.

As described above, according to an embodiment of the present disclosure, a role space arrangement at each time point may include role adjacency information reflecting whether a first role out of the plurality of roles is adjacent to a second role out of the plurality of roles at a corresponding time point. That is, the role adjacency information may be information indicating whether at least one of the plurality of roles is adjacent to another one of the plurality of roles, for example, information including the Delaunay triangulation result.

Meanwhile, FIG. 39 is an example of a role adjacency matrix indicating a location relationship between roles. As described above, more specifically, the role adjacency information according to an embodiment of the present disclosure may include a role adjacency matrix reflecting whether each of the plurality of roles is adjacent to the others of the plurality of roles. That is, whether all of the plurality of roles are mutually adjacent to each other in a relationship between all other roles may be indicated as a matrix having rows for all the roles and columns for all the roles. As exemplarily shown in FIG. 39, a role adjacency matrix including all roles in rows and columns and having different values depending on whether roles corresponding to the rows and columns are adjacent to each other at the intersections of the rows and columns may be acquired. For example, the value may be set to be 1 when the roles are adjacent to each other and 0 when the roles are not adjacent to each other, but the present invention is not limited thereto. Different arbitrary values may be assigned depending on the role adjacency.

A feature value is generated for each of a plurality of time points, and thus the role adjacency matrix as illustrated in FIG. 39 may be generated at each time point.

Meanwhile, although a procedure for generating a feature value for each of a plurality of time points has been described above based on the role space arrangement, the technical spirit of the present disclosure is not limited thereto. For example, a player space arrangement may be used to generate feature values, and a player space arrangement at each time may include player adjacency information reflecting whether a first player out of a plurality of players is adjacent to a second player out of the plurality of players at each time point. Also, the player adjacency information may include a player adjacency matrix reflecting whether the plurality of players are adjacent to each other. For example, in a form similar to that shown in FIG. 39, a player adjacency matrix may be generated in which, for example, whether the first to tenth players are adjacent to each other is indicated by specific values. Similar to the case of role adjacency, a player adjacency matrix may also be acquired by performing Delaunay triangulation on the positions of the players.

Referring back to FIG. 34, when feature values for the time points are calculated in the operation of detecting a change point for a formation change (S3420), the computing device may detect a change point by applying a change point detection algorithm based on the calculated feature values.

Here, according to an embodiment of the present disclosure, the change point detection algorithm may be applied to information on the distances between the time points. More specifically, the operation of detecting a change point for a formation change (S3420) may further include an operation of acquiring information on the distances between feature values for the time points (S3427) and an operation of applying the change point detection algorithm to the information on the distances (S3429).

In this regard, FIG. 36 is a detailed flowchart for the acquisition of distance information for a change point detection process of FIG. 34. Referring to FIG. 36, the computing device may acquire information on the distance between a feature value of a first time point and a feature value of a second time point among the feature values for the plurality of time points (S3427).

Here, the distance between feature values may be a value reflecting the degree of difference between feature values. According to an embodiment of the present disclosure, when the feature value of each time point is a role adjacency matrix, the distance between the feature values may represent, for example, the degree to which a role adjacency matrix for a first time point and a role adjacency matrix for a second time point are different from each other. According to an aspect, the distance value between the role adjacency matrices at the time points may be defined as the Manhattan distance, which is obtained by calculating 0 when the values of the corresponding rows and columns of the two matrices are the same and 1 when the values are different and adding the corresponding values for all rows and columns.

Figure 40:
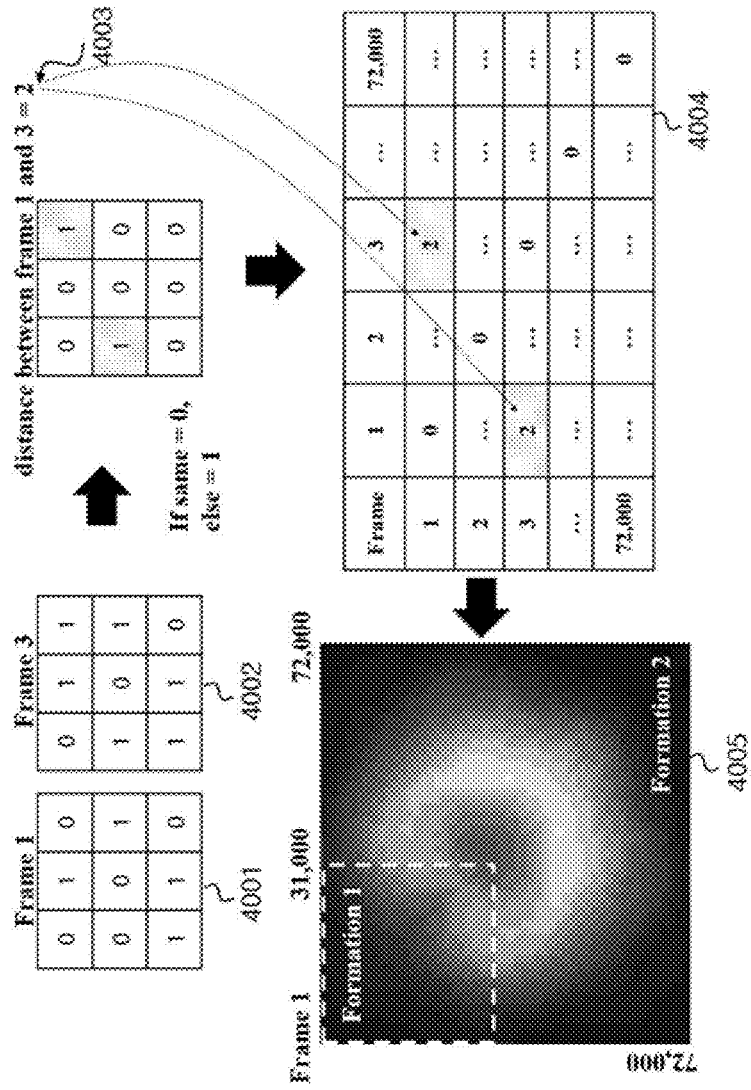
FIG. 40 is an exemplary diagram of a process of performing division into formation time periods based on the distances between multiple frames according to an embodiment of the present disclosure.

In this regard, FIG. 40 is an exemplary diagram of a process of performing division into formation time periods based on the distances between multiple frames according to an embodiment of the present disclosure. By comparing an example (4001) of the role adjacency matrix in frame 1 and the example (4002) of the role adjacency matrix in frame 3 in FIG. 40, calculating 0 when corresponding rows and columns have the same value, calculating 1 when corresponding rows and columns have different values, and then summing the values for all the rows and columns, the result value (4003) may be calculated as 2. That is, in FIG. 40, the Manhattan distance between frame 1 and frame 3 is 2, and according to an aspect of the present disclosure, the distance between the feature value of frame 1 and the feature value of frame 3 may be determined as 2.

The Manhattan distance has been described as an example, but the distance between the matrices is not limited to the Manhattan distance. For example, it should be understood that any type of distance, such as the Hamming distance or the L2 distance, can be used as the distance between the feature values.

Meanwhile, according to an aspect of the present disclosure, information on the distance between the feature values may include an inter-frame distance matrix reflecting the distances from each of the feature values of the plurality of time points to the others of the feature values of the plurality of time points.

For example, the computing device may calculate the distances from each of the plurality of time points included in the target session to the other time points and calculate a matrix including all distance values between the time points based on the calculated distances. That is, the computing device may find the distances between all the frames and generate a matrix based on the distances. Such an inter-frame distance matrix may be used as information on the distances between the feature values.

Referring to FIG. 40, for example, the distance value (4003) between frame 1 and frame 3 may be calculated as 2, and the inter-frame matrix (4004) may have a value of 2 at the first row and third column and at the third row and first column. In this way, by calculating all the distances between all the frames, the inter-frame distance matrix (4004) may be completed.

Referring again to FIG. 36, the computing device may detect a change point by applying the change point detection algorithm to information on the distances between the feature values (S3429). As illustrated in FIG. 40, when the information on the distances between the feature values according to an embodiment of the present disclosure is an inter-frame distance matrix, the change point detection algorithm may be applied to such an inter-frame distance matrix.

As shown in FIG. 40, referring to the example division into formation periods, for example, in a target session with 72,000 frames, as a result of applying the change point detection algorithm, the change point may be determined as a time point of 31,000 frames, and the target session may be divided into a first formation time section from frame 1 to frame 31,000 and a second formation time section from frame 31,001 to frame 72,000.

The inter-frame distance matrix reflecting the distances between the feature values for the plurality of time points has been exemplified as the information on the distances between the feature values above. However, the information on the distances between the feature values according to an embodiment of the present disclosure is not limited thereto.

For example, the information on the distances between the feature values according to an embodiment of the present disclosure may include a sequence of time-series distances reflecting the distance between a feature value for a target time point and a feature value for a time point prior to the target time point, where the time-series distances are calculated for the plurality of time points.

Figure 41:
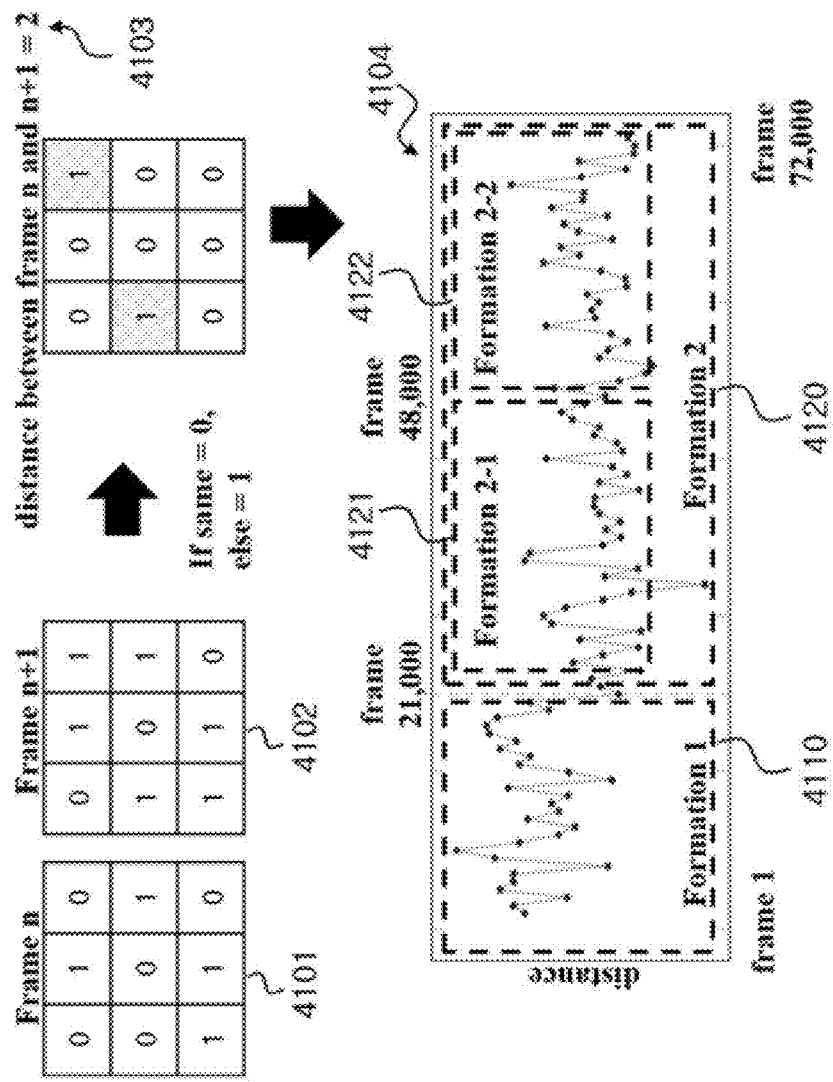
FIG. 41 is an exemplary diagram of a process of performing division into formation time periods based on a sequence of the distances between role adjacency matrices of adjacent frames according to an embodiment of the present disclosure.

In this regard, FIG. 41 is an exemplary diagram of a process of performing division into formation time periods based on a sequence of the distances between role adjacency matrices of adjacent frames according to an embodiment of the present disclosure.

As shown in FIG. 41, a sequence of distance values may be calculated from a sequence of distance values (time-series frames) of a frame-wise matrix. More specifically, the Manhattan distance between the example (4101) of the role adjacency matrix of the $n^{th}$ frame and the example (4102) of the role adjacency matrix of the $(n+1)^{th}$ frame may be calculated as 2, and thus information (4103) on the distance between the feature value for the $n^{th}$ frame and the feature value for the $(n+1)^{th}$ frame may be determined as 2. Like this, the distance between the feature value for the target time point and the feature value for the previous time point prior to the target time point, that is, the distance between feature values for two adjacent time points, may be calculated for each of the plurality of time points included in the target session, and a sequence for the distances between the feature values for the adjacent time points may be acquired. In the present disclosure, a sequence of the distances between feature values for adjacent time points may be referred to as a sequence of time-series distances.

A sequence of time-series distances may be represented as in the graph 4104 of FIG. 41. It can be seen that the distance between the feature values for adjacent time points may vary depending on the time points and the varying distance is displayed through a graph.

According to an aspect of the present disclosure, by applying a change point detection algorithm to the sequence of time-series distances acquired as described above, a change point may be detected for a time point at which a formation changes.

In summary, according to embodiments of the present disclosure, by calculating a location relationship between roles for each frame, calculating the difference (distance) in the location relationship between the frames, and then applying a change point detection technique to information on the calculated distance, a sequence of time points belonging to a target session to be analyzed may be divided into two.

That is, the information on the distance between the feature values is not limited to the above-described examples, and according to an aspect of the present disclosure, the information on the distance between the feature values to which the change point detection algorithm is to be applied may include the distances from a reference feature value for a reference time point to feature values corresponding to the plurality of time points in the target session.

Meanwhile, the division of a target session into formation time periods and the detection of a change point based on the sequence 4104 of time-series distances of FIG. 41 will be described in detail below. First, FIG. 41 shows a sequence of time-series distances in one dimension. By applying a change point detection algorithm to such a sequence of time-series distances, the entire section may be divided into two periods, i.e., a first formation period 4110 and a second formation period 4120. Also, by repeating the same operation, it is possible to subdivide the divided section into two. For example, by applying a change point detection algorithm to feature values of time points included in the second formation period 4120 and performing period division, the second formation period 4120 may be subdivided into a 2-1 formation period 4121 and a 2-2 formation period 4122.

Referring back to FIG. 34, the computing device may determine whether the detected change point is valid (S3430). Specifically, the computing device may determine whether the change point is valid based on the characteristics of a period obtained through division with respect to at least one detected change point. The computing device may check a predetermined division condition for a period obtained through division with respect to the detected change point, confirm the division when the division condition is satisfied, and reject the division when the division condition is not satisfied.

According to an aspect of the present disclosure, the computing device may determine that the detected change point is valid in response to determining that the significance value of scan statics (Scan Statics p) corresponding to the detected change point is less than or equal to a first predetermined threshold value. For example, it may be required that the significance value of scan statics based on division according to the change points be 0.01 or less. Here, the significance may be understood as a value indicating the possibility that values within the division period are incorrectly classified as belonging to the division, and it may be understood that a lower significance value indicates that the division is more proper.

Also, according to an aspect of the present disclosure, the computing device may determine that the change point is valid in response to determining that the time lengths of the first time period and the second time period are both greater than or equal to a second predetermined threshold value. For example, it may be required that the time lengths of the first time period and the second time period, which are division sections, both be greater than or equal to five minutes. Since the possibility that a formation change will be repeatedly performed within an excessively short time is insignificant, division into sections of, for example, five minutes or longer may be determined as valid division.

According to an aspect of the present disclosure, the computing device may determine that the change point is valid in response to determining that the difference between the average of feature values for a plurality of time points included in the first time period and the average of feature values for a plurality of time points included in the second time period is greater than or equal to a third predetermined threshold value. For example, it may be required that the distance between the average location relationship (adjacency matrices) of the two division sections be 7.0 or more. That is, by calculating an evaluation value related to the formations of the two division sections, it may be determined that the formations of both the sections are different from each other only when the evaluation value is greater than a predetermined difference.

Meanwhile, according to an aspect of the present disclosure, the computing device may determine that a valid change point detection or a valid period division is performed only when, as described above, a condition for the significance value of scan statistics, a condition for the minimum time length, and a condition for the difference between feature values of each section are all satisfied.

Referring back to FIG. 34, the computing device may confirm to divide the target session into time sections (S3440) in response to determining that the detected change point is valid. That is, the computing device may divide the target session into at least two time periods based on the change point, and the at least two time periods may include a first time period in which the formation of the team participating in the target session is a first team formation and a second time period in which the formation of the team participating in the target session is a second team formation.

Meanwhile, the division of a period to be analyzed into formation periods may be continuously performed until a division condition (e.g., a condition for satisfying validity of a detected change point) is no longer satisfied. For example, the entire session is divided once, and then the section is not divided when the condition is not satisfied. In this case, it may be determined that the formation is constant throughout the entire session. On the other hand, as described with reference to FIG. 41, by dividing the entire section into two periods, i.e., a first formation period 4110 and a second formation period 4120, applying a change point detection algorithm to the feature values of time points included in the second formation period 4120, and performing period division, the target session may be divided into multiple sections. For example, the second formation period 4120 may be subdivided into a 2-1 formation period 4121 and a 2-2 formation period 4122.

Meanwhile, a device for providing tactical information for team sports according to an aspect of the present disclosure may include a processor and a memory, wherein the processor may be configured to acquire a plurality of player tracking data sets for a plurality of players, wherein each of the player tracking data sets includes a sequence of location data of a corresponding player during a target session; detect a change point reflecting a time point at which the formation of a team participating in the target session changes by applying a change point detection algorithm to feature values for the plurality of time points generated based on the plurality of player tracking data sets; and divide the target session into at least two time periods based on the change point, wherein the at least two time periods include a first time period in which the formation of the team participating in the target session is a first team formation and a second time period in which the formation of the team participating in the target session is a second team formation. A specific operation of the device for providing tactical information for team sports according to an aspect of the present disclosure may follow the above-described formation period division process.

Figure 37:
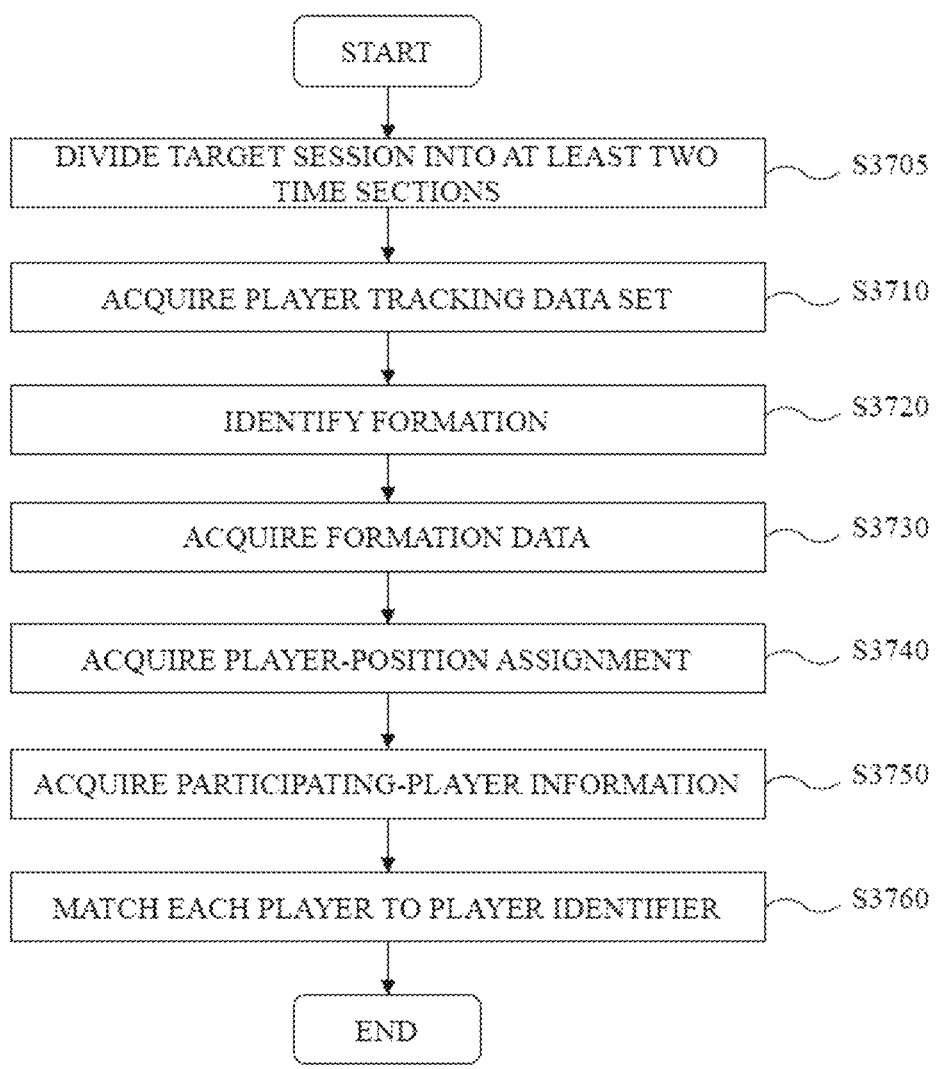
FIG. 37 is a schematic flowchart of a process for formation identification, position identification, and player identifier matching according to an embodiment of the present disclosure.

Matching of formation identification, position identification, and player identifiers FIG. 37 is a schematic flowchart of a process for formation identification, position identification, and player identifier matching according to an embodiment of the present disclosure. The process for formation identification, position identification, and player identifier matching according to an embodiment of the present disclosure will be described in detail below with reference to FIG. 37.

The method and/or processes according to an embodiment of the present disclosure may be performed by a computing device. According to an aspect, the computing device may be an analysis device 1400 as described with reference to FIG. 9, but the present disclosure is not limited thereto. Any device capable of computation with a processor and a memory may be used.

In general, "formation" refers to the tactical arrangement of players participating in a team sport game. According to an embodiment of the present disclosure, by acquiring information on the positions of a plurality of players and/or roles of a team sport game, the formation of a team participating in the corresponding game may be identified based on the information.

As discussed above, in this disclosure, "role" may refer to one of a plurality of participant categories that can match player positions constituting a formation. That is, "role" may be categorized by a role identifier according to the role of a game participant to match one of a plurality of positions before determining which of the plurality of positions it corresponds to, such as "MF" or "CF." According to an embodiment of the present disclosure, which position each role corresponds to may be automatically identified by computer-based technology.

Meanwhile, the term "player" used herein may refer to an entity whose position is tracked by a process of acquiring player tracking data. A sequence of location data for one "role" may be a mixture of at least a portion of player tracking data for two or more "players."

Meanwhile, in the present disclosure, "player" is tracked as an entity participating in a game, but in reality, each player is only classified as a first player or a second player in order to track the location of one distinct entity among a plurality of players and does not directly match a player identifier including actual information such as the player's name or jersey number. In particular, for example, a location information acquisition device that can be worn on a player may be used as a method of tracking the player's location. Strictly speaking, for example, the acquired player tracking data may be tracking information for each location information acquisition device. In the case of using a location tracking device designated for each individual, by obtaining, in advance, data regarding the identification information of each location tracking device and the personal information of a user of a corresponding device, it is possible to identify which piece of player tracking data is data on a player having which piece of personal information. However, in reality, the location tracking devices are difficult to use in a fixed manner for each individual, and in every game, game participants often select and wear any one of the location tracking devices. According to an embodiment of the present disclosure, after determining the role of a player tracking device corresponding to each player tracking data set, identifying a corresponding position, and comparing the identified position to the participating-player information of a corresponding game, it is possible to automatically match a corresponding player identifier to the player tracking data set.

Referring to FIG. 37, the process for formation identification, position identification and player identifier matching according to an embodiment of the present disclosure may include at least one of an operation of dividing a target session into at least two time sections (S3705), an operation of acquiring a player tracking data set (S3710), an operation of identifying a formation (S3720), an operation of acquiring formation data (S3730), an operation of acquiring a player-position assignment (S3740), an operation of acquiring participating-player information (S3750), and an operation of matching each player to a player identifier (S3760). The operations of this example will be described below.

First, as shown in FIG. 37, the computing device may divide a target session into at least two time sections (S3705). The division of the target session may follow, for example, a division process for formation periods as described in the present disclosure, but the present disclosure is not limited thereto. Also, the division of the target session is optional, and the process for formation identification, position identification, and player identifier matching according to an embodiment of the present disclosure may be performed over the entire session, which is not divided.

More specifically, for example, the computing device may divide a target session for one team sport game into at least two time periods. Here, the at least two time periods may include a first time period and a second time period obtained through division based on a formation change of a team participating in the team sport game.

The division into time periods may be performed, for example, by the change point detection process as exemplified in the present disclosure, or may include period division performed according to any division criterion.

Referring back to FIG. 37, the computing device may acquire a player tracking data set (S3710). More specifically, the computing device may acquire a plurality of player tracking data sets for a plurality of players, and each of the player tracking data sets may include a sequence of location data of a corresponding player during a target session. That is, the computing device may acquire, for each of the plurality of players, information on locations at a plurality of time points included in the target session. It should be noted that the process for acquiring player tracking data according to an embodiment of the present disclosure described above with reference to FIG. 18 may be applied, but the present disclosure is not necessarily limited thereto.

Next, the computing device may identify a formation based on the player tracking data set (S3720). Specifically, the computing device may identify the formation of a team participating in a team sport game based on a formation structure for the target session generated based on the plurality of player tracking data sets. In the present disclosure, "formation structure" may refer to information for determining a formation during a target period to be analyzed for a team participating in a team sport game.

Here, when the target session is divided into, for example, a first time period and a second time period according to an aspect of the present disclosure, the operation of identifying a formation (S3720) may include an operation of identifying a first formation of the team for a first time period based on a first formation structure for the first time period and an operation of identifying a second formation of the team for a second time period based on a second formation structure for the second time period.

In other words, according to an aspect of the present disclosure, the target session may be divided into at least two time sections, e.g., a first time period and a second time period, and the formation of the team participating in the team sport may be identified for each of the time periods.

In a team sport game, it is common for a team formation to change more than once even in one game according to tactical instructions or changes in circumstances. Accordingly, by detecting a time point at which the team formation changes, dividing a target session for one team sport game into a plurality of formation periods, and identifying a formation for each period based on data corresponding to each of the periods, it is possible to identify a team formation with greater accuracy and utilize the identification result in a tactical analysis.

"Formation structure," which is information or data for determining a formation during the target period to be analyzed of the team participating in the team sport game, will be described in detail below.

According to an aspect of the present disclosure, the formation structure may be generated based on the locations of players or a location relationship between players. More specifically, the formation structure according to an aspect may be generated based on at least one of sequences of locations of each of the plurality of players during the target session, average locations of each of the plurality of players during the target session, a sequence of player space arrangements for the time points during the target session, and the average of player space arrangements for the time points during the target session. Here, each player space arrangement may reflect a location relationship between the players at each time point.

According to another aspect of the present disclosure, the formation structure may be generated based on the locations of roles or a location relationship between roles. More specifically, the formation structure according to an aspect may be generated based on at least one of sequences of locations of each of the plurality of roles during the target session, average locations of each of the plurality of roles during the target session, a sequence of role space arrangements for the time points during the target session, and the average of role space arrangements for the time points during the target session. Here, the role space arrangement may reflect a location relationship between the roles at each time point.

In other words, the formation identification process according to an embodiment of the present disclosure may include obtaining data related to the locations of players and/or roles during a target period in which the formation is intended to be identified and identifying the formation of the corresponding period based on the data. Also, location-related data that may be acquired in embodiments of the present disclosure includes location data of a plurality of entities for each of the plurality of time points. Therefore, for formation identification, various combinations or variations of the data for the plurality of locations of the plurality of entities at the plurality of time points may be utilized.

Exemplary methodologies for identifying a team formation for a period to be analyzed based on a formation structure will be described below.

First, according to an aspect of the present disclosure, the formation identification may be performed using artificial neural network-based deep learning. In performing the formation identification (S3720), the computing device may determine a formation identifier corresponding to the previously acquired formation structure using an artificial neural network-based formation identification model. Here, the formation identification model may be generated by training an artificial neural network based on the plurality of training data sets, wherein each training data set includes a formation structure sample and a formation identifier used for labeling the formation structure sample.

For example, when a formation structure corresponding to a target period for which a formation is intended to be identified is input to the formation identifier model, the computing device may receive a corresponding formation identifier.

In this regard, FIG. 42 illustrates an example label of training data for artificial neural network-based formation identification according to an embodiment of the present disclosure. As exemplarily shown in FIG. 42, for example, in a soccer game, team formation information 4230 is represented as an arrangement of numbers corresponding to the number of players, such as "3-5-2" or "4-4-2." A formation identifier 4220 may be designated to each piece of formation information. For example, as shown in FIG. 42, formation identifier "1" may be designated to a "3-5-2" formation, and formation identifier "2" may be designated to a "4-4-2" formation. Accordingly, when a formation structure for a target period is input to the formation identification model and formation identifier "1" is received, it can be seen that the team formation of the corresponding target period corresponds to the "3-5-2" formation.

An exemplary training data set for a formation identification model according to an aspect of the present disclosure will be described with reference to FIG. 42. As shown in FIG. 42, the training data set may include a formation structure sample 4210 and a formation identifier 4220 used for labeling the formation structure sample. An input (ANN Input Characteristic) of an artificial neural network-based formation identifier model according to an aspect of the present disclosure may be a formation structure, and an output (ANN Result label) may be a formation identifier of a formation structure. The training data set may be prepared by securing a plurality of sample formation structures, determining which formation each sample formation structure corresponds to, and labeling the formation with a corresponding formation identifier.

In FIG. 42, it is exemplarily shown that a set of representative locations of a plurality of roles for a specific frame is labeled with a formation identifier. According to an aspect, as shown in FIG. 42, a set of representative locations of a plurality of roles for one frame may be used as a formation structure. Here, one frame may be, for example, a representative time point (e.g., either the middle time point, the start time point, or the end time point of the target period) of a target period. Alternatively, a set of average locations of roles at a plurality of time points in the target period may be used as a formation structure for the target period and labeled with one formation identifier. In addition, a sequence of time points including the set of locations of the plurality of roles may be used as a formation structure. For example, all the location values of roles A to J for ten frames may be used as one formation structure and labeled with one formation identifier. The ten frames may be sampled at predetermined intervals during the target period.

In other words, various types of data may be used as a formation structure when a formation determination model is generated by training an artificial neural network using a formation structure as an input and a formation identifier as an output.

For example, when formation identification is performed using deep learning (DL), formation identification may be performed, for example, based on the location distribution of the roles. Noise and the like may be removed within a specific formation period, and for example, sequences of locations of ten roles may be used as an input to the artificial neural network. Alternatively, the average locations of the roles within a formation period, i.e., average locations (x1, y1) to (x10, y10) of roles A to J, may be used as an input of the artificial neural network.

According to another aspect of the present disclosure, formation identification may be performed by using, as an input of the artificial neural network, an adjacency matrix that reflects a location relationship between players or roles.

Also, when the artificial neural network is used for formation identification, a sequence of adjacent matrices or an average adjacency matrix may be used as an input of the artificial neural network. Here, the average adjacency matrix may indicate an average value matrix of the adjacent matrices of all the frames except noisy frames in a formation period subject to the formation identification. It should be noted that the acquisition of the adjacent matrix or the location relationship between roles may be performed according to the above-described embodiments of the present disclosure, but the present disclosure is not limited thereto.

Meanwhile, when data including values for the plurality of roles is used as a formation structure according to an embodiment of the present disclosure, it may be required to sort the values for the roles included in the formation section of each formation period. For example, when a role adjacency matrix is used as a formation structure, rows and/or columns in the role adjacency matrix may be adjusted to correspond to rows and/or columns in other role adjacency matrices. In other words, sorting may involve adjusting the column and rows of other adjacency matrices with respect to a reference adjacency matrix. This may be processed by re-assigning the order of roles using a Hungarian algorithm based on the location distribution.

Figure 43:
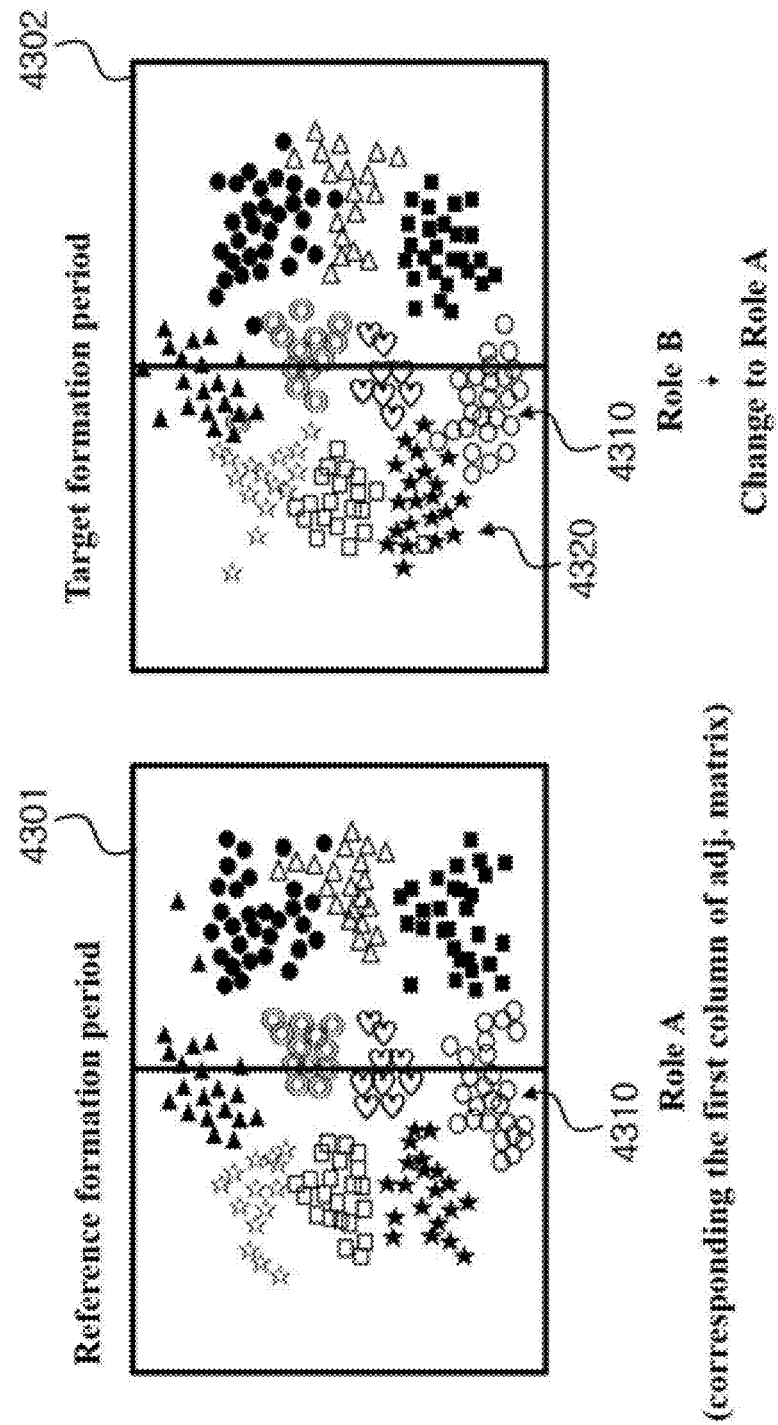
FIG. 43 is a conceptual diagram of a role sorting process for training data generation or clustering between different formation periods.

In this regard, FIG. 43 is a conceptual diagram of a role sorting process for training data generation or clustering between different formation periods.

As described above in the present disclosure, "role" and "position" may not be the same, and a role index for each of a plurality of roles is arbitrarily assigned first. For example, role A in a specific target session and role A in other target sessions may be role indices for different positions. For example, role A in a specific target session or formation period may be designated to a role corresponding to the CF position, and role A in another target session or formation period may be designated to a role corresponding to the DF position.

As illustratively shown in FIG. 43, for example, for a reference formation period 4301, the index of role A may be assigned to a role corresponding to a right midfielder (RMF) position 4310 of a 3-4-3 formation. On the other hand, for a target formation period 4302, the index of role A may be assigned to a role corresponding to a right center back (CB)

position 4320 of a 3-4-3formation, and the index of role B may be assigned to a role corresponding to the right midfielder (RMF) position 4310.

Therefore, a sorting procedure may be required to allow the same role index to be assigned to the same position in a plurality of formation structures, each of which includes information on a plurality of role identifiers. For example, the role identifier of a role corresponding to the right midfielder (RMF) position 4310 of the target formation period 4302 may be changed to role A.

According to an embodiment of the present disclosure, formation structure samples used for training the artificial neural network may each include a plurality of normalization data elements that are sorted by assigning a plurality of data elements included in the formation structure sample to a plurality of reference data elements included in the reference formation structure. More specifically, by assigning role indices A to J which are data elements included in the formation structure sample to role indices A to J which are reference data elements included in the reference formation structure, the role indices included in the formation structure samples may correspond to the same positions.

Here, the Hungarian algorithm as described above may be utilized for the assignment, but the present invention is not limited thereto. For example, a representative location is determined (reference location) for each of a plurality of roles included in the reference formation period 4301, a representative location is determined (target location) for each of a plurality of roles included in the target formation period 4302, and the assignment of the role indices to the roles during the target formation period may be readjusted to minimize the costs of the reference location-target location matching.

Meanwhile, according to another of the present disclosure, the formation identification may be performed using a clustering technique. For example, in performing formation identification (S3720), the computing device may match a formation structure to a first formation structure group that is any one of a plurality of formation structure groups and may acquire a formation identifier corresponding to the first formation structure group.

For example, when a formation identifier corresponding to the first formation structure group is "1" and formation information corresponding to formation identifier "1" is a "3-4-3" formation, the team formation for the target period may be the "3-4-3" formation.

Here, the plurality of formation structure groups may be generated by clustering a plurality of formation structure samples and labeling each cluster with a formation structure identifier.

In this regard, FIG. 4 shows an example of a formation group according to an embodiment of the present disclosure. As exemplarily shown in FIG. 4, a plurality of formation structures corresponding to a plurality of formations may include, for example, a first formation structure group 410, a second formation structure group 420, a third formation structure group 430, a fourth formation structure group 440, a fifth formation structure group 450, and a sixth formation structure group 460. The formation structure groups may be labeled with, for example, formation structure identifiers "1" to "6."

In this regard, according to the embodiments of the present disclosure, various other computer-based techniques such as a clustering algorithm as well as artificial neural networks may be used for the formation identification.

When using a clustering algorithm for formation identification according to an aspect of the present disclosure, average adjacency matrices may be used for multiple formation periods. Specifically, clustering of multiple formation periods may be performed using the distance between the average adjacency matrices for the multiple formation periods. Here, for example, a Manhattan distance indicating the number of different values between the two matrices may be used as the distance between the average adjacency matrices, but the present disclosure is not limited thereto.

Sample formation structures for a plurality of target sessions or sample formation structures for a plurality of formation periods may be secured, and the secured sample formation structures may be clustered into, for example, first to sixth formation structure groups 410 to 460. For example, when the sample formation structure is an average adjacency matrix having an average value of the adjacency matrices in the corresponding period, clustering may be performed based on the distance between the average adjacency matrices for each period. It may be determined which formation each of the results obtained through the clustering, e.g., each of the first to sixth formation structure groups 410 to 460, corresponds to, and then the labeling with the position identifier may be performed.

Subsequently, when it is determined which formation structure group the formation structure of the target period in which the formation is intended to be identified corresponds to, the formation of the target period may be identified based on a formation identifier corresponding to the corresponding formation structure group.

Meanwhile, even in performing clustering, when the formation structure includes role-related values, it may be required to sort the roles. According to an embodiment of the present disclosure, each formation structure sample may include a plurality of normalization data elements that are sorted by assigning a plurality of data elements included in the formation structure sample to a plurality of reference data elements included in the reference formation structure. A procedure described in relation to a training set of an artificial neural network may be utilized as a specific role arrangement procedure.

Referring back to FIG. 37, the computing device may acquire formation data (S3730). Specifically, when a formation for a target session or period is identified by the operation of formation identification (S3720), the computing device may acquire formation data corresponding to the identified formation.

Here, the formation data may include information on a plurality of positions for the formation and location feature values for a plurality of positions. That is, the formation data may include information on which positions are included in a specific formation and information on which location characteristics or position distributions each position has.

For example, formation information on a "3-4-3" formation may include data in which a left wing (LW), a center forward (CF), a right wing (RW), a left midfielder (LMF), a first central midfielder (CMD 1), a second central midfielder (CMD 2), a right midfielder (RMF), a first center back (CB 1), a second center back (CB 2), and a third center back (CB 3) are included as information on a plurality of positions. Also, the formation information on the "3-4-3" formation may include location feature values for the positions as described above.

According to an aspect of the present disclosure, the location characteristic value for each position may be generated based on at least one of a representative location of the corresponding position or the representative location distribution of the corresponding position. That is, the location characteristic value may be understood as a value reflecting what location characteristics each position has.

Referring back to FIG. 37, the computing device may acquire a player-position assignment (S3740). Specifically, the computing device may acquire player-position assignments for a plurality of players. Here, each of the player-position assignments may be generated by assigning the plurality of players to each of a plurality of positions based on location characteristic values for the plurality of players and location characteristic values for the plurality of positions. That is, the computing device may determine which player corresponds to which position among a plurality of players of a team participating in a team sport.

Here, as described above, the location characteristic value for each position may be generated based on at least one of the representative location of the corresponding position or the representative location of the corresponding position. That is, the location characteristic value may be understood as a value reflecting what location characteristics each position has. Also, the location characteristic value for each player may be generated based on at least one of the representative location of the corresponding player or the representative location of the corresponding player. That is, the location characteristic value may be understood as a value reflecting what location characteristics each player has.

In this regard, the information on the player's location may be acquired from the player tracking data sets according to an aspect of the present disclosure, and the information on the position's location may be acquired from the formation data according to an aspect of the present disclosure. Since the information on the locations of the players and positions is obtained, a player-position assignment that determines which player corresponds to which position may be acquired by comparing the information.

Accordingly, according to an embodiment of the present disclosure, when player tracking data sets including a sequence for a player's location data are obtained, by processing the player tracking data sets, the formation of a team participating in a team sport game may be identified, and it may be determined which position each player corresponding to the player tracking data set corresponds to.

Meanwhile, during a team sport game, at least one player substitution may occur. In consideration of the case where a player substitution occurs, the player-position assignment as described above may be acquired based on data of an initial period of the team sports game. For example, the initial period may be the first period when the target session is divided into a plurality of periods. Alternatively, the initial period may be a period having a predetermined time length (e.g., 30 minutes) from the start time point of the team sport game.

Referring back to FIG. 37, the computing device may acquire player participation information (S3750). Specifically, the computing device may acquire player participation information of a team participating in a target session. Here, the player participation information may include a plurality of positions for the formation of the team participating in the target session and player identifiers corresponding to the plurality of positions.

Recently, in most cases with respect to team sport games, information on players participating in each team of each team sport game is submitted in advance. Here, the player participation information may be referred to in various terms, including, for example, a roster, a member list, or a line-up.

The player participation information may include information on what formation the team participating in the target session has. Also, the player participation information may include information on what positions are included in the corresponding formation. Also, the player participation information may include, as a player identifier, information on which player plays which position. That is, information on the name and/or uniform number (jersey number) of a player participating in each position may be included in the player participation information as a player identifier. For example, in the case of a soccer game among team sport games, during the broadcast of the soccer game, the formation of a participating team may be schematically transmitted to a screen before the game starts, positions included in the corresponding formation may be displayed, and a player identifier, such as a jersey number, a name, or a photo, of a player responsible for the position may be displayed. The display information of this relay broadcast may be produced by player identification information submitted in advance before the game.

Subsequently, as shown in FIG. 37, the computing device may match each player to a player identifier (S3760). Specifically, the computing device may match the plurality of players for the target session with a plurality of player identifiers based on player-position assignments. According to an embodiment of the present disclosure, a player tracking data set may be acquired and may be obtained for each of the plurality of players. Also, according to an embodiment of the present disclosure, player-position assignments indicating which position each of the plurality of players corresponding to the player tracking data set corresponds to may be obtained. By using these player-position assignments and information on a plurality of positions and player identifiers included in the player participation information, a plurality of players corresponding to a plurality of player tracking data sets may be matched with the player identifiers.

Accordingly, according to an embodiment of the present disclosure, for example, even if a player locating device such as a sensor device 1200 in FIG. 9 is used not by a specific participant but by any participant without distinction, when a player tracking data set is obtained for each of the plurality of player participants, it is possible to automatically identify which name or jersey number a player indicated by the player tracking data set has.

Meanwhile, a device for providing tactical information for team sports according to an aspect of the present disclosure may include a processor and a memory, wherein the processor may be configured to acquire a plurality of player tracking data sets for a plurality of players, wherein each of the player tracking data sets includes a sequence of location data of a corresponding player during a target session; and identify the formation of a team participating in a team sport game during the target session based on a formation structure for the target session based on the plurality of player tracking data sets, wherein the formation structure reflects information for determining the formation of the team. A specific operation of the device for providing tactical information for team sports according to an aspect of the present disclosure may follow the above-described process for formation identification, position identification, and player identifier matching.

Formation Structure Based on Role Space Arrangement

Figure 33:
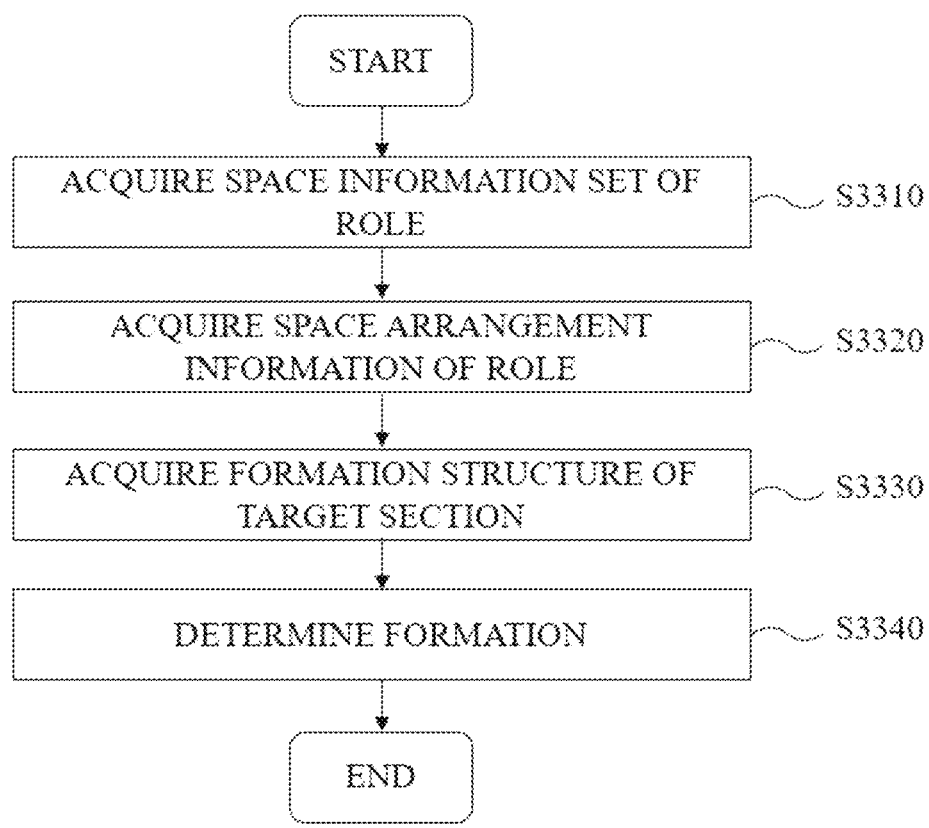
FIG. 33 is a schematic flowchart illustrating a formation structure acquisition process according to an embodiment of the present disclosure.

FIG. 33 is a schematic flowchart for a formation structure acquisition process according to an embodiment of the present disclosure. A process for acquiring a formation structure based on role space arrangement and then determining a formation according to an embodiment of the present disclosure will be described with reference to FIG. 33.

The method and/or processes according to an embodiment of the present disclosure may be performed by a computing device. According to an aspect, the computing device may be an analysis device 1400 as described with reference to FIG. 9, but the present disclosure is not limited thereto. Any device capable of computation with a processor and a memory may be used.

In the present disclosure, as described above with respect to "process for formation identification, position identification, and player identifier matching," "formation structure" may refer to information for determining a formation during a target period to be analyzed for a team participating in a team sport game. The formation identification process according to an embodiment of the present disclosure may include obtaining data related to the locations and/or location relationship of players and/or roles during a target period in which the formation is intended to be identified and identifying the formation of the corresponding period based on the data.

However, in terms of "player" or "role," as described above, "player" and "role" may be different from each other. In particular, when a player substitution in the target session or a position change indicated between players occurs, "role" may be more advantageous for formation identification. Even in terms of "location" and "location relationship," "location relationship" may be more advantageous for formation identification in consideration of a dynamic change in location of a team sport. An example in which "formation structure" is acquired based on a role space arrangement reflecting a location relationship between roles will be discussed below.

As shown in FIG. 33, the computing device may acquire a space information set of a role (S3310). More specifically, the computing device may acquire a plurality of space information sets associated with a target period for each of a plurality of roles based on a plurality of player tracking data sets for a plurality of players.

Here, each of the player tracking data sets may include a sequence of location data of a corresponding player during the target period. It should be noted that the plurality of player tracking data sets may be acquired by the process for acquiring player tracking data according to an embodiment of the present disclosure described above with reference to FIG. 18, but the present disclosure is not necessarily limited thereto.

Also, each of the space information sets may include a sequence of location data of a corresponding role during the target period to be analyzed. The acquisition of the space information sets may be accomplished by the above embodiments of the present disclosure, but the present disclosure is not limited thereto.

Referring back to FIG. 33, the computing device may acquire role space arrangement information (S3320). The role space arrangement information may include a plurality of role space arrangements for a plurality of time points in the target period to be analyzed, and each of the role space arrangements may reflect a location relationship between a plurality of roles at a first corresponding time point. The role space arrangements may be acquired according to the embodiment described above with respect to "formation period division process," but the present disclosure is not limited thereto.

Subsequently, the computing device may acquire a formation structure for a target period to be analyzed based on the plurality of role space arrangements (S3330). Also, the computing device may determine the formation of the team based on the formation structure (S3340).

For example, as described above with respect to "formation period division process" of the present disclosure, the role space arrangements may include role adjacency information reflecting whether a first role out of the plurality of roles is adjacent to a second role out of the plurality of roles at the first corresponding time point. Also, the role adjacency information may include a role adjacency matrix reflecting whether each of the plurality of roles is adjacent to the others of the plurality of roles.

As described above, the role adjacency matrix may be acquired at each of the plurality of time points to be analyzed. As described above with respect to "formation identification process" of the present disclosure, for formation identification using computer-based technology, for example, input data of a training data set for training the artificial neural network may be variously modified in form. Specifically, the formation structure may be a sequence of a plurality of role adjacency matrices for the plurality of time points and may be an average role adjacency matrix reflecting the average of the plurality of role adjacency matrices for the plurality of time points.

Meanwhile, a device for providing tactical information for team sports according to an aspect of the present disclosure may include a processor and a memory, wherein the processor may be configured to acquire a plurality of space information sets associated with a target period for a plurality of roles based on a plurality of player tracking data sets for a plurality of players, wherein each of the player tracking data sets includes a sequence of location data of a corresponding player during the target period, and wherein each of the space information sets includes a sequence of location data of a corresponding role during the target period; acquire role space arrangement information, wherein the role space arrangement information includes a plurality of role space arrangements for a plurality of time points in the target period, and wherein each role space arrangement reflects a location relationship between the plurality of roles at a first corresponding time point; acquire a formation structure for the target period based on the plurality of role space arrangements, wherein the formation structure reflects information for determining the formation of a team participating in a team sport game during the target period; and determine the formation of the team based on the formation structure.

A specific operation of the device for providing tactical information for team sports according to an aspect of the present disclosure may follow the above-described formation structure acquisition process based on role space arrangements.

Division into Role Periods

Figure 44:
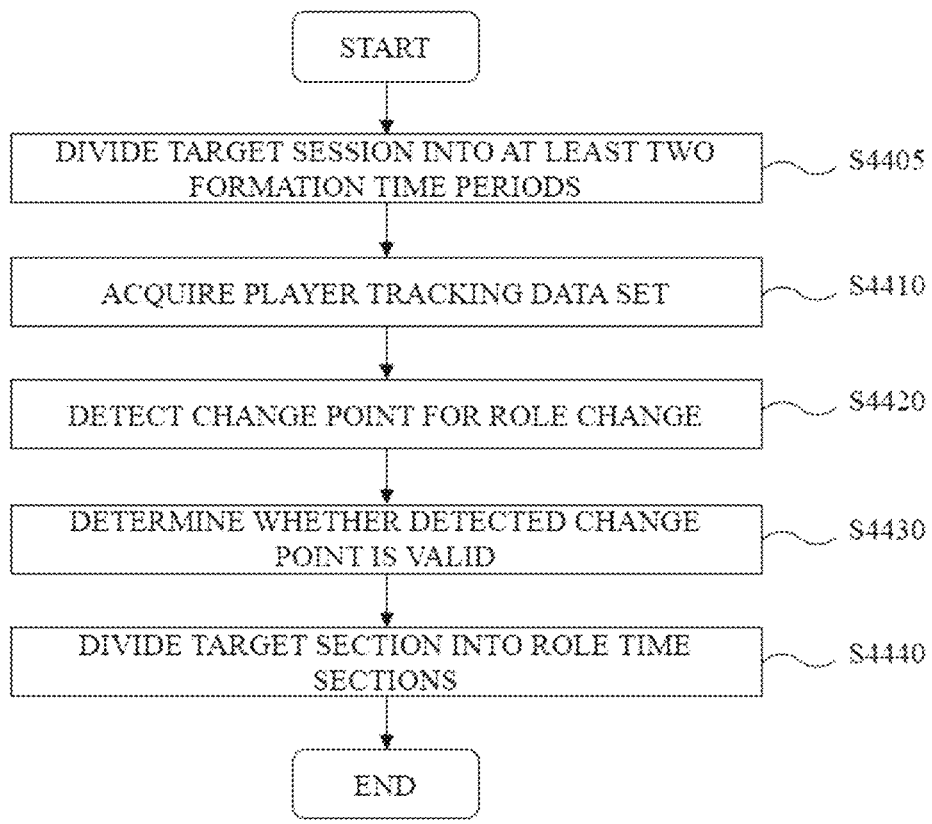
FIG. 44 is a schematic flowchart illustrating a role time period division process according to an embodiment of the present disclosure.
Figure 45:
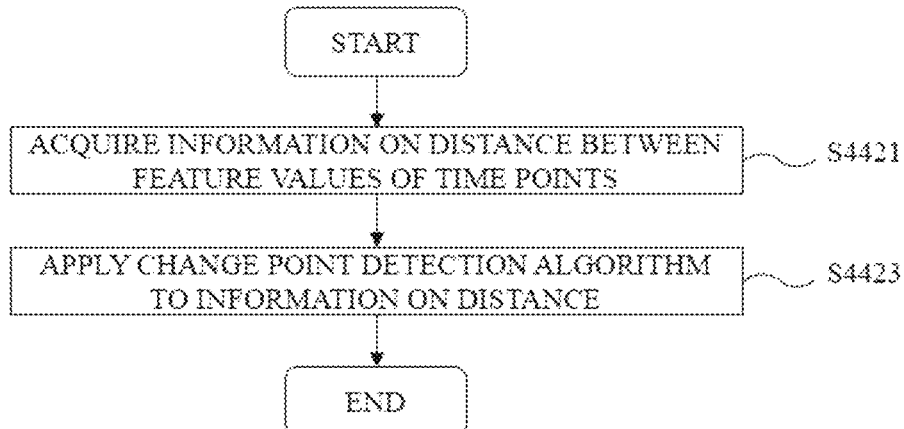
FIG. 45 is a detailed flowchart illustrating the acquisition of distance information for a change point detection process of FIG. 44.

FIG. 44 is a schematic flowchart of a role time period division process according to an embodiment of the present disclosure, and FIG. 45 is a detailed flowchart illustrating distance information acquisition by a change detection process of FIG. 44. The role period division according to an embodiment of the present disclosure will be described in detail below with reference to FIGS. 44 and 45.

The method and/or processes according to an embodiment of the present disclosure may be performed by a computing device. According to an aspect, the computing device may be an analysis device 1400 as described with reference to FIG. 9, but the present disclosure is not limited thereto. Any device capable of computation with a processor and a memory may be used.

According to an embodiment of the present disclosure, for example, the computing device may divide a target session to be analyzed into at least two role time periods with respect to a time point at which the roles of at least some of a plurality of players participating in a team sport game change. In team sports, even when the formation of a team is maintained, players in charge of positions belonging to the formation may switch with each other. For example, while a "3-4-3" formation is maintained, a player in charge of a role "RMF" and a player in charge of a role "CMF 1" may switch with each other according to a tactical instruction so that they play each other's roles. According to an embodiment of the present disclosure, the computing device may detect a time point at which the roles of at least some of the plurality of players change and divide the target period into role time periods with respect to the detected change point.

Meanwhile, here, a role change may be an "instructed role change" due to tactical necessity, etc., and is distinguished from a "temporary role swap" such as wing back overlapping and a corresponding cover play, as described above.

By performing division into role time periods according to the instructed role change, a high-dimensional tactical analysis according to a role assignment in each role time period may be more accurately performed. Also, the determination of a noisy frame according to whether the role assignment is irregular may be more accurately performed.

Referring to FIG. 44, the role period division process according to an embodiment of the present disclosure may include one or more of an operation of acquiring a player tracking data set (S4440), an operation of detecting a change point for a role change (S4420), an operation of determining whether the detected change point is valid (S4430), and an operation of dividing a target period into role time sections (S4440). The operations of this example will be described below.

First, as shown in FIG. 44, the computing device may divide a target session into at least two time sections (S4405). The division of the target session may follow, for example, a division process for formation periods as described in the present disclosure, but the present disclosure is not limited thereto. Also, the division of the target session is optional, and the role period division process according to an embodiment of the present disclosure may be performed over the entire target session, which is not divided.

More specifically, for example, the computing device may divide a target session for one team sport game into at least two formation time periods. Here, the at least two time periods may include a first formation time period and a second formation time period obtained through division based on a formation change of a team participating in the team sport game.

The division into time periods may be performed, for example, by the change point detection process as exemplified in the present disclosure, or may include period division performed according to any division criterion.

When the target session is divided into at least two formation time periods according to an aspect of the present disclosure, the target period, which is subject to a role time period division process according to an embodiment of the present disclosure described below, may be, for example, one of the first formation time period or the second formation time period.

As shown in FIG. 44, first, the computing device may acquire a player tracking data set (S4410). More specifically, the computing device may acquire a plurality of player tracking data sets for a plurality of players, and each of the player tracking data sets may include a sequence of location data of a corresponding player during the target period, which is subject to the role period division. It should be noted that the process for acquiring player tracking data according to an embodiment of the present disclosure described above with reference to FIG. 18 may be applied, but the present disclosure is not necessarily limited thereto.

Next, as shown in FIG. 44, the computing device may detect a change point for a role change (S4420). More specifically, the computing device may generate feature values corresponding to the time points within the target period based on the plurality of player tracking data sets acquired previously and may apply a CPD algorithm to the feature values. As a result, the computing device may detect a change point indicating a time point at which the roles of at least some of the plurality of players participating in the team sport game during the target period change among the plurality of time points in the target period.

The division of the target session into at least two role time periods may be performed by detecting a change point, which is a specific time point at which the roles of at least some of the plurality of players change, from among the plurality of time points included in the target period to be analyzed. Accordingly, in order to detect a change point, it may be required to generate feature values capable of reflecting different features for the plurality of time points included in the target period. When the feature values of the time points are generated, a change point detection based on the feature values may be accomplished by applying a predetermined change point detection algorithm to sequences of the feature values.

Here, for example, as described above in "3. Related Art" of the present disclosure, a non-parametric variable detection technique may be applied as the change point detection algorithm. More specifically, the change point detection algorithm may include a discrete g-segmentation algorithm. However, as also mentioned in "3. Related Art," the change point detection technique of the present disclosure is not limited to such a specific algorithm, and it should be understood that any CPD algorithm capable of detecting a change point of a characteristic based on a sequence of values to be determined may be used.

The role period division process according to an embodiment of the present disclosure may be, for example, a process of dividing each of the formation time periods into at least two role periods.

Figure 47:
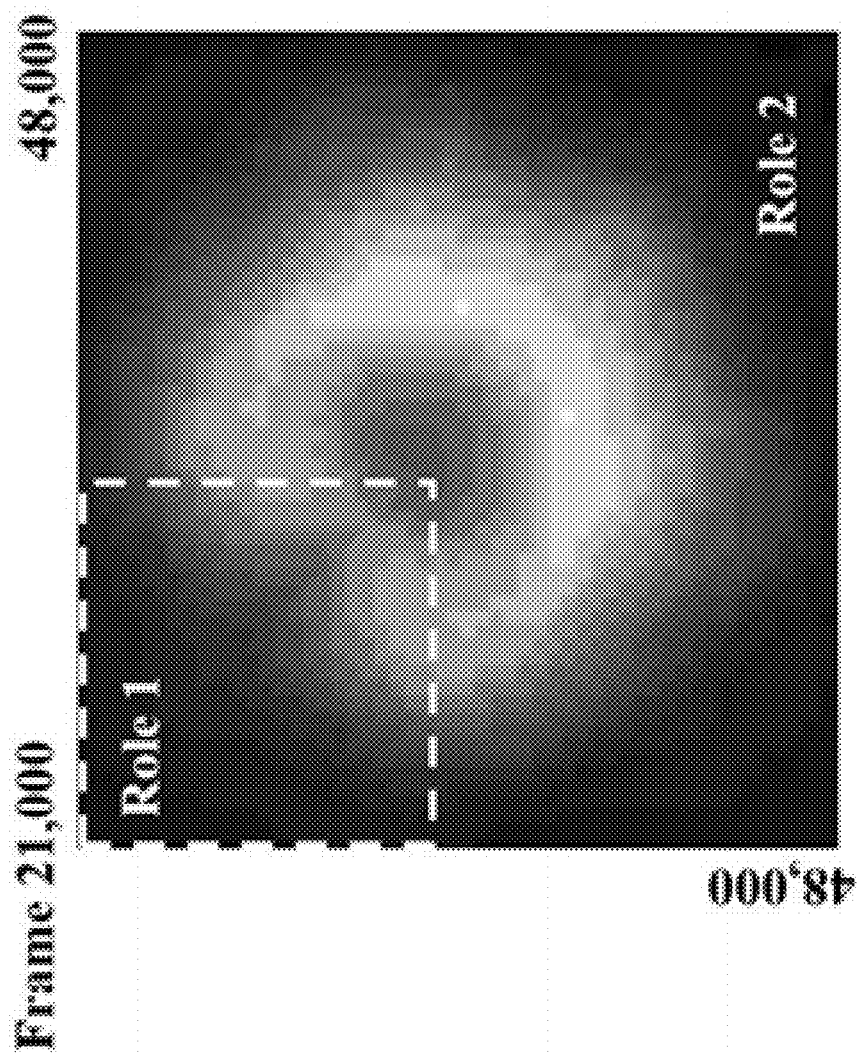
FIG. 47 is an exemplary diagram of role section division using a change point detection algorithm.

In this regard, FIG. 46 is an exemplary diagram showing the acquisition of a sequence of the distances between role assignments at adjacent frames for role period division, and FIG. 47 is an exemplary diagram of role section division using a change point detection algorithm. According to an aspect, the division into the role time periods may be to perform division into role time periods as exemplarily shown in FIG. 47 by calculating a difference value sequence from a sequence of role assignments for a plurality of time points of a single formation period and applying a discrete g-segmentation algorithm to the difference value sequence as exemplarily shown in FIG. 46. As described above in the present disclosure, a change point detection algorithm other than discrete g-segmentation may be applied.

More specifically, a feature value for each of the plurality of time points according to an aspect of the present disclosure may include a role assignment at a corresponding time point. As described in detail above in the present disclosure, a role assignment may indicate a plurality of role indices assigned to the plurality of players at a corresponding time point. That is, a role index may be assigned to each of the plurality of players corresponding to the plurality of player tracking data sets, and the role assignment at a specific time point may include information on which role index is assigned to each of the plurality of players at that time point.

According to an aspect of the present disclosure, when a feature value for each time point includes a role assignment, the operation of detecting a change point for a role change (S4420) may further include an operation of acquiring role assignment information using the plurality of player tracking data sets. The role assignment information may include a plurality of role assignments for the plurality of time points in the target period. It should be noted that although the above role assignment information may be acquired by the role assignment information acquisition process as described above in this description, the present disclosure is not necessarily limited thereto.

Here, the operation of detecting a change point for a role change (S4420) may include detecting a change point based on the distance between the feature values for the plurality of time points. As shown in FIG. 45, the operation of detecting a change point (S4420) may include an operation of acquiring information on the distances between feature values for the time points (S4421) and an operation of applying the change point detection algorithm to the information on the distances (S4423).

More specifically, the computing device may acquire information on the distance between a feature value for a first time point and a feature value for a second time point among the feature values for the plurality of time points (S4421). Here, the distance between the feature values may indicate the degree of difference between the feature values. For example, the distance between the first role assignment and the second role assignment may reflect the difference in the number of roles between the first role assignment and the second role assignment.

According to an aspect, information on the distance between the feature values may include an inter-frame distance matrix reflecting the distances from each of the feature values of the plurality of time points included in the target period to the other feature values of the plurality of time points. Similar to finding an inter-frame distance matrix by calculating the distance between role adjacency matrices at all the frames in the formation section division process according to an embodiment of the present disclosure, the distance between the feature values for the plurality of time points, which is for role period division, may include a matrix including distance information for all the time points.

Alternatively, according to another aspect of the present disclosure, the information on the distance between the feature values may include a sequence of time-series distances reflecting the distance between a feature value for a target time period and a feature value for a time point prior to the target time point. Here, the time-series distances may be calculated for the plurality of time points.

For example, as shown in FIG. 46, a feature value for each of the plurality of time points that may be referenced for division into role time periods according to an embodiment of the present disclosure may be a role at the corresponding time point. FIG. 46 illustrates, for example, a role assignment for dividing a formation time period ranging from 2,100.0 timestamps (frame 21,000) to 4,800.0 timestamps (frame 48,000) into a plurality of role times through formation period division.

According to an aspect of the present disclosure, the information on the distance between the feature values may be a sequence of time-series distances reflecting the distance between the feature value for the target time point and the feature value for a time point prior to the target time point. That is, the sequence of the distances between the feature values for the adjacent time points may be subject to the change point detection algorithm.

As shown in FIG. 46, a role assignment at a time point of 2,100.0 and a role assignment at a time point of 2,100.1 have no difference, and thus the distance (4610) between feature values at the two time points becomes 0. On the other hand, for example, a role assignment at a time point of 3,044.2 and a role assignment at a time point of 3,044.1 have two difference points, and the distance (4610) between feature values for the two time points becomes 2. In this way, the distance between the feature values at each time point and the previous time point may be calculated, and a sequence of time-series distances values for all time points included in the target period may be subject to the change point detection algorithm.

Meanwhile, according to an aspect of the present disclosure, in the operation of detecting a change point for a role change (S4420) of FIG. 44, the computing device may detect a change point based on the remaining role assignments other than at least one irregular role assignment among the plurality of role assignments for the plurality of time points.

According to an aspect, the irregular role assignment may be determined by the computing device determining a dominant role assignment based on the plurality of role assignments and determining at least one irregular role assignment from the plurality of role assignments in consideration of the dominant role assignment. Also, the dominant role assignment may be the most frequent role assignment among the plurality of role assignments. More specifically, when determining the irregular role assignment, the computing device may acquire information on the distances from each of the plurality of role assignments to the dominant role assignment and determine an irregular role assignment based on the information on the distances. The distance between the role assignments may represent the degree of difference between each of the plurality of role assignments and the dominant role assignment.

The determination of the irregular role assignment may be performed using at least a portion of the procedure described above in relation to the role assignment information acquisition process. A feature value of each time point used for role time period division is a role assignment. In this case, when the corresponding time point is an irregular situation in which the formation collapses, it is possible to improve the accuracy of the role time period division by applying the change point detection algorithm except for the role assignment for the corresponding time point.

Subsequently, referring back to FIG. 45, the computing device may detect a change point for a time point at which the roles of at least some of the plurality of players participating in the team sport are changed, by applying the change point detection algorithm to the information on the distances between the feature values (S4423).

Meanwhile, referring back to FIG. 44, the computing device may determine whether the detected change point is valid (S4430). Specifically, the computing device may determine whether the change point is valid based on the characteristics of a period obtained through division with respect to at least one detected change point. The computing device may check a predetermined division condition for a period obtained through division with respect to the detected change point, confirm the division when the division condition is satisfied, and reject the division when the division condition is not satisfied.

According to an aspect of the present disclosure, the computing device may determine that the detected change point is valid in response to determining that the significance value of scan statics (Scan Statics p) corresponding to the detected change point is less than or equal to a first predetermined threshold value. For example, it may be required that the significance value of scan statics based on division according to the change points should be 0.01 or less. Here, the significance may be understood as a value indicating the possibility that values within the division period are incorrectly classified as belonging to the division, and it may be understood that a lower significance value indicates that the division is more proper.

Also, according to an aspect of the present disclosure, the computing device may determine that the change point is valid in response to determining that the time lengths of the first role time period and the second role time period are both greater than or equal to a second predetermined threshold value. For example, it may be required that the time lengths of the first role time period and the second role time period, which are division sections, both be greater than or equal to five minutes. Since the possibility that a role change will be repeatedly performed within an excessively short time is insignificant, for example, division into sections of, for example, five minutes or longer may be determined as valid division.

Meanwhile, according to an aspect of the present disclosure, the computing device may determine that a valid change point detection or a valid period division is performed only when, as described above, a condition for the significance value of scan statistics and a condition for the minimum time length are both satisfied.

Referring back to FIG. 44, the computing device may confirm to divide the target period into role time sections (S4440) in response to determining that the detected change point is valid. That is, the computing device may divide the target period into at least two role time periods based on the change point, and the at least two time periods may include, with respect to a change point at which the roles of at least some of the plurality of players participating in the team sport during the target period change, a first role time period before the change point and a second role time period after the change point.

Meanwhile, a device for providing tactical information for team sports according to an aspect of the present disclosure may include a processor and a memory, wherein the processor may be configured to acquire a plurality of player tracking data sets for a plurality of players, wherein each of the player tracking data sets includes a sequence of location data of a corresponding player during a target period; detect a change point reflecting a time point at which the roles of at least some of the plurality of players change within the target period by applying a change point detection algorithm to feature values for a plurality of time points generated based on the plurality of player tracking data sets; and divide the target period into at least two time periods based on the change point, wherein the at least two time periods include a first role time period before the change point and a second role time period after the change point. A specific operation of the device for providing tactical information for team sports according to an aspect of the present disclosure may follow the above-described role period division process.

Detection of Irregular Situation and Extraction of Highlight Video Data

Figure 48:
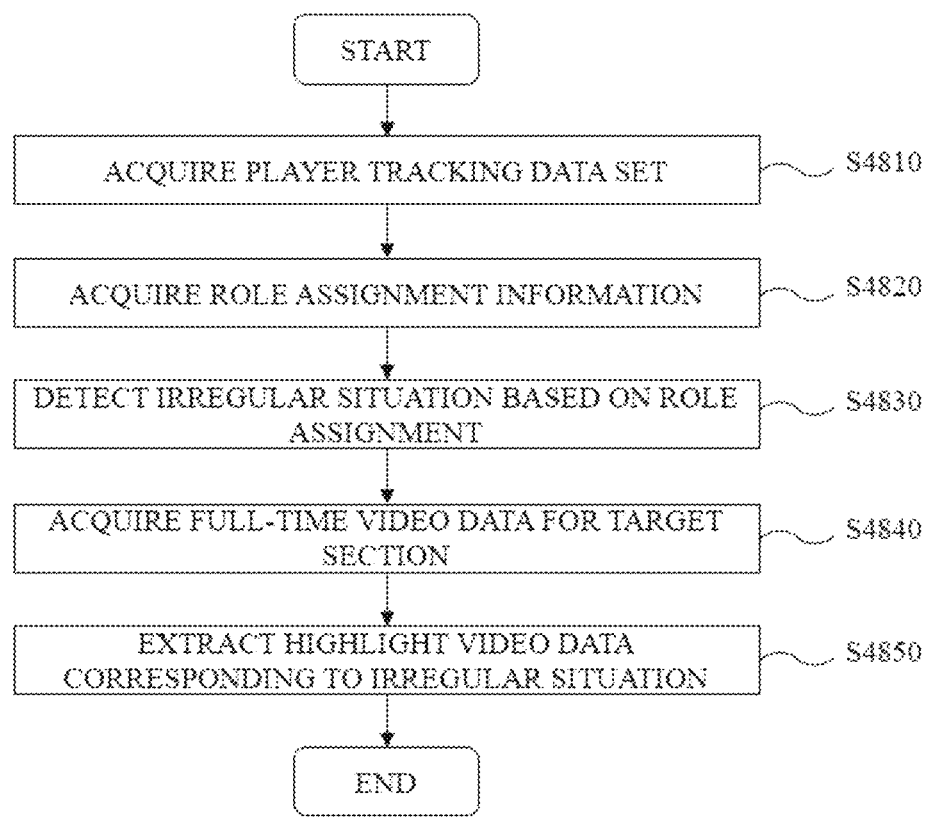
FIG. 48 is a schematic flowchart of a process for irregular-situation detection and highlight video data extraction according to an embodiment of the present disclosure.

FIG. 48 is a schematic flowchart of a process for irregular-situation detection and highlight video data extraction according to an embodiment of the present disclosure, and FIG. 8 is a diagram showing a relationship between a switch ratio and a set-piece occurrence according to an embodiment of the present disclosure. A process for irregular-situation detection and highlight video data extraction according to an embodiment of the present disclosure will be described in detail below with reference to FIGS. 8 and 48.

The method and/or processes according to an embodiment of the present disclosure may be performed by a computing device. According to an aspect, the computing device may be an analysis device 1400 as described with reference to FIG. 9, but the present disclosure is not limited thereto. Any device capable of computation with a processor and a memory may be used.

In the present disclosure, "irregular situation" may refer to a situation in which the positions or formation of a team participating in a time sport game collapses, such as a set-piece situation including, for example, a corner kick or a free kick. For example, in terms of tactical analysis based on role assignments for a plurality of players such as the role assignment information acquisition process or the role period division process according to an embodiment of the present disclosure, data corresponding to an irregular situation may be removed as noise. However, in the tactical analysis of team sport games, the analysis of irregular situations such as set pieces may have an important meaning in itself. The detection of irregular situations in the game may be utilized for statistical analysis of irregular situations such as the occurrence frequency, occurrence time, and duration of irregular situations in the game. Alternatively, a strategy or tactics in an irregular situation, such as a set-piece, of a team participating in a team sport may also be an important analysis target. Also, irregular situations such as set-piece situations are highly likely to correspond to highlights in a game video for a team sport. Thus, when a time point corresponding to an irregular situation is detected, the time point may be utilized as a basis for automatically extracting a highlight video from a full-time game video.

According to an aspect of the present disclosure, the process for irregular-situation detection and highlight video data extraction may include dividing a target session for a team sport game into at least two role time periods and performing irregular-situation detection and highlight video data extraction on one of the role time periods. Also, even when the irregular-situation detection and highlight video data extraction are performed on the entire team sport game, the detection and the extraction may be performed based on a different role location distribution for each role time period. The irregular-situation detection according to an aspect of the present disclosure may be performed based on role assignments, and thus it is possible to improve detection accuracy by applying a different role location distribution for each role time period.

Referring to FIG. 48, the process for irregular-situation detection and highlight video data extraction according to an embodiment of the present disclosure may include at least one of an operation of acquiring a player tracking data set (S4810), an operation of acquiring role assignment information (S4820), an operation of detecting an irregular situation based on a role assignment (S4830), an operation of acquiring full-time video data for a target section (S4840), and an operation of extracting highlight video data corresponding to the irregular situation (S4850). The operations of this example will be described below.

As shown in FIG. 48, the computing device may acquire a player tracking data set (S4810). More specifically, the computing device may acquire a plurality of player tracking data sets relating to a plurality of players, and each of the player tracking data sets may include a sequence of location data of a corresponding player during the target period. That is, the computing device may acquire, for each of the plurality of players, information on locations at a plurality of time points included in the target period. It should be noted that the process for acquiring player tracking data according to an embodiment of the present disclosure described above with reference to FIG. 18 may be applied, but the present disclosure is not necessarily limited thereto.

Next, the computing device may acquire role assignment information (S4820). That is, the computing device may acquire role assignment information using the plurality of player tracking data sets. Here, the role assignment information may include a plurality of role assignments for the plurality of time points in the target period, and each of the role assignments may indicate a plurality of role indices assigned to the plurality of players at a corresponding time point. It should be noted that, although the above role assignment information may be acquired according to at least some of the procedures described above in relation to "role assignment information acquisition process" according to an embodiment of the present disclosure, the present disclosure is not limited thereto.

Referring back to FIG. 48, the computing device may acquire an irregular situation based on the role assignments (S4830). That is, the computing device may detect an irregular situation in the target period based on the plurality of previously acquired role assignments. Here, the difference between a dominant role assignment and a role assignment at a time point corresponding to the irregular situation may be greater than or equal to a predetermined threshold value. In other words, when the role assignments for the plurality of time points are acquired, the computing device may determine a dominant role assignment among the role assignments, compute the degrees of difference between the dominant role assignment and the role assignments corresponding to the time points, and detect, as an irregular situation, a time point at which the difference is greater than or equal to a predetermined threshold value.

In this regard with respect to the detection of irregular situations, FIG. 29 is an example of a role assignment table for determining an irregular role assignment, and FIG. 30 is an example of determining a switch ratio according to the role assignment table of FIG. 29.

More specifically, when the plurality of role assignments for the plurality of time points are acquired through the role assignment information acquisition operation (S4820), the computing device may determine a dominant role assignment based on the plurality of role assignments. According to an aspect, the dominant role assignment may be the most frequent role assignment among the plurality of role assignments. As exemplarily shown in FIG. 29, like that at the first time point 2910, a role assignment in which roles A to J are assigned to the first to tenth players, respectively, occurs with the highest frequency in the entire time section to be analyzed. Thus, the role assignment in which roles A to J are assigned to the first to tenth players, respectively, may be determined as a dominant role assignment. However, the determination of the dominant role assignment is not limited to the most frequent role assignment, and it should be understood that various selection criteria for dominant role assignments are applicable.

Subsequently, the computing device may determine at least one irregular role assignment from the plurality of role assignments in consideration of the dominant role assignment. More specifically, the determination of an irregular role assignment may include operations of acquiring distance information between the dominant role assignment and each role assignment and determining an irregular role assignment based on the distance information.

The computing device may acquire information on the distances from the dominant role assignment to each of the plurality of role assignments. Here, the distance may reflect the degree of difference between the dominant role assignment and each of the plurality of role assignments. Also, according to an aspect, the distance may be a switch ratio from the dominant role assignment with respect to the plurality of role assignments.

More specifically, the computing device may determine the degree of difference between the dominant role assignment and each of the role assignments for the plurality of time points included in the target period. The role assignments of time points included in the second period 2920 of FIG. 29 are role assignments in which the role of the first player and the role of the second player are role B and role A, respectively, unlike the dominant role assignment, and may not be significantly different from the dominant role assignment. On the other hand, it can be seen that the role assignments of time points included in the third period 2930 of FIG. 29 are substantially different from the dominant role assignment.

The degree of difference between the dominant role assignment and each role assignment may be represented as a switch rate calculated based on the number of different roles. Referring to FIG. 30, the roles of the first player and the second player at all the time points included in the second period 2920 are different from those of the dominant role assignment, and the switch ratio may be 20%. On the other hand, referring to the time points included in the third period 2930, it can be seen that the switch ratio is 70% or more because seven or more players have different roles from those of the dominant role assignment.

The computing device may determine an irregular role assignment based on the information on the distances from each role assignment to the dominant role assignment (S1953). For example, when the switch ratio is 70% or more, a corresponding frame may be regarded as an irregular situation. Referring to the example of FIG. 30, the role assignments corresponding to the time points included in the second period 2920 have a switch ratio of 20% and thus are not included in the irregular situation. However, the role assignments corresponding to the time points included in the third period 2930 all have a switch ratio of 70% or more. Thus, the corresponding role assignments may be regarded as irregular situations.

As exemplarily shown in FIG. 8, the detected irregular situation may include an irregular situation regarding an attack situation of a first team participating in a team sport game (indicated by boxes with a white background) and an irregular situation regarding an attack situation of a second team (indicated by boxes with a black background).

Also, for example, a corner kick situation may be denoted by the letter "C," and a free kick situation may be denoted by the letter "F." Specifically, the detected irregular situation may include at least one of the free kick situations 811, 812, 813, and 814 of the first team, the corner kick situations 821, 822, 823, 824, and 825 of the first team, the free kick situation 851 of the second team, or the corner kick situations 861 and 862 of the second team.

Irregular-situation classification information such as information on which team each of the irregular situations detected according to an embodiment of the present disclosure relates to or whether each irregular situation relates to a corner kick or a free kick may be determined according to various criteria. For example, the computing device may be configured to track the location of a ball in a team sport game and may determine the corner kick situation of the first team when the ball is located near the corner of the attack location of the first team in an irregular situation.

Referring back to FIG. 48, the computing device may acquire full-time video data for the target period (S4840) and extract highlight video data corresponding to the irregular situation (S4850). That is, the computing device may acquire full-time video data for the target period and extract highlight video data including video data for the time point corresponding to the irregular situation from the full-time video data.

For example, a set-piece situation such as a corner kick or a free kick may be detected as an irregular situation and may correspond to a highlight, which is the main time point in the whole game. Accordingly, when an irregular situation is detected and information on time points corresponding to the irregular situation is obtained, it is possible to find a time point corresponding to a highlight in the game video over the entire target session of the team sport game. Therefore, it is possible to more easily extract a part corresponding to the highlight video from the entire game video. According to an aspect, the extraction of a highlight video may be performed by the computing device automatically without an editor's manual operation. Also, according to another aspect, a highlight video time point may be displayed, as a bookmark, on a time bar displayed together with the entire game video. For example, as shown in FIG. 8, information on which set piece situation is of a specific team may be displayed together on the time bar, and a viewer who watches the game video may conveniently select and watch a video part for a specific set-piece situation of a specific team by selecting the corresponding bookmark.

Meanwhile, a device for providing tactical information for team sports according to an aspect of the present disclosure may include a processor and a memory, wherein the processor may be configured to acquire a plurality of player tracking data sets for a plurality of players, wherein each of the player tracking data sets includes a sequence of location data of a corresponding player during a target period; acquire role assignment information using the plurality of player tracking data sets, wherein the role assignment information includes a plurality of role assignments for a plurality of time points in the target period and each of the role assignments indicates a plurality of role indices assigned to the plurality of players at a corresponding time point; and detect an irregular situation in the target period based on the plurality of role assignments, wherein the difference between a dominant role assignment and a role assignment of a time point corresponding to the irregular situation is greater than or equal to a predetermined threshold value. A specific operation of the device for providing tactical information for team sports according to an aspect of the present disclosure may follow the above-described process for irregular-situation detection and highlight video data extraction.

Analysis of Playstyle and Extraction of Highlight Video Data

Figure 49:
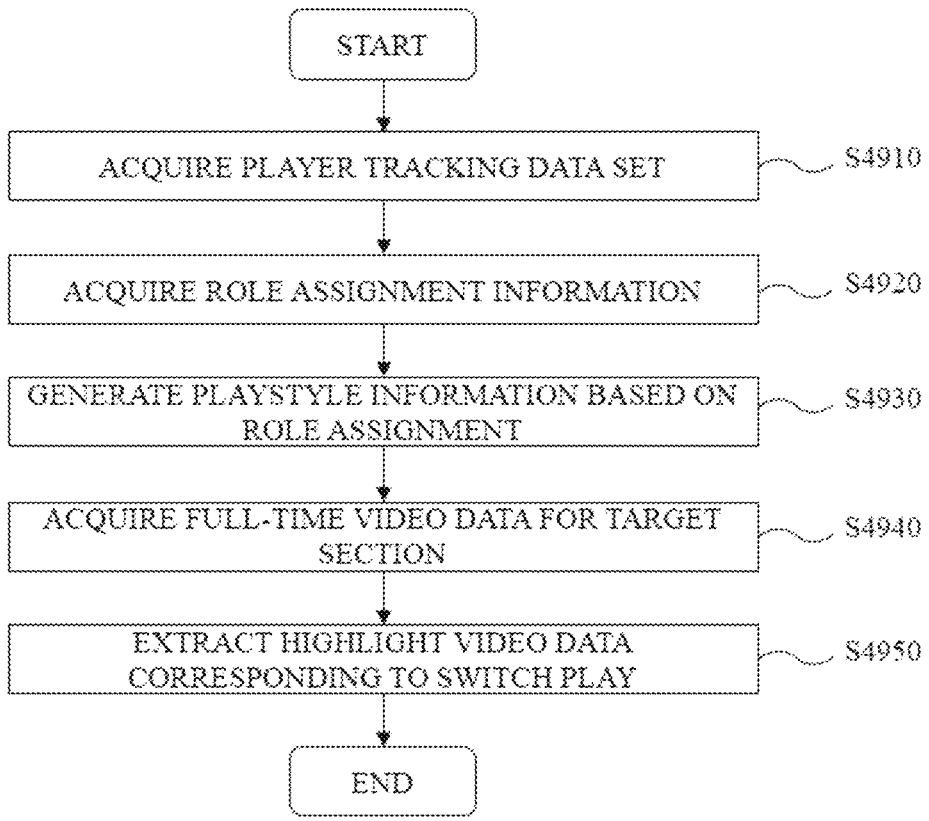
FIG. 49 is a schematic flowchart of a process for playstyle analysis and highlight video data extraction according to an embodiment of the present disclosure.
Figure 50:
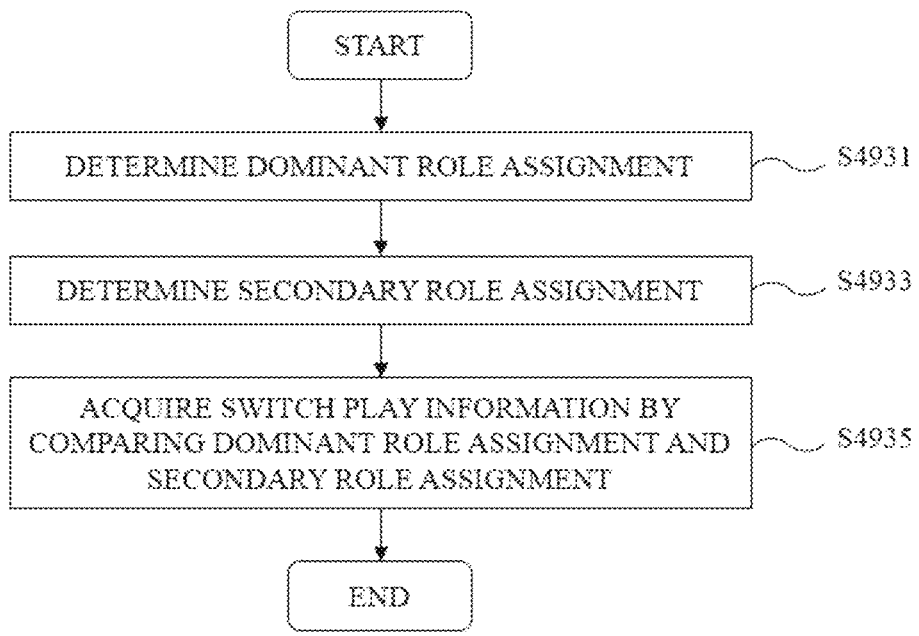
FIG. 50 is a detailed flowchart illustrating a playstyle information generation process of FIG. 49.

FIG. 49 is a schematic flowchart of a process for playstyle analysis and highlight video data extraction according to an embodiment of the present disclosure, and FIG. 50 is a detailed flowchart of a playstyle information generation process of FIG. 49. A process for playstyle analysis and highlight video data extraction according to an embodiment of the present disclosure will be described in detail below with reference to FIGS. 49 and 50.

The method and/or processes according to an embodiment of the present disclosure may be performed by a computing device. According to an aspect, the computing device may be an analysis device 1400 as described with reference to FIG. 9, but the present disclosure is not limited thereto. Any device capable of computation with a processor and a memory may be used.

In the present disclosure, "playstyle" may be understood as indicating tendency or key strategies or tactics for the team sport play of players or a team participating in the team sport game. For example, a playstyle for a team sport may include information on a mainly used team formation and may also include information on the type or frequency of a used partial tactic. The information on the partial tactic may be, for example, utilization tendency of a switch play in which players temporarily swap roles while a consistent formation and roles are maintained, such as overlapping. The analysis of such a playstyle may occupy a very important part in performing a tactical analysis on the opposing team of the team sport. By extracting the key tactics or strategies of the opposing team, counter tactics or strategies to prepare for such tactics or strategies may be established in advance, and players may become familiar with the tactics or strategies through actual training. Meanwhile, for example, the time point of using partial tactics such as a switch play is highly likely to be a highlight in the game video for the team sport. Thus, when the time point of using partial tactics such as a switch play is detected, the detected time point may be used as a basis for automatically extracting a highlight video from a full-time game video.

According to an aspect of the present disclosure, the process for playstyle analysis and highlight video data extraction may include dividing a target session for a team sport game into at least two role time periods and performing playstyle analysis and highlight video data extraction on one of the role time periods. Also, even when the playstyle analysis and highlight video data extraction are performed on the entire team sport game, the analysis and the extraction may be performed based on a different role location distribution for each role time period. The playstyle analysis according to an aspect of the present disclosure may be performed based on role assignments, and thus it is possible to improve analysis accuracy by applying a different role location distribution for each role time period.

Referring to FIG. 49, the process for playstyle analysis and highlight video data extraction according to an embodiment of the present disclosure may include at least one of an operation of acquiring a player tracking data set (S4910), an operation of acquiring role assignment information (S4920), an operation of generating playstyle information based on role assignments (S4930), an operation of acquiring full-time video data for a target section (S4940), and an operation of extracting highlight video data corresponding to a switch play (S4950). The operations of this example will be described below.

As shown in FIG. 49, the computing device may acquire a player tracking data set (S4910). More specifically, the computing device may acquire a plurality of player tracking data sets relating to a plurality of players, and each of the player tracking data sets may include a sequence of location data of a corresponding player during the target period. That is, the computing device may acquire, for each of the plurality of players, information on locations at a plurality of time points included in the target period. It should be noted that the process for acquiring player tracking data according to an embodiment of the present disclosure described above with reference to FIG. 18 may be applied, but the present disclosure is not necessarily limited thereto.

Next, the computing device may acquire role assignment information (S4920). That is, the computing device may acquire role assignment information using the plurality of player tracking data sets. Here, the role assignment information may include a plurality of role assignments for the plurality of time points in the target period, and each of the role assignments may indicate a plurality of role indices assigned to the plurality of players at a corresponding time point. It should be noted that, although the above role assignment information may be acquired according to at least some of the procedures described above in relation to "role assignment information acquisition process" according to an embodiment of the present disclosure, the present disclosure is not limited thereto.

Referring back to FIG. 49, the computing device may generate playstyle information based on role assignments (S4930). That is, the computing device may generate information on a playstyle of at least one team or at least one player participating in a team sport game based on the plurality of role assignments.

According to an aspect of the present disclosure, the information on the playstyle may include at least one of information on the time length of a switch play reflecting a temporary role swap between at least some of the plurality of players, information on the number of switch plays, or information on roles in which a switch play has occurred.

As described above, the playstyle according to an embodiment of the present disclosure may include information on partial tactics of the team or player participating in the team sport. For example, information on the playstyle may include analysis information on a switch play indicating a temporary role swap, such as wing backs overlapping and a winger's cover play, rather than an instructed role change. A multi-dimensional analysis, such as how often the switch play has occurred during a target period, how long the switch play is maintained, or what roles of players the switch has occurred between, may be performed on the switch play.

Referring to FIG. 50, more specifically, the operation of generating information on the playstyle (S4930) may include an operation of determining a dominant role assignment (S4931), an operation of determining a secondary role assignment (S4933), and an operation of acquiring switch play information by comparing the dominant role assignment and the secondary role assignment (S4935).

That is, first, the computing device may determine a dominant role assignment based on the plurality of previously acquired role assignments (S4931). Here, the dominant role assignment may be the most frequent role assignment among the plurality of role assignments. Subsequently, the computing device may determine a secondary role assignment based on the plurality of role assignments (S4933). Here, the secondary role assignment may be the second most frequent role assignment among the plurality of role assignments. When the dominant role assignment and the secondary role assignment are determined, the computing device may acquire information on the switch play by comparing the dominant role assignment and the secondary role assignment (S4935).

In this regard, referring to the role assignment table of FIG. 29 by way of example, like that at the first time point 2910, a role assignment in which roles A to J are assigned to the first to tenth players, respectively, occurs with the highest frequency in the entire time section to be analyzed. Thus, the role assignment in which roles A to J are assigned to the first to tenth players, respectively, may be determined as a dominant role assignment.

Subsequently, as a secondary role assignment, the role assignments may be sorted according to the frequency of the role assignments, such as the second most frequent role assignment or the third most frequent role assignment among the plurality of role assignments. However, the determination of the dominant role assignment or the secondary role assignment is not limited by the frequency of role assignment, and it should be understood that various selection criteria for dominant role assignments and secondary role assignments are applicable.

Figure 51:
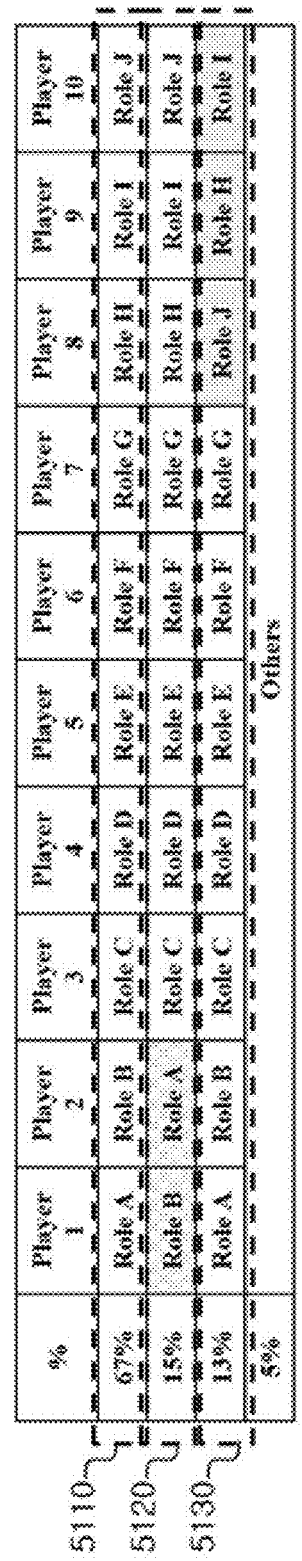
FIG. 51 is an example of the analysis of the frequency of role assignment to generate playstyle information.

In this regard, FIG. 51 is an example of the analysis of the frequency of role assignment to generate playstyle information. As shown in FIG. 51, the role assignments in which roles A to J are assigned to the first to tenth players, respectively, may occupy 67% of all the role assignments and thus may be determined as dominant role assignments 5110. Subsequently, role assignments in which a role swap between the first player and the second player takes place in the dominant role assignment may occupy 15% and thus may be determined as the second most frequent role assignment 5120, and role assignments in which a temporary role swap among the eighth player, the ninth player, and the tenth player takes place in the dominant role assignment may occupy 13% and thus may be determined as the third most frequent role assignment 5130.

When the analysis of the frequency of the role assignments is completed, it is possible to analyze the fact that a switch play between a player in charge of role A and a player in charge of role B has occurred during a period of time corresponding to 15% of the entire target period, by referring to the second most frequent role assignment 5120. Also, for example, role assignment at continuous time points among the second most frequent role assignments may be grouped, and one group may be counted as one occurrence of the switch play. Thus, it is possible to analyze how many times the switch play between the player in charge of role A and the player in charge of role B has occurred during the target period. As described above, the multi-dimensional analysis of various switch plays between players may be performed.

In this regard, FIG. 6 is a graph relating to a formation-period-wise role permutation according to an embodiment of the present disclosure, and FIG. 7 is a diagram showing an example of a tactical analysis using a role permutation according to an embodiment of the present disclosure.

In FIG. 6, for example, role assignments at time points of occurrence of a switch are sorted for each role section such as a first role section 610, a second role section 620, a third role section 630, and fourth and fifth role sections 640, and periods corresponding to the role assignments are displayed in seconds. For example, roles in the first role section 610 may be represented by numbers 1 to 10 as shown in FIG. 7. In this case, it can be seen that the period of a switch play between a player in charge of role #4 and a player in charge of role #6 was longest, i.e., 60 seconds, and a switch play between role #3 and role #5, a switch play among role #6, role #8, and role #9, a switch play between role #1 and role #10, and a switch play between role #5 and role #6 occurred sequentially. As described above, it is possible to analyze how long a switch play between which players is maintained in a specific role section.

The analysis of an exemplary playstyle is reviewed with reference to FIGS. 6 and 7.

For example, the sum of times corresponding to role assignments for the top three switch plays with high frequency in the first role period 610 corresponds to 140 seconds out of the entire role period, 18 minutes, while the sum of times corresponding to role assignments for the top three switch plays with high frequency in the third role period 630 corresponds to 35 seconds out of the entire role period, 13 minutes. Accordingly, it is possible to analyze that the players actively switch roles in the first role period 610 but hardly perform switch plays in the third role period 630.

Meanwhile, the switch play between role #3 and role #5 occurs frequently in the first role period 610 and is a "flase-9play" in which a center forward moves behind a midfielder to provide space for fellow players, as shown in a first exemplary switch play 710 of FIG. 7. However, it is possible to analyze that the corresponding player reduced the above-mentioned switch play as the team formation changed to 4-3-3 in the second role period 620. In this way, by considering a role period and/or a formation period together and considering at least one of information on identified formations, information on identified roles, or information on identified switch plays, a high-dimensional tactical analysis may be performed on a team sport.

Also, it can be seen that, in the first role period unlike other role periods, the fullbacks R1 and R8 have played an offensive role along the sides and have actively performed an overlap play with the wingers R10 and R9. As shown in FIG. 6, it can be seen that the switch play of (6 8 9) and the switch play of (1 10) are ranked high in the first role period 610. Such a switch play is schematically represented in the second exemplary switch play 720 of FIG. 7. However, it is revealed that overlaps are different on both sides. On the left side, R6 covers the location of R8, resulting in a three-person cycle of (6 8 9). On the right side, R4 does not cover the location of R1, resulting in a two-person cycle of (1 10).

Meanwhile, as represented in the second exemplary switch play 720 of FIG. 7, two or more switches are included at one time point. In consideration of this situation, according to an aspect of the present disclosure, the switch play may include a first switch play reflecting a role swap between roles corresponding to a first role group and a second switch play reflecting a role swap between roles corresponding to a second role group. At least one of the plurality of time points may be reflected in both of the first switch play and the second switch play. That is, for example, when the first switch play is a switch play of (6 8 9) and the second switch play is a switch play of (1 10), the first switch play and the second switch play may both be included at one time point such as the time point of the second exemplary switch play 720. In analyzing the frequency of role assignments associated with a switch play according to an aspect of the present disclosure, the role assignment at a time point corresponding to the second exemplary switch play 720 may be included both in counting the occurrences of the first switch play and in counting the occurrences of the second switch play.

Meanwhile, referring back to FIG. 6, in the second role period 620, it may be reviewed that the switch play of (6 9) has occurred multiple times. As shown through the third exemplary switch play 730 of FIG. 7, it may be analyzed that the left winger R9 continuously attempted a cut-in play toward the penalty box through the switch of (6 9).

Also, in the fourth role period 640, it may be analyzed that the team's formation is constantly maintained after the center forward R5 is added, except for general switches (e.g., a switch in the same positions) such as the switch of (3 5) between center forwards or the switch of (4 6) between central midfielders.

Referring back to FIG. 49, the computing device may acquire full-time video data for the target period (S4940) and extract highlight video data corresponding to the switch play (S4950). That is, the computing device may acquire full-time video data for the target period and extract highlight video data including video data for a time point corresponding to the switch play from the full-time video data.

For example, a switch play situation in which at least some of a plurality of players participating in a team sport temporarily swap roles with each other, such as overlapping, may correspond to a highlight, which is a key time point in the entire game. Accordingly, when a switch play situation is detected and information on time points corresponding to the switch play is obtained, it is possible to find a time point corresponding to a highlight in the game video over the entire target session of the team sport game. Therefore, it is possible to more easily extract a part corresponding to the highlight video from the entire game video. According to an aspect, the extraction of a highlight video may be performed by the computing device automatically without an editor's manual operation. Also, according to another aspect, a highlight video time point may be displayed, as a bookmark, on a time bar displayed together with the entire game video. For example, similar to how a bookmark for an irregular situation is displayed on the time bar, which is shown in FIG. 8, the switch play situation may also be displayed as a bookmark (e.g., indicated by the letter "S") on the time bar. A viewer who watches the game video may conveniently select and watch a video part for a switch play situation of a specific team by selecting the corresponding bookmark.

A device for providing tactical information for team sports according to an aspect of the present disclosure may include a processor and a memory, wherein the processor may be configured to acquire a plurality of player tracking data sets for a plurality of players, wherein each of the player tracking data sets includes a sequence of location data of a corresponding player during a target period; acquire role assignment information using the plurality of player tracking data sets, wherein the role assignment information includes a plurality of role assignments for a plurality of time points in the target period and each of the role assignments indicates a plurality of role indices assigned to the plurality of players at a corresponding time point; and generate information on a playstyle of at least one team or at least one player participating in a team sport game based on the plurality of role assignments. A specific operation of the device for providing tactical information for team sports according to an aspect of the present disclosure may follow the above-described process for playstyle analysis and highlight video data extraction.

According to an embodiment of the present disclosure, it is possible to perform tactical analysis for team sports using player tracking data.

According to an embodiment of the present disclosure, it is possible to acquire space information including a sequence of location data of a plurality of roles of a team sport using player tracking data.

According to an embodiment of the present disclosure, it is possible to divide a target session for a team sport game into a plurality of formation periods with respect to a time point at which the formation of a team participating in a team sport changes.

According to an embodiment of the present disclosure, it is possible to detect a change point of a team formation from the player tracking data, search for a time point at which the team formation changes during a game, and identify a team formation for each period.

According to an embodiment of the present disclosure, it is possible to identify the formation of a team participating in a team sport or roles constituting the formation of the corresponding team.

According to an embodiment of the present disclosure, it is possible to automatically match a location information acquisition device that is randomly assigned to a player participating in a team sport with a player identifier.

According to an embodiment of the present disclosure, it is possible to divide a target period into a plurality of role periods with respect to a time point at which the instructed roles of at least some of a plurality of players of a team participating in a team sport change.

According to an embodiment of the present disclosure, it is possible to find a change in player position using player tracking data and extract a team playstyle.

According to an embodiment of the present disclosure, it is possible to find a role switch using player tracking data and extract a set-piece situation.

According to an embodiment of the present disclosure, it is possible to detect an irregular situation using assignment information for a plurality of roles generated from player tracking data.

According to an embodiment of the present disclosure, it is possible to determine information on the playstyle of a team or player participating in a team sport using assignment information for a plurality of roles generated from player tracking data.

According to an embodiment of the present disclosure, it is possible to automatically extract a highlight video from a game video of a team sport using information on an irregular situation or a switch play.

The objects, solutions, and effects of the invention are not limited to those described above, and other content not described herein should be clearly understood by those skilled in the art from the following description and the accompanying drawings.

Since the embodiments disclosed in the present disclosure are merely illustrative of the technical spirit of the present invention, the scope of the technical spirit of the present invention is not limited to these embodiments. Accordingly, it will be understood by those skilled in the art that not only the individual implementations and combinations of the embodiments of the present disclosure described above but also various modifications and variations that can be made without departing from the essential features of the present invention fall within the technical spirit of the present invention. Therefore, the protective scope of the present invention should be construed by the appended claims, and all technical spirits within their equivalents should be construed as being included in the scope of the present invention.

What is claimed is:

1. A method of providing tactical information for team sports, the method comprising operations of:
    acquiring a plurality of player tracking data sets for a plurality of players, wherein each of the player tracking data sets includes a sequence of location data of a corresponding player during a target period;
    acquiring first role assignment information using the plurality of player tracking data sets, wherein the first role assignment information includes a plurality of role assignments for a plurality of time points within the target period, and each of the role assignments is data set which includes a plurality of role indices assigned to the plurality of players at a corresponding time point such that the each of role assignment reflects specific roles of each player of the plurality of players in the same team at the corresponding time point;
    determining a dominant role assignment based on the plurality of role assignments, and wherein the dominant role assignment is related to at least one predetermined team-formation performable by the team;
    determining at least one irregular role assignment from the plurality of role assignments in consideration of the dominant role assignment, and wherein the irregular role assignment is related to roles of the plurality of players that occur during the target period and do not correspond to the predetermined team-formation;
    acquiring a plurality of space information sets associated with the target period for each of the plurality of role indices based on second role assignment information and some of the player tracking data sets corresponding to the second role assignment information, and wherein the second role assignment information is that which excludes at least one of the irregular role assignment from the first role assignment information; and
    updating the first role assignment information using the plurality of space information sets,
    wherein the method further comprises operations of:
    acquiring information on distances from the dominant role assignment to the plurality of role assignments, wherein the distances reflect a degree of difference between the dominant role assignment and the plurality of role assignments; and
    determining the irregular role assignment based on the information on the distances.

2. The method of claim 1, wherein the dominant role assignment is the most frequent role assignment among the plurality of role assignments.

3. The method of claim 1, wherein the distances reflect switch ratios from the dominant role assignment to the plurality of role assignments.

4. The method of claim 1, further comprising an operation of determining whether an additional update of the plurality of space information sets or the role assignment information is required.

5. The method of claim 4, wherein the operation of determining whether an additional update is required comprises an operation of determining whether the additional update is required based on whether at least a portion of the role assignment information is changed by the operation of updating the role assignment information.

6. The method of claim 4, wherein the operation of determining whether an additional update is required comprises an operation of determining whether the additional update is required based on whether each time point when the role assignment is changed by the operation of updating the role assignment information is less than or equal to a predetermined threshold value.

7. The method of claim 4, wherein the operation of determining whether an additional update is required comprises an operation of determining whether the additional update is required based on whether a predetermined number of updates have been accomplished.

8. The method of claim 1, further comprising an operation of dividing a target session for one game of a team sport into at least two time periods, wherein the at least two time periods include a first time period and a second time period obtained through division based on a role change of at least some of the plurality of players or a formation change of a team participating in the game,
    wherein the target period is one of the first time period or the second time period.

9. A device for providing tactical information for team sports, the device comprising a processor and a memory, wherein the processor is configured to:
  acquire a plurality of player tracking data sets for a plurality of players, wherein each of the player tracking data sets includes a sequence of location data of a corresponding player during a target period;
  acquire first role assignment information using the plurality of player tracking data sets, wherein the first role assignment information includes a plurality of role assignments for a plurality of time points within the target period, and each of the role assignments is data set which includes a plurality of role indices assigned to the plurality of players at a corresponding time point such that the each of role assignment reflects specific roles of each player of the plurality of players in the same team at the corresponding time point;
  determine a dominant role assignment based on the plurality of role assignments, and wherein the dominant role assignment is related to at least one predetermined team-formation performable by the team;
  determine at least one irregular role assignment from the plurality of role assignments in consideration of the dominant role assignment, and wherein the irregular role assignment is related to roles of the plurality of players that occur during the target period and do not correspond to the predetermined team-formation;
  acquire a plurality of space information sets associated with the target period for each of the plurality of role indices based on second role assignment information and some of the player tracking data sets corresponding to the second role assignment information, and wherein the second role assignment information is that which excludes at least one of the irregular role assignment from the first role assignment information; and
  update the first role assignment information using the plurality of space information sets,
  wherein the processor is further configured to:
  acquire information on distances from the dominant role assignment to the plurality of role assignments, wherein the distances reflect a degree of difference between the dominant role assignment and the plurality of role assignments; and
  determine the irregular role assignment based on the information on the distances.

10. A non-transitory computer-readable storage medium storing instructions executable by a processor, wherein the instructions are executed by the processor to cause the processor to:
  acquire a plurality of player tracking data sets for a plurality of players, wherein each of the player tracking data sets includes a sequence of location data of a corresponding player during a target period;
  acquire first role assignment information using the plurality of player tracking data sets, wherein the first role assignment information includes a plurality of role assignments for a plurality of time points within the target period, and each of the role assignments is data set which includes a plurality of role indices assigned to the plurality of players at a corresponding time point such that the each of role assignment reflects specific roles of each player of the plurality of players in the same team at the corresponding time point;
  determine a dominant role assignment based on the plurality of role assignments, and wherein the dominant role assignment is related to at least one predetermined team-formation performable by the team;
  determine at least one irregular role assignment from the plurality of role assignments in consideration of the dominant role assignment, and wherein the irregular role assignment is related to roles of the plurality of players that occur during the target period and do not correspond to the predetermined team-formation;
  acquire a plurality of space information sets associated with the target period for each of the plurality of role indices based on second role assignment information and some of the player tracking data sets corresponding to the second role assignment information, and wherein the second role assignment information is that which excludes at least one of the irregular role assignment from the first role assignment information; and
  update the first role assignment information using the plurality of space information sets;
  acquire information on distances from the dominant role assignment to the plurality of role assignments, wherein the distances reflect a degree of difference between the dominant role assignment and the plurality of role assignments; and
  determine the irregular role assignment based on the information on the distances.

* * * * *